US012531134B2

(12) United States Patent
Wnuk

(10) Patent No.: US 12,531,134 B2
(45) Date of Patent: Jan. 20, 2026

(54) HLA CLUSTERS, GLOBAL FREQUENCIES, AND BINDING ACROSS SARS-CoV-2 VARIATION

(71) Applicant: NantCell, Inc., Culver City, CA (US)

(72) Inventor: Kamil Wnuk, Playa del Rey, CA (US)

(73) Assignee: NantCell, Inc., Culver City, CA (US)

( * ) Notice: Subject to any disclaimer, the term of this patent is extended or adjusted under 35 U.S.C. 154(b) by 1007 days.

(21) Appl. No.: 17/670,385

(22) Filed: Feb. 11, 2022

(65) Prior Publication Data

US 2022/0262456 A1 Aug. 18, 2022

Related U.S. Application Data

(60) Provisional application No. 63/195,660, filed on Jun. 1, 2021, provisional application No. 63/148,609, filed on Feb. 12, 2021.

(51) Int. Cl.

| | |
|---|---|
| ***G16B 5/20*** | (2019.01) |
| ***A61K 39/215*** | (2006.01) |
| ***G06N 3/044*** | (2023.01) |
| ***G16B 40/20*** | (2019.01) |
| *A61K 39/00* | (2006.01) |

(52) U.S. Cl.

CPC .............. *G16B 5/20* (2019.02); *A61K 39/215* (2013.01); *G06N 3/044* (2023.01); *G16B 40/20* (2019.02); *A61K 2039/53* (2013.01)

(58) Field of Classification Search

CPC .. A61K 39/215; A61K 39/12; A61K 2039/53; G06N 3/08; G06N 3/044; G16B 20/30; G16B 5/20; G16B 40/20; C12N 2770/20034

USPC .......................................................... 703/11

See application file for complete search history.

(56) References Cited

PUBLICATIONS

Dong et al., Contriving Multi-Epitope Subunit of Vaccine for COVID-19: Immunoinformatics Approaches, Frontiers in Immunology, 11:1-18; 2020.*

Lim et al.; Development of multi-epitope peptide-based vaccines against SARS-CoV-2; Biomedical Journal; 44(1):18-30; 2020.*

Ahammad et al.; Designing a novel mRNA vaccine against SARS-CoV-2:An immunoinformatics approach, International Journal of Biological Macromolecules; 162:820-837; 2020.*

(Continued)

*Primary Examiner* — Igor N Borissov

(74) *Attorney, Agent, or Firm* — ROTHWELL, FIGG, ERNST & MANBECK, P.C.

(57) ABSTRACT

Techniques are provided for determining pan-HLA binding of viral proteins. A trained classifier model is operable to determine, independently per HLA, at least one of (a) an average binding prediction of overlapping peptides at each position of a viral protein, (b) a maximum value of a binding prediction of overlapping peptides at each position of the viral protein, (c) standard deviation of a binding prediction of overlapping peptides at each position of the viral protein, and (d) a combination of one or more of (a)-(c). A classification engine uses the classifier model to determine average binding predictions of overlapping peptides at each position of the viral protein independently for test HLA-I and HLA-II functional groupings, where a peptide is classified as a binder when an average binding prediction corresponding to the peptide satisfies a binding value threshold.

30 Claims, 66 Drawing Sheets
(6 of 66 Drawing Sheet(s) Filed in Color)
Specification includes a Sequence Listing.

(56) References Cited

PUBLICATIONS

Grifoni et al., "Candidate targets for immune responses to 2019-Novel Coronavirus (nCoV): sequence homology- and bioinformatic-based predictions," Social Science Research Network, 21 pages.
Nguyen et al., "Human Leukocyte Antigen Susceptibility Map for Severe Acute Respiratory Syndrome Coronavirus 2," Journal of Virology, vol. 94, No. 13, 2020, 29 pages.
Grifoni et al., "Targets of T cell responses to SARS-CoV-2 coronavirus in humans with COVID-19 disease and unexposed individuals," Cell, vol. 181, No. 7, 2020, 33 pages.
Yarmarkovich et al., "Identification of SARS-CoV-2 Vaccine Epitopes Predicted to Induce Longterm Population-Scale Immunity," Cell Reports Medicine, vol. 1, No. 3, 2020, 19 pages.
Lan et al., "Structure of the SARS-CoV-2 spike receptor-binding domain bound to the ACE2 receptor," Nature, vol. 581, No. 7807, 2020, 16 pages.

* cited by examiner

| | PAD | PAD | A | L | A | T | F | T | V | N | I |
|---|---|---|---|---|---|---|---|---|---|---|---|
| A | 0 | 0 | 1 | 0 | 1 | 0 | 0 | 0 | 0 | 0 | 0 |
| C | 0 | 0 | 0 | 1 | 0 | 0 | 0 | 0 | 0 | 0 | 0 |
| D | 0 | 0 | 0 | 0 | 0 | 0 | 0 | 0 | 0 | 0 | 0 |
| E | 0 | 0 | 0 | 0 | 0 | 0 | 0 | 0 | 0 | 0 | 0 |
| • | • | • | • | • | • | • | • | • | • | • | • |
| • | • | • | • | • | • | • | • | • | • | • | • |
| • | • | • | • | • | • | • | • | • | • | • | • |
| T | 0 | 0 | 0 | 0 | 0 | 1 | 0 | 1 | 0 | 0 | 0 |
| V | 0 | 0 | 0 | 0 | 0 | 0 | 0 | 0 | 1 | 0 | 0 |
| W | 0 | 0 | 0 | 0 | 0 | 0 | 0 | 0 | 0 | 0 | 0 |
| Y | 0 | 0 | 0 | 0 | 0 | 0 | 0 | 0 | 0 | 0 | 0 |

400

500

900

Pan HLA-I binding hotspots in SARS-CoV-2 N protein

Pan HLA-II binding hotspots in SARS-CoV-2 N protein

Pan HLA-I binding hotspots in SARS-CoV-2 N protein

1100

Pan HLA-I binding hotspots in SARS-CoV-2 N protein

1200

Pan HLA-II binding hotspots in SARS-CoV-2 N protein

1300

1304

1302

Pan HLA-I binding hotspots in SARS-CoV-2 N protein

1400

Pan HLA-II binding hotspots in SARS-CoV-2 N protein

1700

Pan-HLA-{I,II} binding hotspots in SARS-CoV-2 S protein

Example Client-Server Relationship

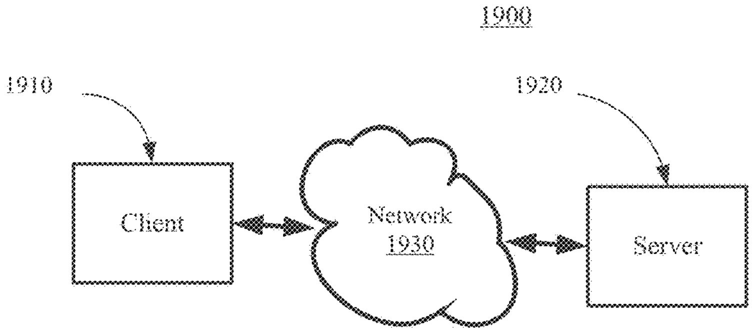

- obtain viral protein encoded into variable-length peptides
- obtain plurality of HLAs encoded into variable-length proteins, where the plurality of HLAs may comprise HLA-I and HLA-II functional groupings

- configure a classifier model trained to process encoded variable-length peptides
- configure a classification engine to use the classifier model to determine average binding predictions of overlapping peptides at each position of the viral protein independently for each of a plurality of test HLAs comprising HLA-I and HLA-II functional groupings
- obtain a plurality of test HLAs encoded into variable-length proteins, where the plurality of test HLAs comprises HLA-I and HLA-II functional groupings;
- process the encoded variable-length peptides corresponding to the viral protein and the variable-length proteins corresponding to the plurality of test HLAs using the classifier model
- Independently per test HLA, map in aggregate average binding predictions to locations along the test viral protein such that peptide-HLA interaction is indicated; determine nearest max locations for the average binding predictions using a sliding window having a fixed length; determine top max regions by selecting the nearest max locations having average binding predictions within a top percentage of values; select peptides classified as binders that overlap the top max regions; and determine a pan-HLA max region
- Independently for HLA-I and HLA-II functional groupings, filter selected peptides classified as binders to identify candidate peptides that overlap top max regions based on aggregate of pan-HLA max regions, where one or more of the candidate peptides may be included in mRNA-based vaccine or therapeutic treatment for a patient

FIG. 19

Run-MHC: Recurrent Neural Net with Attention & MHC-SEQ(work of Jeremi Sudol): Convolutional Neural Net

- Inputs: full peptide and HLA protein sequences [any length]
- High uncertainty predictions are labeled *ambiguous*
- Introspection into important positions on both sides of binding pocket [Run-MHC]
- Enables functional HLA similarity clustering of HLA-I and HLA-II Comparison with NetMHCpan4.1 (Reynisson et al., July 2020, *Nucleic Acids Research*)

| [illegible] | Run-MHC (no ambig) | Run-MHC | MHC-SEQ (no ambig) | MHC-SEQ | NetMHCpan 4.1 | NetMHCpan 4.1 | MHCFlurry | [illegible] | [illegible] |
|---|---|---|---|---|---|---|---|---|---|
| Mean ROC AUC | 0.9637 | 0.9639 | [illegible] | 0.9602 | 0.9498 | 0.9462 | 0.9335 | 0.9333 | 0.9324 |
| Mean PPV [illegible] | 0.8237 | 0.8038 | 0.8823 | 0.8637 | 0.8162 | 0.7860 | 0.7255 | 0.7131 | 0.7705 |

MHCI pan-allele binding architecture

MHCII pan-allele binding architecture

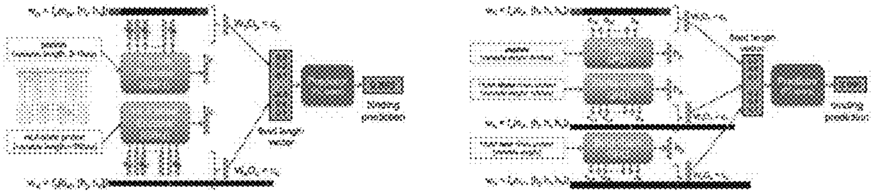

FIG. 21

Learned HLA functional similarity grouping

- Ensure all HLA-I and HLA-II clusters are covered in binding analyses intended to cover world population
- 38 HLA-I clusters: 114 HLA-I alleles selected for analysis
- 93 HLA-II clusters in all alpha + beta permutations: 373 HLA-II alpha + beta pairs selected for analysis
  - 18 HLA-II alpha clusters: 37 unique alpha chains in analysis set
  - 16 HLA-II beta clusters: 66 unique beta chains in analysis set

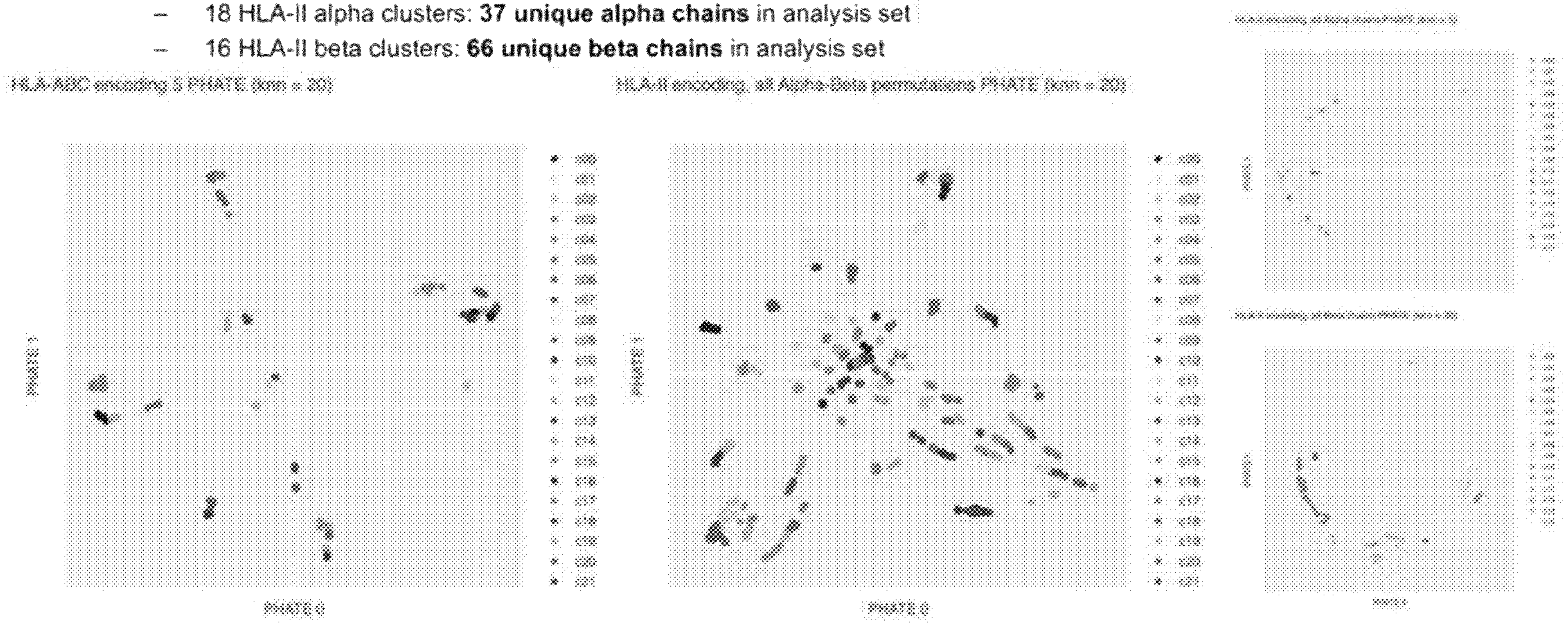

FIG. 24

Method: HLA selection

- World HLA frequencies obtained from Allele Frequency Net Database (http://allelefrequencies.net/)
- HLA-I:
  - Select top 2 highest frequency HLAs from each of 38 clusters (76 HLAs selected)
  - Compute mean, median, and standard deviation (STD) of selected 76 HLA frequencies
  - Add to selected list all HLAs with frequency >= [min(mean,median) – 0.6 * STD] = 0.028503 - 0.019418 = 0.009085
  - 0.6 was used so that the frequency threshold ensured all top 100 most frequent HLA-I were included in the final list
  - Total 114 HLA-I alleles selected
- HLA-II:
  - Select top 2 highest frequency HLA-II alpha chains from each of 18 clusters (32 selected – 4 alpha chains were singular clusters)
  - Add to selected list all HLA-II alpha chains with frequency >= [min(mean,median) – 0.5 * STD] = 0.098436 - 0.088983 = 0.009453
  - Total 33 HLA-II alpha chains selected

- Select top 3 highest frequency HLA-II beta chains from each of 16 clusters (47 selected)
  - Add to selected list all HLA-II beta chains with frequency >= [min(mean,median) – 0.5 * STD] = 0.057828 - 0.051379 = 0.006449
  - Total 47 + 52 = 99 HLA-II beta chains selected

- Create all permutations of potentially matching selected alpha + beta chains above = 645
  - Add top 2 HLA-II alpha + beta pairs from any of the 33 HLA-II alpha + beta clusters not covered by above permutations
  - [Sort order is defined by max(alpha_frequency, beta_frequency) first at 4 digit allele resolution, and secondary at 2 digit allele resolution]
  - Total 691 HLA-II alpha + beta pairs

- Some of the 33 clusters of HLA-II alpha + beta pairs are very highly sampled
  - (Ex: one cluster with DRA*01:01, DRA*01:02, DOA*01:02, DOA*01:02 + matched beta chains has 48 selected alpha + beta pairs)
  - For each of the 33 HLA-II alpha + beta clusters, remove selected pairs from analysis set only if:
  - (1) they are not in the top 2 samples representing a unique combination of independent alpha cluster label (of 18 above) and beta cluster label (of 16 above)
  - (2) the beta chain frequency at 4 digit resolution <= 0.05
  - Total 373 HLA-II alpha + beta pairs selected (37 unique alpha, 66 unique beta)

FIG. 25

Updated Pan-HLA-{I,II} binding hotspots in SARS-CoV-2
S protein

Note: Hotspot locations are mapped to each protein variant in later analysis

Updated Pan-HLA-{I,II} binding hotspots in SARS-CoV-2
N protein

Note: Hotspot locations are mapped to each protein variant in later analysis

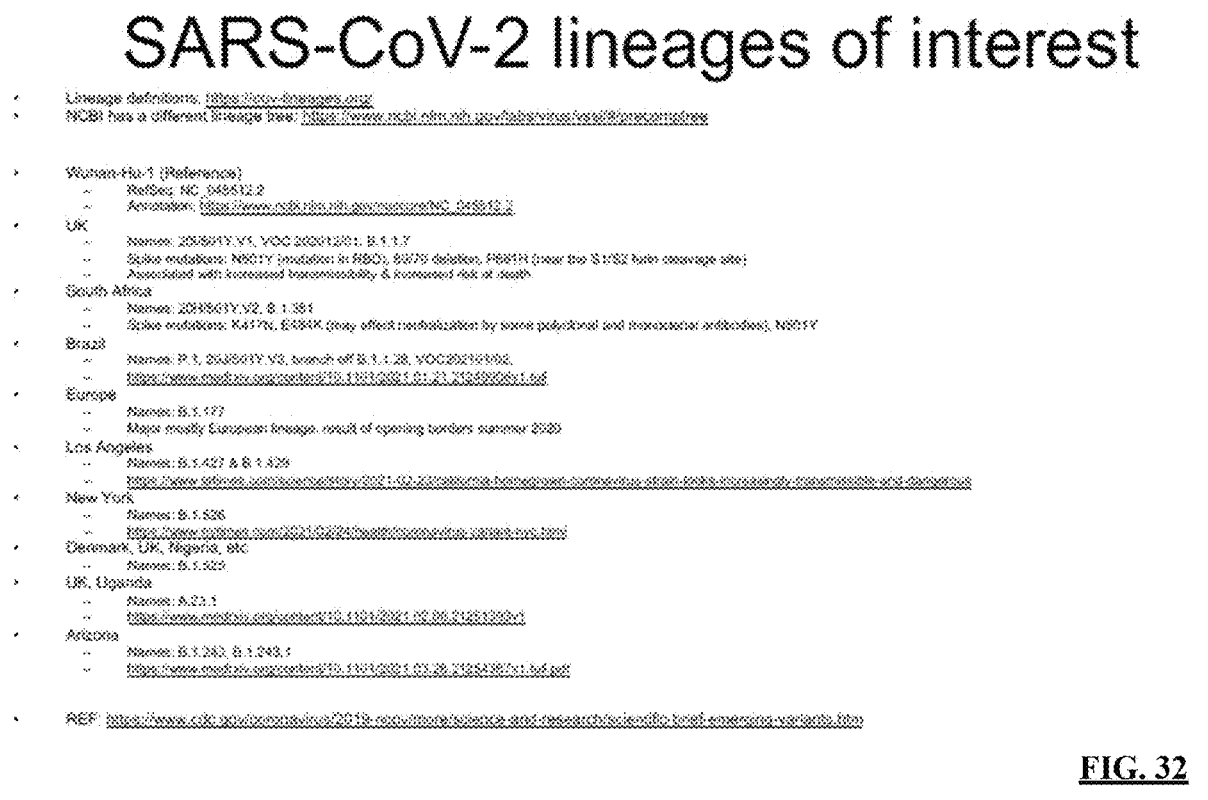

SARS-CoV-2 lineages of interest

- Lineage definitions: https://cov-lineages.org/
- NCBI has a different lineage tree: [illegible]

- Wuhan-Hu-1 (Reference)
  - RefSeq: NC_045512.2
  - Annotation: [illegible]
- UK
  - Names: 20I/501Y.V1, VOC 202012/01, B.1.1.7
  - Spike mutations: N501Y (mutation in RBD), 69/70 deletion, P681H (near the S1/S2 furin cleavage site)
  - Associated with increased transmissibility & increased risk of death
- South Africa
  - Names: 20H/501Y.V2, B.1.351
  - Spike mutations: K417N, E484K (may affect neutralization by some polyclonal and monoclonal antibodies), N501Y
- Brazil
  - Names: P.1, 20J/501Y.V3, branch off B.1.1.28, VOC202101/02,
  - [illegible]
- Europe
  - Names: B.1.177
  - Major mostly European lineage, result of opening borders summer 2020
- Los Angeles
  - Names: B.1.427 & B.1.429
  - [illegible]
- New York
  - Names: B.1.526
  - [illegible]
- Denmark, UK, Nigeria, etc
  - Names: B.1.525
- UK, Uganda
  - Names: A.23.1
  - [illegible]
- Arizona
  - Names: B.1.243, B.1.243.1
  - [illegible]

- REF: [illegible]

FIG. 32

- https://cov-lineages.org/lineages/lineage_B.1.1.7.html
- https://www.ecdc.europa.eu/sites/default/files/documents/SARS-CoV-2-variant-multiple-spike-protein-mutations-United-Kingdom.pdf

B.1.351: South Africa

- https://cov-lineages.org/lineages/lineage_B.1.351.html

B.1.1.28, P1, P2: Brazil

- https://cov-lineages.org/lineages/lineage_B.1.1.28.html
- https://www.medrxiv.org/content/10.1101/2021.01.21.21249906v1.full

B.1.177: Europe

- https://cov-lineages.org/lineages/lineage_B.1.177.html

B.1.427: Los Angeles

- https://cov-lineages.org/lineages/lineage_B.1.427.html
- https://www.latimes.com/science/story/2021-02-23/california-homegrown-coronavirus-strain-looks-increasingly-transmissible-and-dangerous

B.1.429: Los Angeles

- https://cov-lineages.org/lineages/lineage_B.1.429.html

B.1.526: New York

- https://cov-lineages.org/lineages/lineage_B.1.526.html
- https://www.nytimes.com/2021/02/24/health/coronavirus-variant-nyc.html

B.1.525: Denmark, UK, Nigeria

- https://cov-lineages.org/lineages/lineage_B.1.525.html
- https://cov-lineages.org/global_report_B.1.525.html

A.23.1: UK, Uganda

- https://cov-lineages.org/lineages/lineage_A.23.1.html
- https://cov-lineages.org/global_report_A.23.1.html
- https://www.medrxiv.org/content/10.1101/2021.02.08.21251393v1

B.1.243: USA, Arizona

- https://cov-lineages.org/lineages/lineage_B.1.243.html
- https://www.medrxiv.org/content/10.1101/2021.03.26.21254367v1.full.pdf

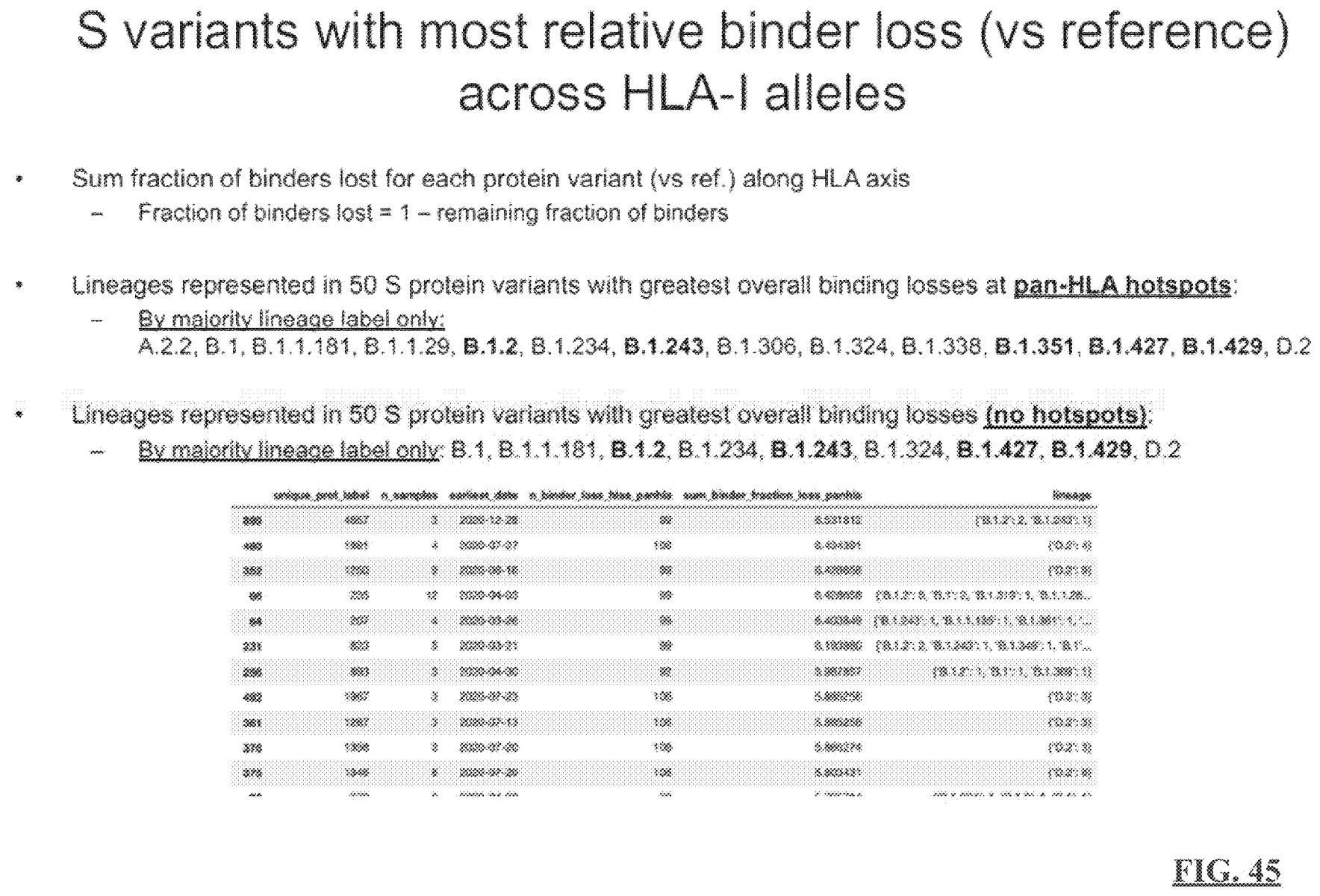

S variants with most relative binder loss (vs reference) across HLA-I alleles

- Sum fraction of binders lost for each protein variant (vs ref.) along HLA axis
  - Fraction of binders lost = 1 – remaining fraction of binders
- Lineages represented in 50 S protein variants with greatest overall binding losses at pan-HLA hotspots:
  - By majority lineage label only:
    A.2.2, B.1, B.1.1.181, B.1.1.29, B.1.2, B.1.234, B.1.243, B.1.306, B.1.324, B.1.338, B.1.351, B.1.427, B.1.429, D.2
- Lineages represented in 50 S protein variants with greatest overall binding losses (no hotspots):
  - By majority lineage label only: B.1, B.1.1.181, B.1.2, B.1.234, B.1.243, B.1.324, B.1.427, B.1.429, D.2

| | unique_prot_label | n_samples | earliest_date | n_binder_loss_hlas_pan... | sum_binder_fraction_loss_pan... | lineage |
|---|---|---|---|---|---|---|
| [illegible] | [illegible] | 3 | 2020-12-[illegible] | [illegible] | [illegible] | {'B.1.2': 2, 'B.1.[illegible]': 1} |
| [illegible] | [illegible] | 4 | 2020-07-[illegible] | 100 | [illegible] | {'D.2': 4} |
| [illegible] | [illegible] | 3 | 2020-[illegible] | [illegible] | [illegible] | {'D.2': 3} |
| [illegible] | [illegible] | 12 | 2020-04-[illegible] | [illegible] | [illegible] | {'B.1.2': [illegible], 'B.1': [illegible], 'B.1.[illegible]': 1, 'B.1.1.[illegible]... |
| [illegible] | [illegible] | 4 | 2020-[illegible] | [illegible] | [illegible] | {'B.1.[illegible]': 1, 'B.1.1.[illegible]': 1, 'B.1.[illegible]': 1, '... |
| [illegible] | [illegible] | 5 | 2020-[illegible] | [illegible] | [illegible] | {'B.1.2': 2, 'B.1.[illegible]': 1, 'B.1.[illegible]': 1, 'B.1... |
| [illegible] | [illegible] | 3 | 2020-04-[illegible] | [illegible] | [illegible] | {'B.1.2': 1, 'B.1': 1, 'B.1.[illegible]': 1} |
| [illegible] | [illegible] | 3 | 2020-07-[illegible] | 100 | [illegible] | {'D.2': 3} |
| [illegible] | [illegible] | 3 | 2020-07-[illegible] | 100 | [illegible] | {'D.2': 3} |
| [illegible] | [illegible] | 3 | 2020-07-[illegible] | 100 | [illegible] | {'D.2': 3} |
| [illegible] | [illegible] | [illegible] | 2020-07-[illegible] | 100 | [illegible] | {'D.2': [illegible]} |
| [illegible] | [illegible] | [illegible] | [illegible] | [illegible] | [illegible] | [illegible] |

FIG. 45

B.1.2: USA

- https://cov-lineages.org/lineages/lineage_B.1.2.html

D.2: Australia

- https://cov-lineages.org/lineages/lineage_D.2.html

Change in HLA-II binder count at panHLA-I,II hotspots relative to ref. S protein See interactive file:

HLA-II binder count change at pan-HLA-{I,II} hotspots:

hla2v0.2.9_20210319_S_bindcount_vs_ref_panhla.html

S variants with most relative binder loss (vs reference) across HLA-II alleles

- Sum fraction of binders lost for each protein variant (vs ref.) along HLA axis
  - Fraction of binders lost = 1 – remaining fraction of binders

- Lineages represented in 50 S protein variants with greatest overall binding losses at pan-HLA hotspots:
  - By majority lineage label only:
    A.2.2, B.1, B.1.1.291, B.1.2, B.1.234, B.1.243, B.1.306, B.1.311, B.1.324, B.1.338, B.1.361, B.1.369, B.1.427, B.1.429, B.1.525, D.2, P.1, P.2

- Lineages represented in 50 S protein variants with greatest overall binding losses (no hotspots):
  - By majority lineage label only:
    B.1, B.1.1.7, B.1.2, B.1.232, B.1.243, B.1.311, B.1.324, B.1.361, B.1.369, B.1.427, B.1.429, B.1.525, D.2, P.1, P.2

FIG. 50

Change in HLA-II binder count at panHLA-I,II hotspots relative to ref. S protein See interactive file:

HLA-II binder count change at pan-HLA-{I,II} hotspots:

hla2v0.2.9_20210319_S_bindcount_vs_ref_panhla_loessorted.html

B.1.369: USA / New Zealand / Canada

- https://cov-lineages.org/lineages/lineage_B.1.369.html

Change in HLA-I binder count at panHLA-I,II hotspots relative to ref. N protein

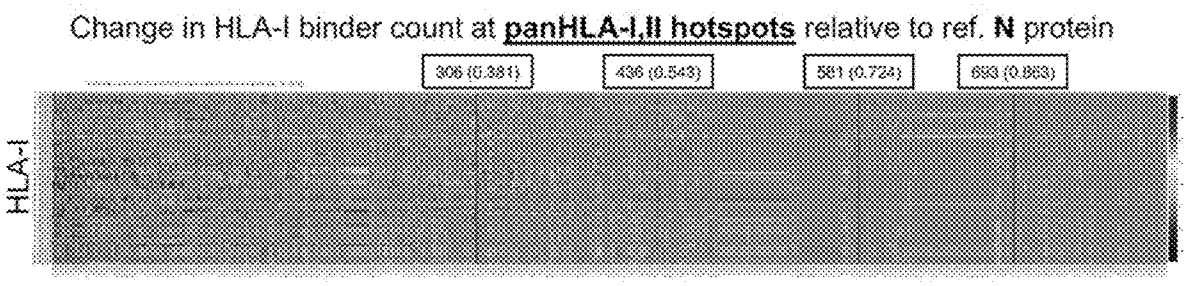

N protein variants (sorted by sum fraction binder loss)

Ranking thresholds:

At 306 (0.3811) sum of binder loss fraction across all HLAs is 0.5700 (0.005 average loss fraction per HLA)
At 436 (0.5430) sum of binder loss fraction across all HLAs is 0.2280 (0.002 average loss fraction per HLA)
At 581 (0.7235) sum of binder loss fraction across all HLAs is 0.1140 (0.001 average loss fraction per HLA)
Beyond 693 (0.8630) there are NO BINDER LOSSES AT ALL.

Protein variants (x-axis) sorted by:
1. Sum fraction of binders lost for each protein variant along HLA axis (left = most lost binders)

Lineages often have multiple unique variants of a protein.

One specific protein sequence may correspond to multiple lineages.

See interactive file:
HLA-I binder count change at pan-HLA-{I,II} hotspots:
hlaABCv0.2.9_20210319_N_bindcount_vs_ref_panhla_losssorted.html

FIG. 53

N variants with most relative binder loss (vs reference) across HLA-I alleles

- Sum fraction of binders lost for each protein variant (vs ref.) along HLA axis
  - Fraction of binders lost = 1 – remaining fraction of binders

- Lineages represented in 40 N protein variants with greatest overall binding losses at pan-HLA hotspots:
  - By majority lineage label only:
    B.1, B.1.1.1, B.1.1.135, B.1.1.231, B.1.1.281, B.1.110.3, B.1.111, B.1.189, B.1.2, B.1.234, B.1.240, B.1.36, B.1.369, B.1.503, B.1.509, B.1.78, B.46, D.2

- Lineages represented in 40 N protein variants with greatest overall binding losses (no hotspots):
  - By majority lineage label only:
    B.1, B.1.1.1, B.1.1.135, B.1.1.281, B.1.189, B.1.2, B.1.509, B.1.78, B.46, D.2

FIG. 54

N variants with most relative binder loss (vs reference) across HLA-II alleles

- Sum fraction of binders lost for each protein variant (vs ref.) along HLA axis
  - Fraction of binders lost = 1 – remaining fraction of binders

- Lineages represented in 40 N protein variants with greatest overall binding losses at <u>pan-HLA hotspots</u>:
  - <u>By majority lineage label only:</u>
    B.1, B.1.1, B.1.1.222, B.1.1.281, B.1.1.29, B.1.1.291, B.1.2, B.1.234, B.1.240, B.1.243, B.1.258, B.1.335, B.1.346, B.1.361, B.1.400, B.1.429, B.1.479, B.1.494, B.1.496, B.1.509, B.1.523, B.1.8, B.46, D.2

- Lineages represented in 40 N protein variants with greatest overall binding losses <u>(no hotspots)</u>:
  - <u>By majority lineage label only:</u>
    B.1, B.1.1.222, B.1.1.281, B.1.1.29, B.1.1.291, B.1.124, B.1.2, B.1.234, B.1.240, B.1.243, B.1.258, B.1.346, B.1.361, B.1.400, B.1.429, B.1.451, B.1.479, B.1.494, B.1.496, B.1.509, B.1.523, B.1.8, B.46, D.2

FIG. 56

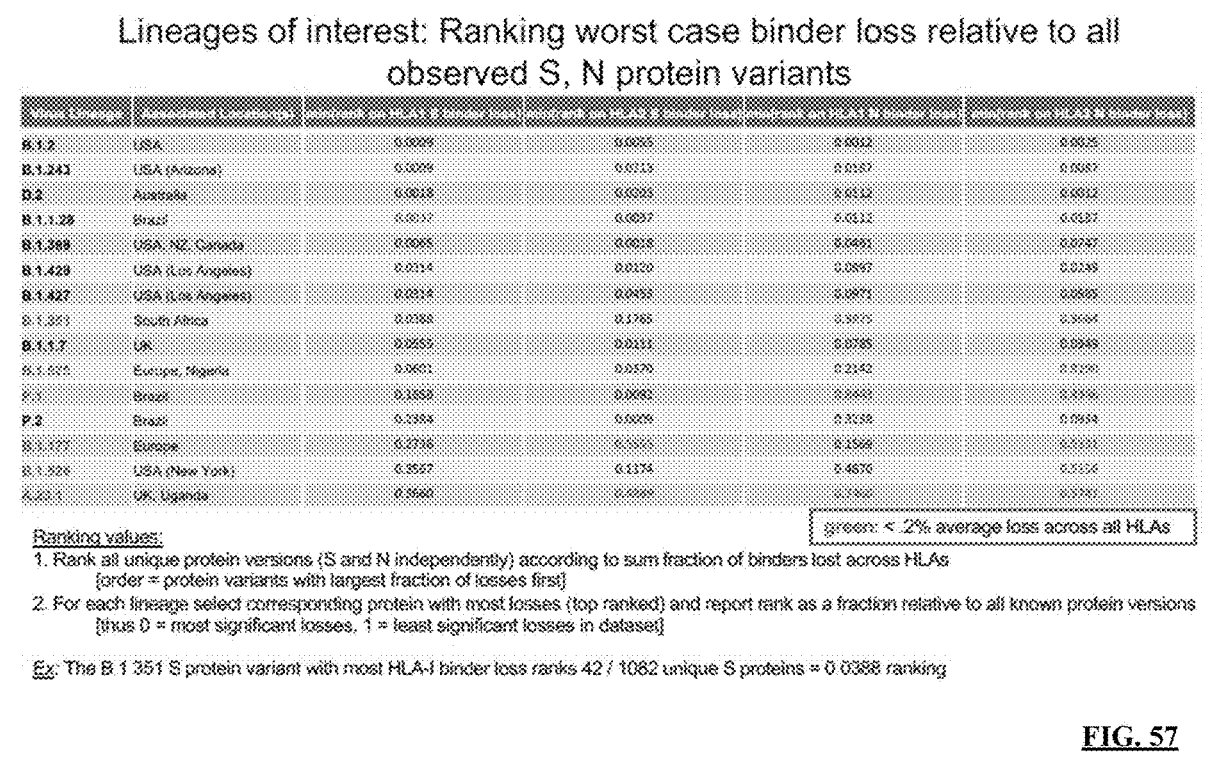

Lineages of interest: Ranking worst case binder loss relative to all observed S, N protein variants

| | | | | | |
|---|---|---|---|---|---|
| B.1.2 | USA | 0.0029 | 0.0035 | 0.0012 | 0.0025 |
| B.1.243 | USA (Arizona) | 0.0029 | 0.0113 | 0.0187 | 0.0087 |
| D.2 | Australia | 0.0018 | 0.0035 | 0.0112 | 0.0012 |
| B.1.1.28 | Brazil | 0.0017 | 0.0037 | 0.0112 | 0.0127 |
| B.1.389 | USA, NZ, Canada | 0.0065 | 0.0028 | 0.0491 | 0.0747 |
| B.1.429 | USA (Los Angeles) | 0.0314 | 0.0120 | 0.0897 | 0.0249 |
| B.1.427 | USA (Los Angeles) | 0.0314 | 0.0453 | 0.0971 | 0.0865 |
| B.1.351 | South Africa | 0.0388 | 0.1765 | [illegible] | [illegible] |
| B.1.1.7 | UK | 0.0253 | 0.0131 | 0.0785 | 0.0349 |
| B.1.525 | Europe, Nigeria | 0.0601 | 0.0570 | 0.2142 | [illegible] |
| P.1 | Brazil | 0.1059 | 0.0082 | [illegible] | [illegible] |
| P.2 | Brazil | 0.1354 | 0.0026 | 0.3138 | 0.0934 |
| B.1.177 | Europe | 0.2716 | [illegible] | 0.1568 | [illegible] |
| B.1.526 | USA (New York) | 0.3597 | 0.1174 | 0.4570 | 0.3134 |
| A.23.1 | UK, Uganda | 0.3560 | [illegible] | [illegible] | [illegible] |

green: < .2% average loss across all HLAs

Ranking values:

1. Rank all unique protein versions (S and N independently) according to sum fraction of binders lost across HLAs
[order = protein variants with largest fraction of losses first]
2. For each lineage select corresponding protein with most losses (top ranked) and report rank as a fraction relative to all known protein versions
[thus 0 = most significant losses, 1 = least significant losses in dataset]

Ex: The B.1.351 S protein variant with most HLA-I binder loss ranks 42 / 1082 unique S proteins = 0.0388 ranking

FIG. 57

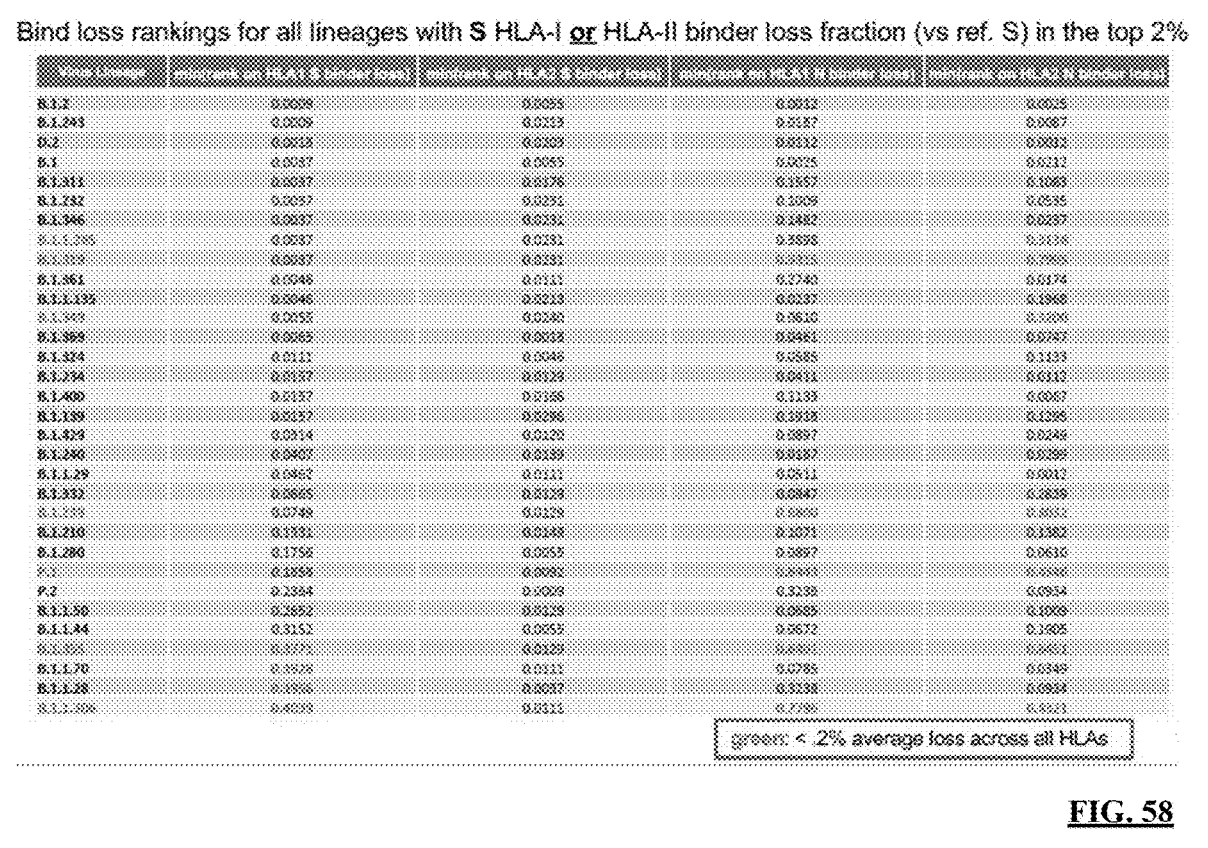

Bind loss rankings for all lineages with S HLA-I or HLA-II binder loss fraction (vs ref. S) in the top 2%

| [illegible] | [illegible] | [illegible] | [illegible] | [illegible] |
|---|---|---|---|---|
| B.1.2 | 0.0098 | 0.0055 | 0.0012 | 0.0025 |
| B.1.243 | 0.0009 | 0.0253 | 0.0187 | 0.0087 |
| D.2 | 0.0018 | 0.0009 | 0.0212 | 0.0012 |
| B.1 | 0.0037 | 0.0055 | 0.0025 | 0.0212 |
| B.1.311 | 0.0037 | 0.0176 | 0.1657 | 0.1063 |
| B.1.232 | 0.0037 | 0.0251 | 0.1009 | 0.0535 |
| B.1.346 | 0.0037 | 0.0231 | 0.1482 | 0.0237 |
| [illegible] | 0.0037 | 0.0231 | 0.3898 | 0.3136 |
| [illegible] | 0.0037 | 0.0231 | [illegible] | [illegible] |
| B.1.361 | 0.0046 | 0.0111 | 0.2740 | 0.0174 |
| B.1.1.135 | 0.0046 | 0.0213 | 0.0237 | 0.1968 |
| [illegible] | 0.0055 | 0.0240 | 0.0610 | [illegible] |
| B.1.369 | 0.0065 | 0.0018 | 0.0461 | 0.0747 |
| B.1.324 | 0.0111 | 0.0046 | 0.0585 | 0.1133 |
| B.1.234 | 0.0157 | 0.0129 | 0.0411 | 0.0112 |
| B.1.400 | 0.0157 | 0.0166 | 0.1133 | 0.0067 |
| B.1.139 | 0.0157 | 0.0296 | 0.3918 | 0.1286 |
| B.1.429 | 0.0314 | 0.0120 | 0.0897 | 0.0249 |
| B.1.240 | 0.0407 | 0.0139 | 0.0187 | 0.0299 |
| B.1.1.29 | 0.0462 | 0.0111 | 0.0511 | 0.0012 |
| B.1.332 | 0.0605 | 0.0129 | 0.0847 | 0.2839 |
| [illegible] | 0.0748 | 0.0129 | [illegible] | [illegible] |
| B.1.210 | 0.1331 | 0.0148 | 0.1071 | 0.1382 |
| B.1.280 | 0.1756 | 0.0055 | 0.0897 | 0.0610 |
| P.1 | 0.1858 | 0.0092 | [illegible] | [illegible] |
| P.2 | 0.2384 | 0.0009 | 0.3238 | 0.0934 |
| B.1.1.50 | 0.2652 | 0.0129 | 0.0685 | 0.1009 |
| B.1.1.44 | 0.3152 | 0.0055 | 0.0672 | 0.1805 |
| [illegible] | [illegible] | 0.0129 | [illegible] | [illegible] |
| B.1.1.70 | [illegible] | 0.0111 | 0.0785 | 0.0349 |
| B.1.1.28 | [illegible] | 0.0037 | 0.3238 | 0.0934 |
| [illegible] | 0.4039 | 0.0111 | [illegible] | [illegible] |

green: < .2% average loss across all HLAs

FIG. 58

Conclusions: B.1.351

- Compared to other SARS-CoV-2 lineages potential binder loss of B.1.351 S protein is not a large fraction relative to reference S
  - The B.1.351 S protein variant with most HLA-I binder loss ranks 42 / 1082 unique S proteins (0.0388 ranking)
  - The B.1.351 S protein variant with most HLA-II binder loss ranks 191 / 1082 unique S proteins (0.1765 ranking)

- Potential binder loss of B.1.351 N protein is ranked near the end compared to almost all other observed versions of the N protein [no binding loss potential vs reference]
  - The B.1.351 N protein variant with most HLA-I binder loss ranks 793 / 803 unique N proteins (0.9875 ranking)
  - The B.1.351 N protein variant with most HLA-II binder loss ranks 776 / 803 unique N proteins (0.9664 ranking)
  - B.1.351 N protein has no predicted binding losses at pan-HLA hotspots for either HLA-I or HLA-II

- B.1.351 is a great example lineage where conserved binding of epitopes in N to HLA-I and HLA-II complements any potential losses in S

FIG. 59

Conclusions: Lineages of Interest

- From the 15 lineages of interest:
  - 3 have N with very low loss in binders (< .2% average loss across all HLAs) for both HLA-I and HLA-II

| lineage | location | HLA1_S_min_lossrank_fract | HLA2_S_min_lossrank_fract | HLA1_N_min_lossrank_fract | HLA2_N_min_lossrank_fract |
|---|---|---|---|---|---|
| B.1.351 | South Africa | 0.038817 | 0.176525 | 0.987547 | 0.966378 |
| P.1 | Brazil | 0.185767 | 0.009242 | 0.844334 | 0.434620 |
| A.23.1 | UK, Uganda | 0.385989 | 0.488909 | 0.745953 | 0.574097 |

- 6 have N with very low loss in binders (< .2% average loss across all HLAs) for either HLA-I or HLA-II

| lineage | location | HLA1_S_min_lossrank_fract | HLA2_S_min_lossrank_fract | HLA1_N_min_lossrank_fract | HLA2_N_min_lossrank_fract |
|---|---|---|---|---|---|
| B.1.351 | South Africa | 0.038817 | 0.176525 | 0.987547 | 0.966378 |
| B.1.525 | Europe, Nigeria | 0.080074 | 0.036969 | 0.214187 | 0.929018 |
| P.1 | Brazil | 0.185767 | 0.009242 | 0.844334 | 0.434620 |
| B.1.177 | Europe | 0.273587 | 0.555453 | 0.158912 | 0.513076 |
| B.1.526 | USA (New York) | 0.356747 | 0.117375 | 0.468999 | 0.615567 |
| A.23.1 | UK, Uganda | 0.385989 | 0.488909 | 0.745953 | 0.574097 |

FIG. 60

Conclusions: Lineages with S in top 2% sum fraction of binders lost for HLA-I or HLA-II

- S + N vaccine may have an edge on the strains below that may be challenging for S only vaccines

- From the 32 lineages ranked in top 2% of binder loss across HLAs in S:
  - 5 (0.156) have N with very low loss in binders (< .2% average loss across all HLAs) for both HLA-I and HLA-II

| lineage | HLA1_S_min_lossrank_fract | HLA2_S_min_lossrank_fract | HLA1_N_min_lossrank_fract | HLA2_N_min_lossrank_fract |
|---|---|---|---|---|
| B.1.319 | 0.003697 | 0.023105 | 0.931507 | 0.798502 |
| B.1.239 | 0.074861 | 0.012939 | 0.679950 | 0.803238 |
| P1 | 0.185787 | 0.009242 | 0.844334 | 0.434620 |
| B.1.355 | 0.377079 | 0.012939 | 0.640100 | 0.645081 |
| B.1.1.306 | 0.403882 | 0.011091 | 0.779577 | 0.432130 |

- 7 (0.219) have N with very low loss in binders (< .2% average loss across all HLAs) for either HLA-I or HLA-II

| lineage | HLA1_S_min_lossrank_fract | HLA2_S_min_lossrank_fract | HLA1_N_min_lossrank_fract | HLA2_N_min_lossrank_fract |
|---|---|---|---|---|
| B.1.1.289 | 0.003697 | 0.023105 | 0.389788 | 0.313823 |
| B.1.319 | 0.003697 | 0.023105 | 0.931507 | 0.798502 |
| B.1.349 | 0.005545 | 0.024030 | 0.061021 | 0.330050 |
| B.1.239 | 0.074861 | 0.012939 | 0.679950 | 0.803238 |
| P1 | 0.185787 | 0.009242 | 0.844334 | 0.434620 |
| B.1.355 | 0.377079 | 0.012939 | 0.640100 | 0.645081 |
| B.1.1.306 | 0.403882 | 0.011091 | 0.779577 | 0.432130 |

FIG. 61

Conclusions: Lineages with S in top 5% sum fraction of binders lost for HLA-I or HLA-II

- S + N vaccine may have an edge on the strains below that may be challenging for S only vaccines

- From the 54 lineages ranked in top 5% of binder loss across HLAs in S:
  - 14 (0.259) have N with very low loss in binders (< .2% average loss across all HLAs) for both HLA-I and HLA-II (left)
  - 19 (0.352) have N with very low loss in binders (< .2% average loss across all HLAs) for either HLA-I or HLA-II (right)

| lineage | HLA1_S_min_lossrank_fract | HLA2_S_min_lossrank_fract | HLA1_N_min_lossrank_fract | HLA2_N_min_lossrank_fract |
|---|---|---|---|---|
| B.1.319 | 0.033697 | 0.023106 | 0.901507 | 0.790602 |
| B.1.351 | 0.038817 | 0.178535 | 0.987547 | 0.988376 |
| B.1.306 | 0.040069 | 0.038817 | 0.968196 | 0.898038 |
| B.1.283 | 0.042514 | 0.048039 | 0.955198 | 0.888638 |
| B.1.23 | 0.043439 | 0.038817 | 0.264032 | 0.898038 |
| B.1.1.137 | 0.043438 | 0.038817 | 0.738518 | 0.432130 |
| A.2.2 | 0.044062 | 0.037986 | 0.877984 | 0.998697 |
| B.31 | 0.044082 | 0.037985 | 0.990587 | 0.646461 |
| B.1.1.181 | 0.045287 | 0.280337 | 0.779677 | 0.432130 |
| B.1.1.219 | 0.047136 | 0.277284 | 0.779677 | 0.432130 |
| B.1.239 | 0.074881 | 0.012908 | 0.678953 | 0.603238 |
| P.1 | 0.163787 | 0.008542 | 0.844334 | 0.434820 |
| B.1.362 | 0.277076 | 0.012938 | 0.840132 | 0.645081 |
| B.1.1.308 | 0.469882 | 0.011591 | 0.779677 | 0.432130 |

| lineage | HLA1_S_min_lossrank_fract | HLA2_S_min_lossrank_fract | HLA1_N_min_lossrank_fract | HLA2_N_min_lossrank_fract |
|---|---|---|---|---|
| B.1.1.295 | 0.030697 | 0.023106 | 0.398108 | 0.218823 |
| B.1.319 | 0.033697 | 0.023106 | 0.901507 | 0.790602 |
| B.1.366 | 0.036046 | 0.034630 | 0.261921 | 0.320060 |
| B.1.308 | 0.038272 | 0.033272 | 0.357265 | 0.673734 |
| B.1.351 | 0.038817 | 0.178535 | 0.986547 | 0.988376 |
| B.1.1.216 | 0.038761 | 0.036044 | 0.246075 | 0.348886 |
| B.1.306 | 0.040069 | 0.038817 | 0.968196 | 0.898038 |
| B.1.283 | 0.042514 | 0.048039 | 0.955198 | 0.888638 |
| B.1.23 | 0.043439 | 0.038817 | 0.264032 | 0.898038 |
| B.1.1.137 | 0.043438 | 0.038817 | 0.738518 | 0.432130 |
| A.2.2 | 0.044062 | 0.037986 | 0.877984 | 0.998697 |
| B.31 | 0.044082 | 0.037985 | 0.990587 | 0.646461 |
| B.1.1.181 | 0.045287 | 0.280337 | 0.779677 | 0.432130 |
| B.1.1.219 | 0.047136 | 0.277284 | 0.779677 | 0.432130 |
| B.1.320 | 0.060074 | 0.008969 | 0.214197 | 0.300603 |
| B.1.239 | 0.074881 | 0.012908 | 0.678953 | 0.603238 |
| P.1 | 0.163787 | 0.008542 | 0.844334 | 0.434820 |
| B.1.362 | 0.277076 | 0.012938 | 0.840132 | 0.645081 |
| B.1.1.308 | 0.469882 | 0.011591 | 0.779677 | 0.432130 |

FIG. 62

Conclusions: Lineages with S in top 10% sum fraction of binders lost for HLA-I or HLA-II

- S + N vaccine may have an edge on the strains below that may be challenging for S only vaccines
- From the 93 lineages ranked in top 10% of binder loss across HLAs in S:
  - 28 (0.301) have N with very low loss in binders (< .2% average loss across all HLAs) for both HLA-I and HLA-II (left)
  - 40 (0.430) have N with very low loss in binders (< .2% average loss across all HLAs) for either HLA-I or HLA-II (right)

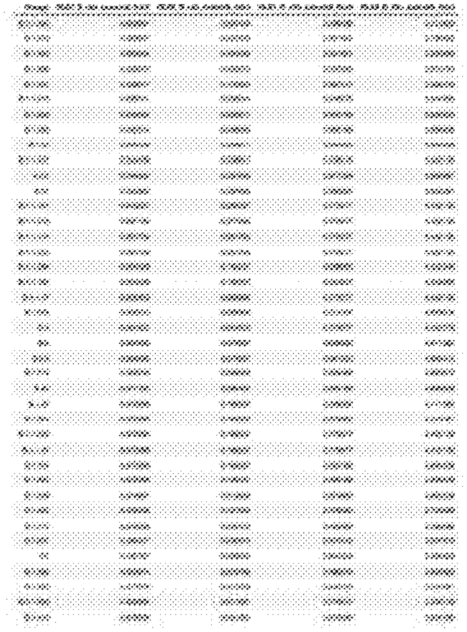

FIG. 63

Conclusions: Lineages with S in top 20% sum fraction of binders lost for HLA-I or HLA-II

- S + N vaccine may have an edge on the strains below that may be challenging for S only vaccines
- From the 141 lineages ranked in top 20% of binder loss across HLAs in S:
  - 47 (0.333) have N with very low loss in binders (< .2% average loss across all HLAs) for both HLA-I and HLA-II B.1.319, B.1.351, B.1.338, B.1.283, B.1.23, B.1.1.127, A.2.2, B.31, B.1.1.181, B.1.1.219, B.1.1.174, B.1.1.225, B.1.1.77, D.3, B.6, B.6.6, B.1.216, B.40, B.1.1.230, B.1.1.37, B.1.104, B.1.482, B.1.239, B.1.258.17, B.1.268, B.1.330, B.1.362, C.14, B.1.385, B.1.337, B.1.305, P.1, B.1.366, B.1.1.205, B.1.451, B.1.452, A.2, B.1.1.96, B.1.265, B.1.355, B.1.399, B.1.1.306, B.1.1.26, B.1.397, B.1.498, B.1.356, B.1.413

- 68 (0.482) have N with very low loss in binders (< .2% average loss across all HLAs) for either HLA-I or HLA-II B.1.1.285, B.1.319, B.1.349, B.1.306, B.1.351, B.1.1.216, B.1.338, B.1.283, B.1.23, B.1.1.127, A.2.2, B.31, B.1.1.181, B.1.1.219, B.1.1.174, B.1.1.225, B.1.1.284, B.1.1.162, B.1.1.77, B.1.525, D.3, B.6, B.6.6, B.1.216, B.40, B.1.37, B.1.334, B.1.1.230, B.1.1.37, B.1.104, B.1.482, B.1.239, B.1.453, B.1.213, B.1.207, B.1.258.17, B.1.390, B.1.268, B.1.483, B.1.330, B.1.362, C.14, B.1.385, B.1.1.130, B.1.337, B.1.305, P.1, B.1.433, B.1.366, B.1.1.205, B.1.451, B.1.1.192, B.1.452, A.2, B.1.1.96, B.1.265, B.1.526, B.1.152, B.1.355, B.1.399, B.1.1.306, B.1.1.10, B.1.1.26, B.1.397, B.1.498, B.1.356, B.1.1.131, B.1.413

FIG. 64

Change in HLA-I binder count at panHLA-I,II hotspots relative to ref. S protein Change in HLA-I binder count at panHLA-I,II hotspots relative to ref. S protein

SEQUENCE LISTING

```
<160> NUMBER OF SEQ ID NOS: 1

<210> SEQ ID NO 1
<211> LENGTH: 9
<212> TYPE: PRT
<213> ORGANISM: SARS CoV2
```

-continued

<400> SEQUENCE: 1

```
Ala Leu Ala Thr Phe Thr Val Asn Ile
1               5
```

HLA CLUSTERS, GLOBAL FREQUENCIES, AND BINDING ACROSS SARS-CoV-2 VARIATION

CROSS-REFERENCE TO RELATED APPLICATIONS

This application claims priority to U.S. Provisional Patent Application Ser. No. 63/148,609, filed Feb. 12, 2021, titled "HLA CLUSTERS, GLOBAL FREQUENCIES, AND BINDING ACROSS SARS-CoV-2 VARIATION", and U.S. Provisional Patent Application Ser. No. 63/195,660, filed Jun. 1, 2021, titled "HLA CLUSTERS, GLOBAL FREQUENCIES, AND BINDING ACROSS SARS-CoV-2 VARIATION". The contents of both applications are hereby incorporated by reference in their entirety for all purposes.

TECHNICAL FIELD

This disclosure relates generally to predicting binding affinity between epitopes and human leukocyte antigen (HLA) peptide or protein sequences, and more specifically to computer-based predictions used to determine pan-HLA binding of viral proteins.

REFERENCE TO SEQUENCE LISTING

This application contains a Sequence Listing in electronic format. The Sequence Listing file, titled 10077-2007700_Sequence_Listing.txt, was created on May 21, 2021, and is 445 bytes in size. The information in electronic format of the Sequence Listing is incorporated herein by reference in its entirety.

BACKGROUND

Since the emergence of severe acute respiratory syndrome coronavirus 2 (SARS-CoV-2), the novel coronavirus responsible for the coronavirus disease 2019 (COVID-19) global pandemic, medical researchers have focused on the rapid characterization of SARS-CoV-2 to determine possible target proteins or peptides for vaccine and therapeutic treatment development. This research is grounded in an understanding of the human immune system. At a high level, the HLA system or complex is a group of related proteins that are encoded by the major histocompatibility complex (MHC) gene complex in humans. These cell-surface proteins are responsible for the regulation of the immune system. HLAs corresponding to MHC class I (referred to herein as "HLA-I") present peptides from inside a cell. For example, if the cell is infected by a virus, the HLA system brings fragments of the virus to the surface of the cell so that the cell can be destroyed by the immune system. HLAs corresponding to MHC class II (referred to herein as "HLA-II") present antigens from outside of the cell to T-lymphocytes. These antigens stimulate the multiplication of T-helper cells (also called CD4+ T cells). CD4+ T cells recognize peptides presented on MHC-II molecules, which are found on antigen presenting cells. They play a major role in instigating and shaping adaptive immune responses, such as by stimulating antibody-producing B-cells to produce antibodies to that specific antigen. An epitope is the part of an antigen such as SARS-CoV-2 that is recognized by the immune system, specifically by antibodies, B cells, or T cells and is the specific piece of the antigen to which an antibody binds.

SARS-CoV-2 has a single-stranded, positive-sense, RNA genome of approximately 30 kilobases (kb), which includes open reading frames encoding nonstructural replicase polyproteins and structural proteins, namely, spike (S), envelope (E), membrane (M), and nucleocapsid (N). The positive-sense genome can act as messenger RNA and can be directly translated into viral proteins by a host cell's ribosomes.

Throughout 2020, early results from research efforts pointed to highest HLA-I/-II binding recognition from SARS-CoV-2 spike (S) and nucleocapsid (N) proteins.

Grifoni, Sidney, Zhang, Scheuermann, Peters, and Sette (bioRxiv, "Candidate targets for immune responses to 2019-Novel Coronavirus (nCoV): sequence homology- and bioinformatic-based predictions"; February 2020) observed that SARS-CoV-2 S and N proteins have the most candidate T & B cell epitopes. This research used reference "Wuhan-Hu-1" viral strain proteins and was based on conserved epitopes from SARS-CoV (the 2003 SARS virus) and SARS-CoV-2 predictions (determined using NetMHC4.0pan) across 12 HLA-I alleles. T-cell epitopes with high sequence identity to SARS-CoV were independently identified by both methods.

Nguyen, David, Maden, Wood, Weeder, Nellore, and Thomson (medRxiv, "Human leukocyte antigen susceptibility map for SARS-CoV-2"; March 2020) observed that genetic variability across the three MHC class I genes (HLA A, B, and C) may affect susceptibility to and severity of SARS-CoV-2. The authors executed an in silico analysis of viral peptide-MHC class I binding affinity across 145 HLA-A, -B, and -C genotypes for all SARS-CoV-2 peptides, and explored the potential for cross-protective immunity conferred by prior exposure to four common human coronaviruses. The analysis showed 48 highly conserved amino acid sequence spans across 34 distinct coronaviruses (ORF1ab, S, E, M, and N proteins), and 56 HLAs that had no affinity for conserved peptides. It also showed that the SARS-CoV-2 proteome is successfully sampled and presented by a diversity of HLA alleles. However, HLA-B*46:01 had the fewest predicted binding peptides for SARS-CoV-2, suggesting individuals with this allele may be particularly vulnerable to COVID-19, as they were previously shown to be for SARS-CoV. Conversely, HLA-A*02:02, HLA-B*15:03, and HLA-C*12:03 showed the greatest capacity to present highly conserved SARS-CoV-2 peptides that are shared among common human coronaviruses, suggesting it could enable cross-protective T-cell based immunity. Global distributions of HLA types were also reported with discussion on potential epidemiological ramifications in the setting of the COVID-19 pandemic.

Grifoni, Weiskopf, Ramirez, Mateus, Dan, Moderbacher, Rawlings, Sutherland, Premkumar, Jadi, Marrama, de Silva, Frazier, Carlin, Greenbaum, Peters, Krammer, Smith, Crotty, and Sette ("Targets of T Cell Responses to SARS-CoV-2 Coronavirus in Humans with COVID-19 Disease and Unexposed Individuals"; May 2020) used HLA-I and II predicted peptide "megapools" to identify circulating SARS-CoV-2-specific $CD8^+$ and $CD4^+$ T cells in ~70% and 100% of COVID-19 convalescent patients, respectively. $CD4^+$ T cell responses to S proteins, the main target of most vaccine efforts, were robust and correlated with the magnitude of the anti-SARS-CoV-2 IgG and IgA titers. The M, S, and N proteins each accounted for 11%-27% of the total $CD4^+$ response, with additional responses commonly targeting nsp3, nsp4, ORF3a, and ORFS, among others. For $CD8^+$ T cells, S and M proteins were recognized, with at least eight SARS-CoV-2 ORFs targeted. Additionally, SARS-CoV-2-reactive $CD4^+$ T cells were detected in ~40%-60% of unexposed individuals, suggesting cross-reactive T cell recognition between circulating "common cold" coronaviruses and SARS-CoV-2.

Yarmarkovich, Warrington, Farrel, and Maris (Cell Reports Medicine, "Identification of SARS-CoV-2 Vaccine Epitopes Predicted to Induce Long-Term Population-Scale Immunity"; June 2020) proposed a SARS-CoV-2 vaccine design concept based on identification of highly conserved regions of the viral genome and newly acquired adaptations, both predicted to generate epitopes presented on MHC class I and II across the vast majority of the human population. The study prioritized genomic regions that generate highly dissimilar peptides from the human proteome and are also predicted to produce B cell epitopes. The researchers proposed sixty-five 33-mer peptide sequences predicted to drive long-term immunity for most people, a subset of which could be tested using DNA or mRNA delivery strategies. These included peptides that are contained within evolutionarily divergent regions of the spike (S) protein reported to increase infectivity through increased binding to the ACE2 receptor and within a newly evolved furin cleavage site thought to increase membrane fusion.

As a backdrop to these efforts, Recurrent Neural Networks (RNNs) have been used successfully in recent years for many tasks involving sequential data where the RNN must find connections between long input and output sequences, such as for binding predictions between full peptide and HLA protein sequences. Attention mechanisms that enable improved performance in many tasks are an integral part of modern RNN networks. An attention mechanism can allow the RNN to focus on certain parts of an input sequence when predicting a certain part of an output sequence, enabling easier learning and higher quality predictions.

So far, however, current techniques have yielded limited information in terms of how HLA-I/II binding of SARS-CoV-2 proteins can vary across viral strains and world populations. Particularly, current techniques have not provided sufficient insight into the nexus between HLA-I/II clusters, global frequencies, and binding across SARS-CoV-2 variation. For example, vaccine researchers have yet to find effective techniques that minimize the chances of missing clusters of uniquely functioning HLAs in the quest for SARS-CoV-2 vaccines or therapeutic treatments. Without techniques that yield such information, it has been difficult for medical researchers to achieve the validation and implementation of vaccine or therapeutic treatment concepts that specifically target vulnerabilities of SARS-CoV-2 and engage a robust adaptive immune response in the vast majority of the world population.

SUMMARY

Systems, methods, and articles of manufacture for determining pan-HLA binding of viral proteins are described herein. The pan-HLA binding determinations of the various embodiments may enable medical researchers to minimize the chances of missing clusters of uniquely functioning HLAs in the quest for vaccines or therapeutic treatments that are effective across the world population. Such vaccines or therapeutic treatments may be useful in the quest to mitigate the effects of viruses that spread globally, such as SARS-CoV-2.

In one embodiment, a viral protein encoded into variable-length peptides is obtained. Each of the encoded variable-length peptides may be, for example, between 8-15 amino acids in length. A classifier model trained to process encoded variable-length peptides is configured such that, independently per HLA, the classifier model is operable to determine at least one of (a) an average binding prediction of overlapping peptides at each position of the viral protein, (b) a maximum value of a binding prediction of overlapping peptides at each position of the viral protein, (c) a standard deviation of a binding prediction of overlapping peptides at each position of the viral protein, and (d) a combination of one or more of (a)-(c). The classifier model may be trained using encoded variable-length peptides corresponding to training proteins and encoded variable-length proteins corresponding to one or more HLA alleles in the human population. A classification engine is configured to use the classifier model to determine average binding predictions of overlapping peptides at each position of the viral protein independently for each of a plurality of test HLAs comprising HLA-I and HLA-II functional groupings, where determining the average binding predictions includes classifying a peptide as a binder when an average binding prediction corresponding to the peptide satisfies a binding prediction threshold. The binding prediction value threshold may be 0.5. Peptides for which the threshold falls within a multiple of the standard deviation from the average binding prediction value may be classified as ambiguous.

In some embodiments, a plurality of test HLAs encoded into variable-length proteins may be obtained, where the plurality of test HLAs comprises HLA-I and HLA-II functional groupings. The HLA-I functional grouping may comprise HLA-I protein sequences, and the HLA-II functional grouping may comprise HLA-II alpha chain and beta chain sequences. The encoded variable-length peptides corresponding to the viral protein and the variable-length proteins corresponding to the plurality of test HLAs may be processed using the classifier model such that, independently per test HLA, the classifier model is operable to determine an average binding prediction of overlapping peptides at each position of the viral protein. Independently per test HLA, average binding predictions may be mapped in aggregate to locations along the test viral protein such that peptide-HLA interaction is indicated; nearest max locations may be determined for the average binding predictions using a sliding window having a fixed length; top max regions may be determined by selecting the nearest max locations having average binding predictions within a top percentage of values; peptides classified as binders that overlap the top max regions may be selected; and a pan-HLA max region may be determined, where the determining may include setting unselected locations to zero, calculating a mean along an HLA axis of the average binding prediction, and selecting pan-HLA maxima within a top percentage of values based on the mean. The selected peptides classified as binders may be filtered independently for each of the HLA-I and HLA-II functional groupings to identify candidate peptides that overlap the top max regions based on an aggregate of the pan-HLA max regions, and one or more of the candidate peptides may be included in an mRNA-based vaccine or therapeutic treatment for a patient. At least one of the candidate peptides may be selected for inclusion in the mRNA-based vaccine or therapeutic treatment for the patient based on HLA allele frequencies in worldwide populations, and the plurality of test HLAs may correspond to HLA allele frequencies in worldwide populations.

In some embodiments, the viral protein may comprise a SARS-CoV-2 protein variant such as a SARS-CoV-2 nucleocapsid (N) protein variant, spike (S) protein variant, membrane (M) protein variant, or envelope (E) protein variant and the mRNA-based vaccine or therapeutic treatment may be capable of treating a patient having SARS-CoV-2.

In some embodiments, the mapping of peptide-HLA interaction may include indicating locations signifying co-occurrences of peptide attention and HLA attention.

In some embodiments, the fixed length of the sliding window may be based on a dominant peptide length of the variable-length peptides, e.g., a dominant peptide length equal to 9-mers or 15-mers.

In some embodiments, the top max regions may be determined by selecting the nearest max locations having average binding predictions within a top 10% of values or within a top 25% of values, and the pan-HLA max region may be determined by selecting pan-HLA maxima within a top 25% of values.

Various objects, features, aspects and advantages of the inventive subject matter will become more apparent from the following specification, along with the accompanying drawings in which like numerals represent like components.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 19 illustrates a block diagram of an exemplary client-server relationship that can be used for implementing one or more aspects of the various embodiments.

FIG. 21 illustrates performance validation data for a trained Recurrent Neural Net with Attention & MHC-SEQ in accordance with an embodiment in comparison with NetMHCpan4.1.

FIG. 24 illustrates graphical representations of learned HLA functional similarity groupings.

FIG. 25 illustrates a method of selection of HLA-I and HLA-II clusters in accordance with an embodiment.

FIG. 32 illustrates a listing of SARS-CoV-2 lineages of interest.

FIG. 45 illustrates SARS-CoV-2 S variants with the most relative binder loss (vs. a reference) across HLA-I alleles in accordance with an embodiment.

FIG. 50 illustrates SARS-CoV-2 S variants with the most relative binder loss (vs. a reference) across HLA-II alleles in accordance with an embodiment.

FIG. 53 illustrates change in HLA-I binder count at pan-HLA-I, II hotspots relative to a reference SARS-CoV-2 N protein.

FIG. 54 illustrates SARS-CoV-2 N variants with the most relative binder loss (vs. a reference) across HLA-I alleles.

FIG. 56 illustrates SARS-CoV-2 N variants with most relative binder loss (vs. a reference) across HLA-II alleles.

FIG. 57 illustrates a lineage of interest ranking of worst-case binder loss relative to all observed SARS-CoV-2 S, N protein variants.

FIG. 58 illustrates binder loss rankings for all lineages with S HLA-I or HLA-II binder loss fraction (vs. a reference SARS-CoV-2 S protein) in the top 2%.

FIG. 59 illustrates performance validation data conclusions regarding the SARS-CoV-2 B.1.351: South Africa lineage.

FIG. 60 illustrates performance validation data conclusions regarding SARS-CoV-2 lineages of interest.

FIG. 61 illustrates performance validation data conclusions regarding SARS-CoV-2 lineages with S in the top 2% sum fraction of binders lost for HLA-I or HLA-II.

FIG. 62 illustrates performance validation data conclusions regarding SARS-CoV-2 lineages with S in the top 5% sum fraction of binders lost for HLA-I or HLA-II.

FIG. 63 illustrates performance validation data conclusions regarding SARS-CoV-2 lineages with S in the top 10% sum fraction of binders lost for HLA-I or HLA-II.

FIG. 64 illustrates performance validation data conclusions regarding SARS-CoV-2 lineages with S in the top 20% sum fraction of binders lost for HLA-I or HLA-II.

Figure 1:
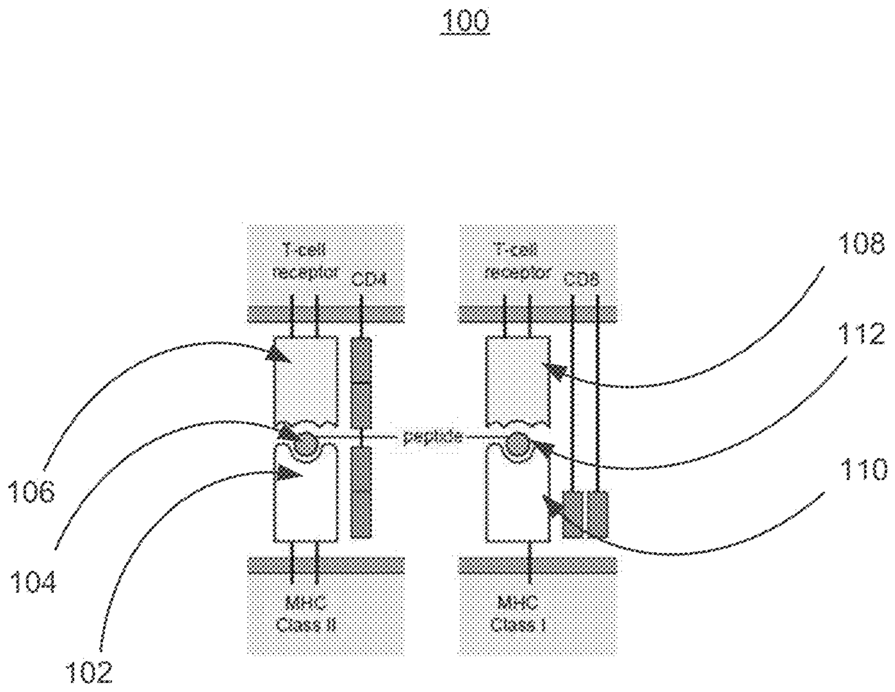
FIG. 1 illustrates a visual representation of MHC molecules binding with peptides at a surface of a nucleated cell in accordance with an embodiment.

While the invention is described with reference to the above drawings, the drawings are intended to be illustrative, and other embodiments are consistent with the spirit, and within the scope, of the invention.

DETAILED DESCRIPTION

The various embodiments will now be described more fully hereinafter with reference to the accompanying drawings, which form a part hereof, and which show, by way of illustration, specific examples of practicing the embodiments. This specification may, however, be embodied in many different forms and should not be construed as being limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

Throughout the specification and claims, the following terms take the meanings explicitly associated herein, unless the context clearly dictates otherwise:

The phrase "in one embodiment" as used herein does not necessarily refer to the same embodiment, though it may. Thus, as described below, various embodiments of the invention may be readily combined, without departing from the scope or spirit of the invention.

As used herein, the term "or" is an inclusive "or" operator and is equivalent to the term "and/or," unless the context clearly dictates otherwise.

The term "based on" is not exclusive and allows for being based on additional factors not described, unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of a networked environment where two or more components or devices are able to exchange data, the terms "coupled to" and "coupled with" are also used to mean "communicatively coupled with", possibly via one or more intermediary devices.

In addition, throughout the specification, the meaning of "a", "an", and "the" includes plural references, and the meaning of "in" includes "in" and "on".

Although some of the various embodiments presented herein constitute a single combination of inventive elements, it should be appreciated that the inventive subject matter is considered to include all possible combinations of the disclosed elements. As such, if one embodiment comprises elements A, B, and C, and another embodiment comprises elements B and D, then the inventive subject matter is also considered to include other remaining combinations of A, B, C, or D, even if not explicitly discussed herein. Further, the transitional term “comprising” means to have as parts or members, or to be those parts or members. As used herein, the transitional term “comprising” is inclusive or open-ended and does not exclude additional, unrecited elements or method steps.

Throughout the following discussion, numerous references will be made regarding servers, services, interfaces, engines, modules, clients, peers, portals, platforms, or other systems formed from computing devices. It should be appreciated that the use of such terms is deemed to represent one or more computing devices having at least one processor (e.g., ASIC, FPGA, DSP, x86, ARM, ColdFire, GPU, multi-core processors, etc.) configured to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable medium storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, a circuit-switched network, the Internet, LAN, WAN, VPN, or other type of network.

As used in the description herein and throughout the claims that follow, when a system, engine, server, device, module, or other computing element is described as being configured to perform or execute functions on data in a memory, the meaning of “configured to” or “programmed to” is defined as one or more processors or cores of the computing element being programmed by a set of software instructions stored in the memory of the computing element to execute the set of functions on target data or data objects stored in the memory.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

The focus of the disclosed inventive subject matter is to enable construction or configuration of a computing device to operate on vast quantities of digital data, beyond the capabilities of a human for purposes including determining pan-HLA binding of viral proteins.

One should appreciate that the disclosed techniques provide many advantageous technical effects including improving the scope, accuracy, compactness, efficiency, and speed of determining pan-HLA binding of viral proteins. It should also be appreciated that the following specification is not intended as an extensive overview, and as such, concepts may be simplified in the interests of clarity and brevity.

In addition to the terms above, the following technical terms are used throughout the specification and claims.

The human leukocyte antigen (HLA) system or complex is a group of related proteins that are encoded by the major histocompatibility complex (MHC) gene complex in humans. These cell-surface proteins are responsible for the regulation of the immune system.

An epitope, also known as antigenic determinant, is the part of an antigen that is recognized by the immune system, specifically by antibodies, B cells, or T cells. For example, the epitope is the specific piece of the antigen to which an antibody binds.

An allele, also called allelomorph, is any one of two or more genes that may occur alternatively at a given site (locus) on a chromosome. Alleles may occur in pairs, or there may be multiple alleles affecting the expression (phenotype) of a particular trait.

CD8+ cytotoxic T cells are a subtype of T cells and the main effectors of cell-mediated adaptive immune responses. They kill aberrant cells, such as cancer cells, infected cells (particularly with viruses), or cells that are damaged in another way.

CD4+ T cells recognize peptides presented on MHC class II molecules, which are found on antigen presenting cells. They play a significant role in instigating and shaping adaptive immune responses.

Peptides are short strings of amino acids, typically comprising 2-50 amino acids. Amino acids are also the building blocks of proteins, but proteins contain more. Peptides may be easier for the body to absorb than proteins because they are smaller and more broken down than proteins.

HLAs corresponding to MHC class I (A, B, and C), all of which are the HLA-I group, present peptides from inside the cell. For example, if the cell is infected by a virus, the HLA system brings fragments of the virus to the surface of the cell so that the cell can be destroyed by the immune system.

HLAs corresponding to MHC class II (DP, DM, DO, DQ, and DR) present antigens from outside of the cell to T-lymphocytes. These antigens stimulate the multiplication of T-helper cells (CD4+ T cells), which in turn stimulate antibody-producing B-cells to produce antibodies specific to that antigen. Self-antigens are suppressed by regulatory T cells.

The various embodiments provide for a classifier model to be trained to determine pan-HLA binding of viral proteins based on a limited set of training HLA data, e.g., HLA data pertaining to only one HLA allele or a subset of HLA alleles. Once the classifier model is trained, a classification engine configured to use the classifier model, as described herein, can overcome problems encountered in the development of widely applicable vaccines or therapeutic treatments for viruses when limited or no binding data is available for many HLA alleles present across the worldwide human population. Thus, the limited information currently available on how HLA-I/II binding of SARS-CoV-2 proteins can vary across viral strains and world populations can be addressed by the various techniques described herein to minimize the chances of missing clusters of uniquely functioning HLAs in the quest for SARS-CoV-2 vaccines or treatments.

FIG. 1 illustrates a visual representation of MHC molecules binding with peptides at a surface of a nucleated cell in accordance with an embodiment. Representation 100 illustrates an MHC class II molecule 102 that presents a stably bound peptide 104 that is essential for overall immune function. MHC Class II molecule 102 mainly interacts with immune cells, such as helper (CD4) T-cell 106. For example, peptide 104 (e.g., an antigen) may regulate how CD4 T-cell 106 responds to an infection. In general, stable peptide binding is essential to prevent detachment and degradation of a peptide, which could occur without secure attachment to the MHC Class II molecule 102. Such detachment and degradation would prevent T-cell recognition of the antigen, T-cell recruitment, and a proper immune response. CD4 T-cells, so named because they express the CD4 glycoprotein at their surface, are useful in the antigenic activation of CD8 T-cells, such as CD8 T-cell 108. Therefore, the activation of CD4 T-cells can be beneficial to the action of CD8 T-cells.

CD8 T-cell 108 is a cytotoxic T-cell that expresses the CD8 glycoprotein at its surface. Cytotoxic T-cells (also known as TC cells, CTLs, T-killer cells, killer T-cells) destroy virus-infected cells and tumor cells. These cells recognize virus-infected or tumor cell targets by binding to fragments of non-self proteins (peptide antigens) that are between 6-20 amino acids in length (though generally they are 8-15 amino acids in length) and presented by major histocompatibility complex (MHC) class I molecules, such as MHC class I molecule 110. MHC class I molecules are present on the surface of all nucleated cells in humans. Their function is to display intracellular peptide antigens, e.g., peptide 112, to cytotoxic T-cells, thereby triggering an immediate response from the immune system against the peptide antigen displayed. An understanding what kinds of peptides bind well with what kinds of MHC class I molecules (i.e., which peptides are best for activating a cytotoxic T-cell response) is critical for current immunology research, particularly since across the worldwide human population each HLA allele of an MHC compound has different properties. The embodiments herein improve the operation of neural network-based MHC-peptide binding affinity prediction models by allowing for a determination of pan-HLA bindings across viral proteins, such as SARS-CoV-2 variants.

Figure 2:
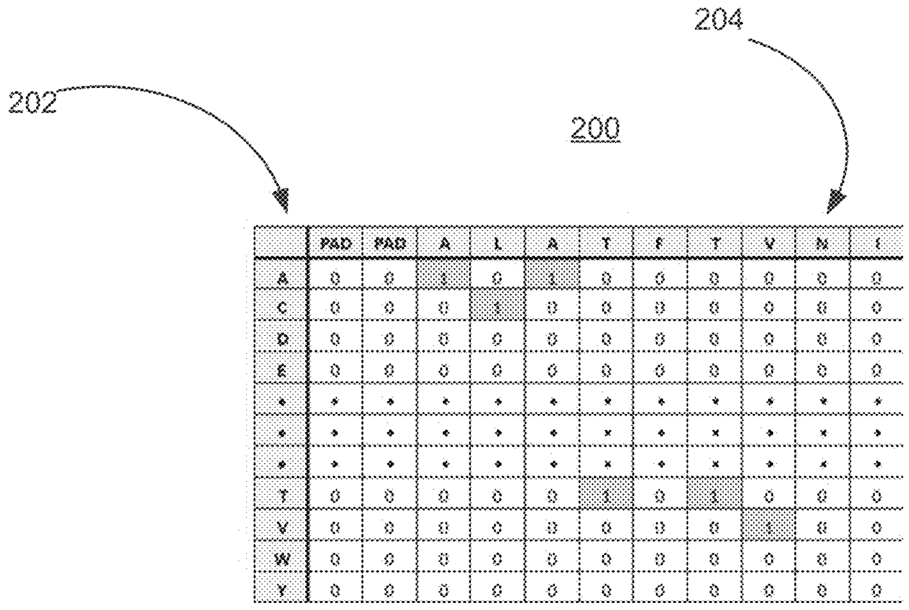
FIG. 2 illustrates an example of an encoded peptide sequence in accordance with an embodiment.

FIG. 2 illustrates an example of an encoded peptide sequence in accordance with an embodiment. Matrix 200 represents a one-hot encoding of a 9-mer protein/peptide sequence "ALATFTVNI" (SEQ ID NO. 1), where the single letter codes are used to represent the 20 naturally occurring amino acids. In some embodiments, matrix 200 may include padding values (i.e., one or more '0' or null values) in the encoded peptide sequence to match a fixed-length input of a neural network. For example, the peptide sequence may be encoded to include a front pad 202 and a back pad 204 that are each 2-mers (or bits) in length as shown. However, it will be noted that various other combinations of front padding and back padding are possible based on the variable lengths of the peptide sequences and the fixed-length input of a neural network. For example, in addition to the one-hot encoded (--ALATFTVNI--) (SEQ ID NO. 1) sequence shown in matrix 200, the one-hot encoded peptide sequence also may be front padded or back padded using one or more '0' or null values as (ALATFTVNI----), (-ALATFTVNI---), (---ALATFTVNI-), and (----ALATFTVNI) to accommodate, for example, a 13-mer fixed length input. Padding is not necessary in embodiments that use RNN architectures for binding prediction but may be used in some architectures such as convolutional neural networks (CNN) or neural network models consisting only of a hierarchy of fully connected layers.

HLA protein sequences are encoded for input into a neural network model following the exact same procedure as peptide encodings.

Figure 3:
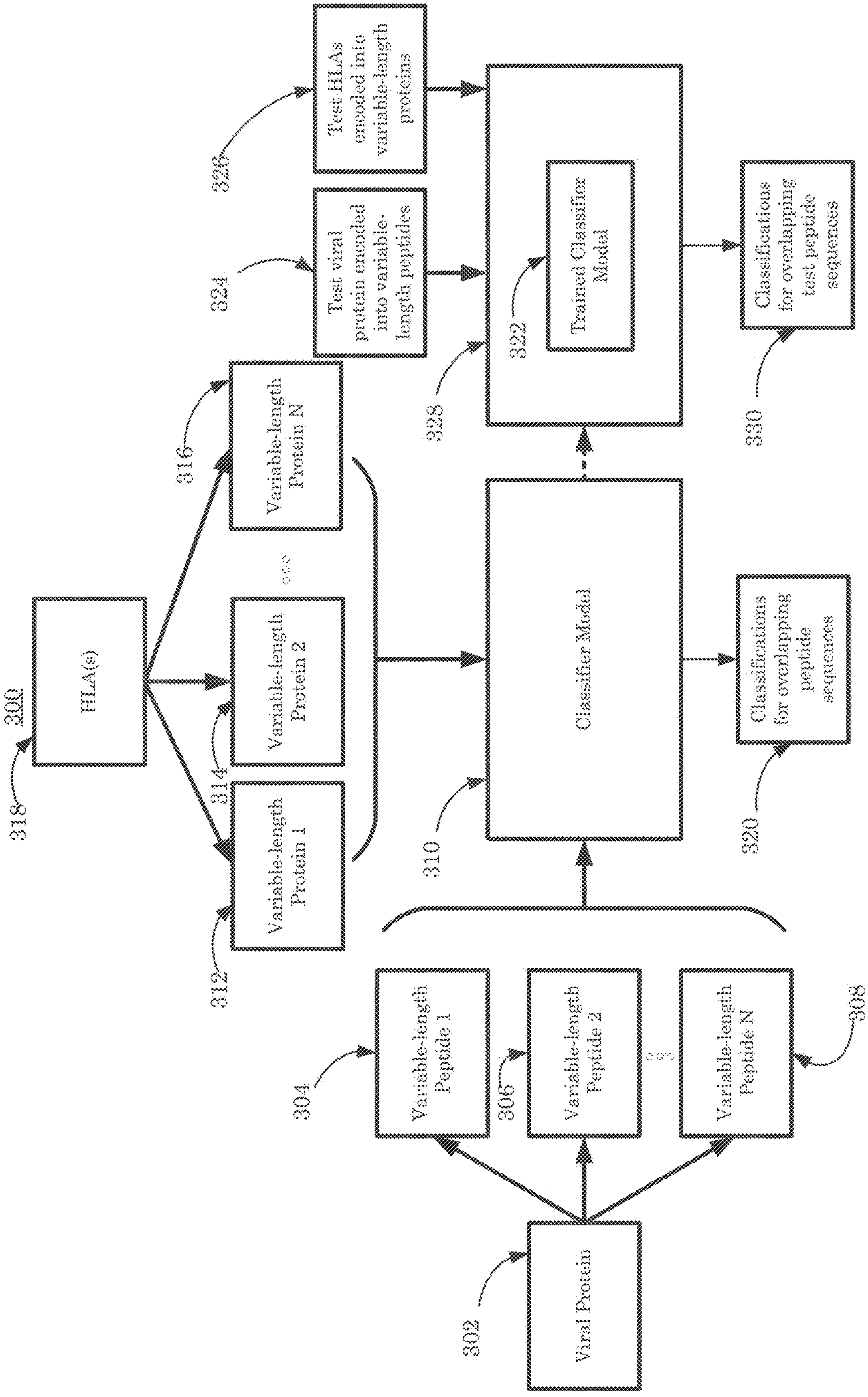
FIG. 3 illustrates a flow diagram of example operations for training a recurrent neural network to determine pan-HLA binding of viral proteins in accordance with an embodiment.

FIG. 3 illustrates a flow diagram of example operations for training a recurrent neural network to determine pan-HLA binding of viral proteins in accordance with an embodiment. In flow diagram 300, training viral protein 302 is encoded into variable-length training peptide sequences 1 to N 304, 306, and 308. Each of the encoded variable-length peptides may be, for example, between 8-15 amino acids in length, and one-hot encoded in a manner as shown in matrix 200 above.

Using encoded variable-length peptides sequences 1 to N 304, 306, and 308 combined with encoded variable-length protein sequences 1 to N 312, 314, and 316 corresponding to one or more HLA alleles 318 in the human population, neural network-based classifier model 310 is trained to predict pan-allele MHC-peptide binding affinity for HLA I and HLA II alpha and beta chain sequences. Classifier model 310 may comprise one or more recurrent neural networks configured, as described in further detail below, to determine, independently per HLA, an average binding prediction 320 of overlapping peptides at each position of the viral protein. In some embodiments, classifier model 310 may also be configured to determine a maximum value of a binding prediction of overlapping peptides at each position of the viral protein, a standard deviation of a binding prediction of overlapping peptides at each position of the viral protein, and/or a combination of one or more the above. The classifier is trained to predict peptide binding to HLA molecules based on an extensive database of empirical binding and non-binding peptide measurements for a large collection of HLAs.

Once the training is completed, the trained classifier model 322 can be configured to receive encoded variable-length peptides sequences 324 corresponding to a test viral protein and encoded variable-length protein sequences 326 corresponding to a plurality of HLAs in the human population. In an embodiment, a classification engine 328 may be configured to use the trained classifier model 322 to determine average binding predictions 330 of overlapping peptides at each position of the viral protein independently for each of a plurality of test HLAs comprising HLA-I and HLA-II functional groupings, where determining the average binding predictions includes classifying a peptide as a binder when an average binding prediction corresponding to the peptide satisfies a binding prediction threshold. The binding prediction value threshold may be 0.5. Peptides for which the threshold falls within a multiple of the standard deviation from the average binding prediction value may be classified as ambiguous.

Figure 4:
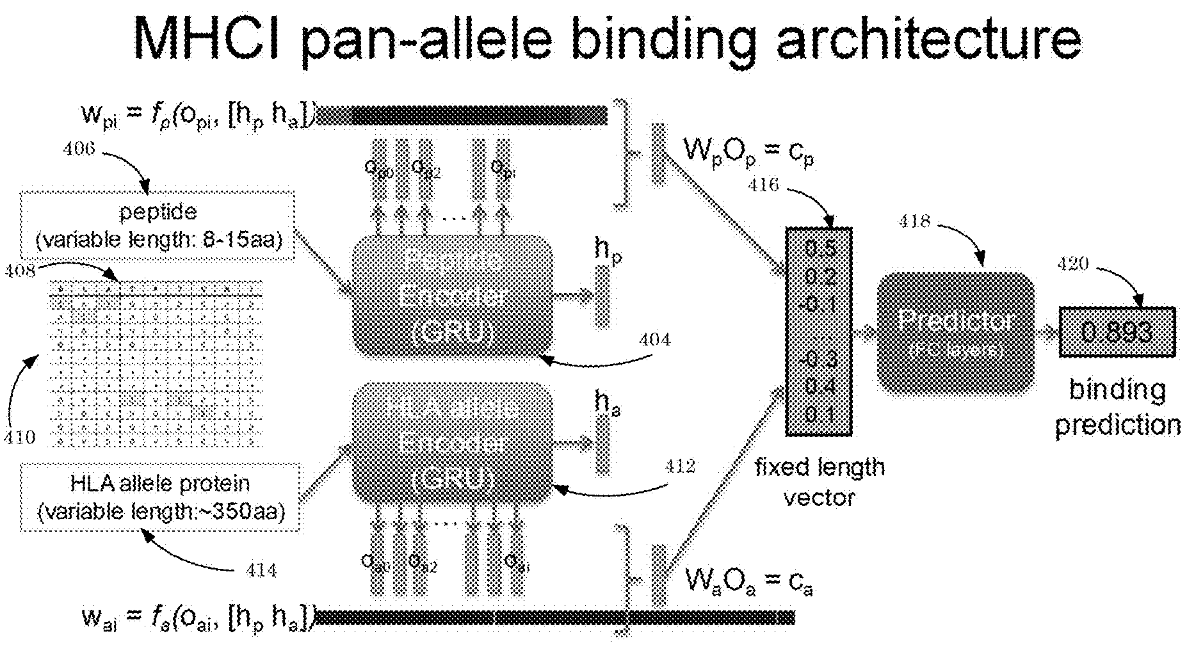
FIG. 4 illustrates an overview diagram of an MHC I pan-allele binding neural network architecture in accordance with an embodiment.

FIG. 4 illustrates an overview diagram of an MHC I pan-allele binding neural network architecture in accordance with an embodiment. Neural network architecture 400 comprises a recurrent neural network for determining average binding predictions of overlapping peptides at each position of a viral protein independently for each of a plurality of test HLAs comprising HLA-I functional groupings. In an embodiment, neural network architecture 400 comprises a gated recurrent unit (GRU) peptide encoder 404 including an attention mechanism configured to encode input variable-length peptide sequences 406, e.g., peptides between 8-15aa in length. For example, input variable-length peptide sequence 406 is illustrated both as a raw sequence 408 with letter codes ("ALATFTVNI") (SEQ ID NO. 1) representing the naturally occurring amino acids, and as a flattened one-hot encoded input tensor 410, in which the legal combinations of values are only those with a single high ("1") bit while the other values are low ("0"). Neural network architecture 400 further comprises GRU HLA-I allele encoder 412 including an attention mechanism configured to encode an input variable-length protein sequence 414 (e.g., ~350aa in length) corresponding to an HLA-I protein sequence.

For each of the variable-length peptides 406 and variable-length proteins 414 encoded by the GRU peptide encoder 404 and GRU HLA-I allele encoder 412, respectively, a fixed-length vector 416 is generated for input to one or more fully connected layers 418. The one or more fully connected layers 418, comprising a plurality of hidden neurons (nodes), may follow a hierarchical structure (not shown) to perform a classification on the features extracted from fixed length vector 416. As such, the fully connected layers 418 are configured to receive input fixed-length vector 416 and generate output values 420, which represent average binding predictions of overlapping peptides at each position of the viral protein. In exemplary embodiments, the fully connected layers 418 are further configured to label uncertain binding predictions as being ambiguous. Classification of binding predictions as ambiguous may be achieved by identifying when the binding classification threshold is within a multiple of the standard deviation of the mean prediction value from an ensemble of trained neural networks.

In an embodiment, a classification engine may be configured to train a classifier model comprising neural network architecture 400 using encoded variable-length peptides corresponding to the training proteins and encoded variable-length proteins corresponding to each of the plurality of training HLAs. For example, an output value 420 may be compared to a known labeled value (e.g., a known MHC-peptide binding affinity or binary binding value corresponding to the input encoded peptide sequence) to determine a loss or error factor (e.g., using a loss function) that can be used to determine parameter updates (e.g., apportion some derivative of the loss to incrementally adjust each of the weight values) within the fully connected layers 418 and improve the rate of learning and final accuracy of neural network architecture 400.

As described above, classifier model comprising neural network architecture 400 may be trained to predict MHC-peptide binding by converting each raw training peptide sequence into a set of training peptide sequences including each possible front padded and back padded iteration of the training peptide sequence when the training peptide sequence is padded to be equal in length to a fixed length input of a neural network.

While the neural network architecture illustrated in FIG. 4 is exemplary for implementing the embodiments herein, one skilled in the art will appreciate that various other neural network architectures (e.g., densely connected convolutional networks and Recurrent Neural Networks (RNNs) such as Long Short-Term Memory Units (LSTMs), and additional Gated Recurrent Units (GRUs)) and additions (such as attention mechanisms) may be utilized. As such, neural network architecture 400 should not be construed as being strictly limited to the embodiments described herein.

Figure 5:
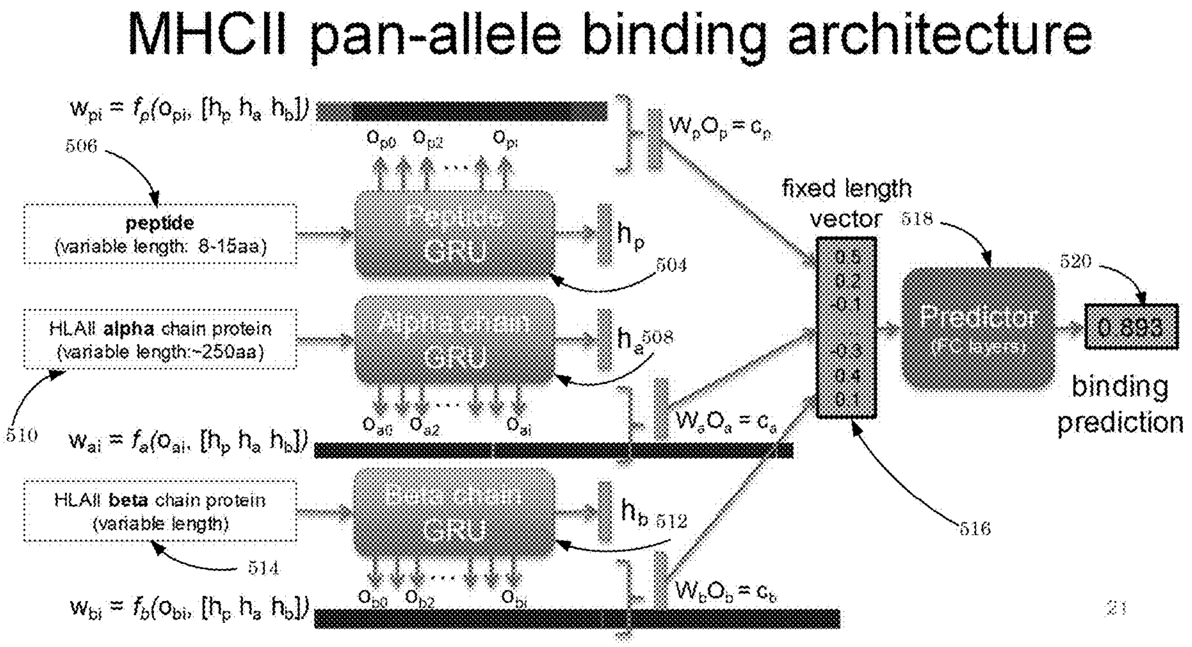
FIG. 5 illustrates an overview diagram of an MHC II pan-allele binding neural network architecture in accordance with an embodiment.

FIG. 5 illustrates an overview diagram of an MHC II pan-allele binding neural network architecture in accordance with an embodiment. Neural network architecture 500 comprises a recurrent neural network for predicting peptide-MHC binding that can be applied in a sliding window fashion to compute an average binding prediction of overlapping peptides at each position of a viral protein independently for each of a plurality of test HLAs comprising HLA-II alpha and beta functional groupings. In an embodiment, neural network architecture 500 comprises a gated recurrent unit (GRU) peptide encoder 504 including an attention mechanism configured to encode input variable-length peptide sequences 506, e.g., peptides between 8-15aa in length such as the peptide sequence "ALATFTVNI" (SEQ ID NO. 1) represented in one-hot code. Neural network architecture 500 further comprises GRU HLA-II alpha chain encoder 508 including an attention mechanism configured to encode an input variable-length protein sequence 510 (e.g., 250aa in length) corresponding to an HLA-II alpha chain protein sequence. GRU HLA-II beta chain encoder 512 including an attention mechanism is configured to encode an input variable-length protein sequence 514 (e.g., ~250aa in length) corresponding to an HLA-II beta chain protein sequence.

For each of the variable-length peptides 506 and variable-length proteins 510 and 514 encoded by the GRU peptide encoder 504, GRU HLA-II alpha chain encoder 508, and GRU HLA-II beta chain encoder 512, respectively, a fixed-length vector 516 is generated for input to one or more fully connected layers 518. The one or more fully connected layers 518, comprising a plurality of hidden neurons (nodes), may follow a hierarchical structure (not shown) to perform a classification on the features extracted from fixed length vector 516. As such, the fully connected layers 518 are configured to receive input fixed-length vector 516 and generate output values 520, which represent binding predictions of individual peptides that may be combined to obtain average binding predictions of overlapping peptides at each position of the viral protein. In exemplary embodiments, an ensemble of multiple trained neural networks with different random seeds, with the same or varying architectures, may be applied for each prediction and the variance of their prediction values can be used to label uncertain binding predictions as being ambiguous.

In an embodiment, a classification engine may be configured to train a classifier model comprising neural network architecture 500 using encoded variable-length peptides corresponding to the training viral protein and encoded variable-length proteins corresponding to each of the plurality of training HLAs. For example, an output value 520 may be compared to a known labeled value (e.g., a known MHC-peptide binding affinity value corresponding to the input encoded peptide sequence) to determine a loss or error factor (e.g., using a loss function) that can be used to determine parameter updates (e.g., apportion some derivative of the loss to incrementally adjust each of the weight values) within the fully connected layers 518 and improve the rate of learning and final accuracy of neural network architecture 500.

While the neural network architecture illustrated in FIG. 5 is exemplary for implementing the embodiments herein, one skilled in the art will appreciate that various other neural network architectures (e.g., densely connected convolutional networks and Recurrent Neural Networks (RNNs) such as Long Short-Term Memory Units (LSTMs), and additional Gated Recurrent Units (GRUs)) and additions (such as attention mechanisms) may be utilized. As such, neural network 500 should not be construed as being strictly limited to the embodiments described herein.

Figure 6:
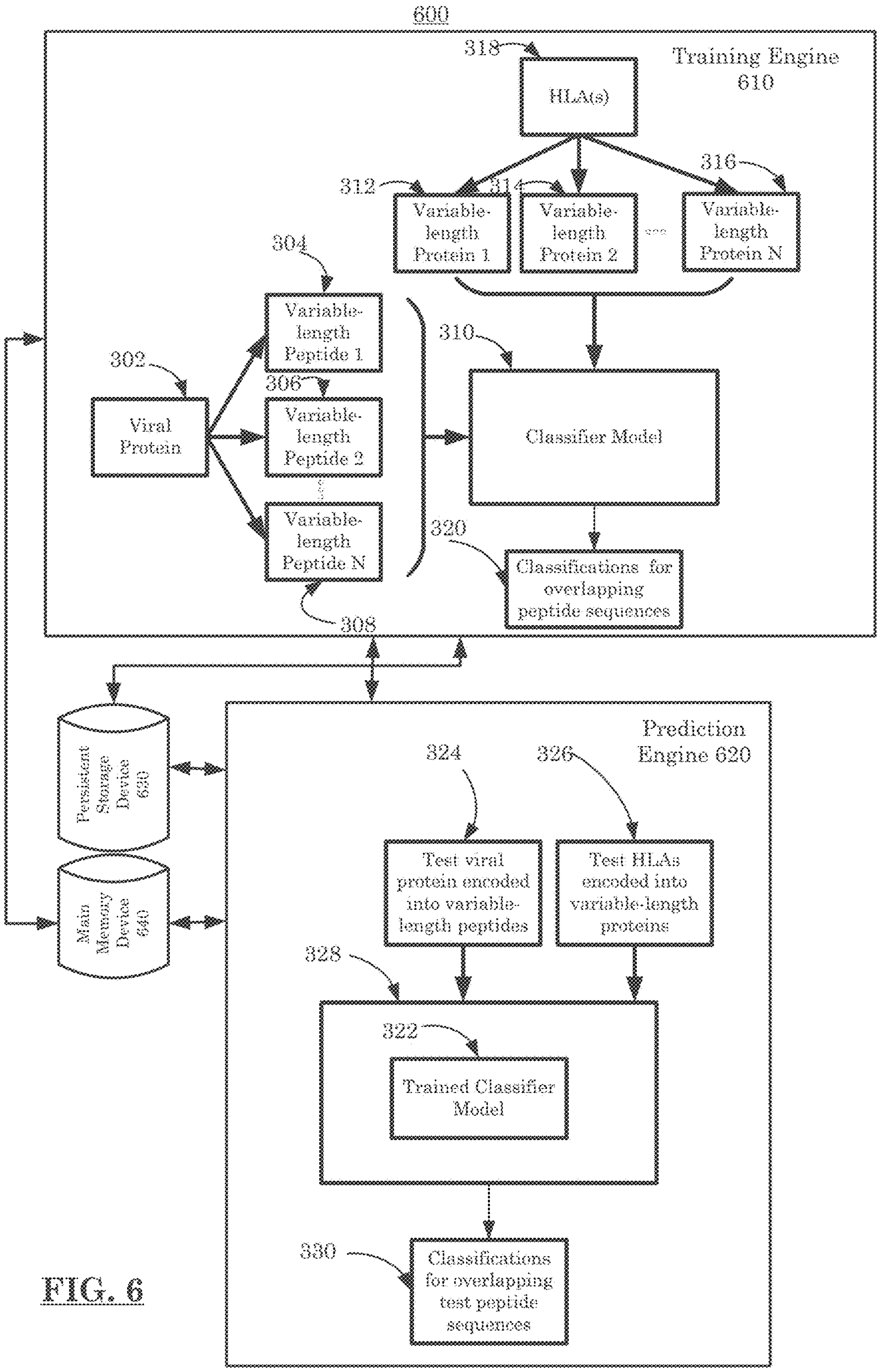
FIG. 6 illustrates a block diagram of a system for determining pan-HLA binding of viral proteins in accordance with an embodiment.

FIG. 6 illustrates a block diagram of a system for determining pan-HLA binding of viral proteins in accordance with an embodiment. In block diagram 600, elements for determining pan-HLA binding of encoded variable-length peptides corresponding to a viral protein include a training engine 610, a prediction engine 620, a persistent storage device 630, and a main memory device 640. In an embodiment, training engine 610 may be configured to obtain training viral protein 302 encoded into variable-length training peptide sequences 1 to N 304, 306, and 308 from either one or both of persistent storage device 630 and main memory device 640.

Training engine 610 may then configure and train neural network-based classifier model 310, using encoded variable-length peptides sequences 1 to N 304, 306, and 308 and encoded variable-length protein sequences 1 to N 312, 314, and 316 corresponding to one or more HLA alleles 318 in the human population, to predict pan-allele MHC-peptide binding affinity for HLA I and HLA II alpha and beta chain sequences. For example, training engine 610 may configure classifier model 310 to determine, independently per HLA, an average binding prediction 320 of overlapping peptides at each position of the viral protein. In some embodiments, training engine 610 may also configure classifier model 310 to determine a maximum value of a binding prediction of overlapping peptides at each position of the viral protein, a standard deviation of a binding prediction of overlapping peptides at each position of the viral protein, and/or a combination of one or more the above.

Training engine 610 may also configure prediction engine 620 to receive encoded variable-length peptides sequences 324 corresponding to a test viral protein and encoded variable-length protein sequences 326 corresponding to a plurality of HLAs in the human population and use the trained classifier model 322 to determine pan-HLA binding of encoded variable-length peptides corresponding to a viral protein. In an embodiment, prediction engine 620 may configure classification engine 328 to use the trained classifier model 322 to determine average binding predictions 330 of overlapping peptides at each position of the viral protein independently for each of a plurality of test HLAs comprising HLA-I and HLA-II functional groupings, where determining the average binding predictions includes classifying a peptide as a binder when an average binding prediction corresponding to the peptide satisfies a binding value threshold. The average binding predictions 330 of overlapping peptides may be stored in either one or both of persistent storage device 630 and main memory device 640.

However, it should be noted that the elements in FIG. 6, and the various functions attributed to each of the elements, while exemplary, are described as such solely for the purposes of ease of understanding. One skilled in the art will appreciate that one or more of the functions ascribed to the various elements may be performed by any one of the other elements, and/or by an element (not shown) configured to perform a combination of the various functions. Therefore, it should be noted that any language directed to a training engine 610, a prediction engine 620, a persistent storage device 630 and a main memory device 640 should be read to include any suitable combination of computing devices, including servers, interfaces, systems, databases, agents, peers, engines, controllers, modules, or other types of computing devices operating individually or collectively to perform the functions ascribed to the various elements. Further, one skilled in the art will appreciate that one or more of the functions of the system of FIG. 6 described herein may be performed within the context of a client-server relationship, such as by one or more servers, one or more client devices (e.g., one or more user devices) and/or by a combination of one or more servers and client devices.

Figure 7:
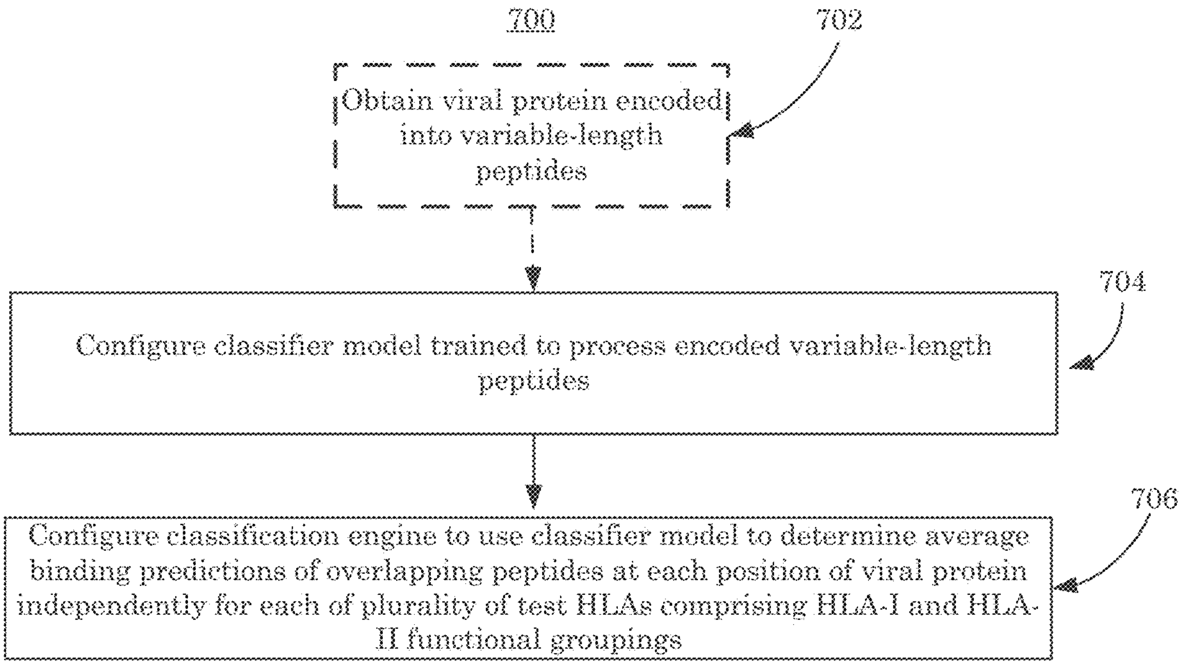
FIG. 7 illustrates a flow diagram of example operations for using a trained neural network to determine pan-HLA binding of viral proteins in accordance with an embodiment.

FIG. 7 illustrates a flow diagram of example operations for using a trained neural network to determine pan-HLA binding of viral proteins in accordance with an embodiment. In flow diagram 700, a viral protein, e.g., a SARS-CoV-2 protein variant such as a SARS-CoV-2 nucleocapsid (N) protein variant or spike (S) protein variant, encoded into variable-length peptides is obtained at step 702. For example, each of the encoded variable-length peptides may be between 8-15 amino acids in length. In some exemplary embodiments, the encoded variable-length peptides may have a dominant peptide length equal to 9-mers. In other exemplary embodiments, the encoded variable-length peptides may have a dominant peptide length equal to 15-mers.

At step 704, a classifier model trained to process encoded variable-length peptides is configured such that, independently per HLA, the classifier model is operable to determine at least one of (a) an average binding prediction of overlapping peptides at each position of a viral protein, (b) a maximum value of a binding prediction of overlapping peptides at each position of a viral protein, (c) standard deviation of a binding prediction of overlapping peptides at each position of a viral protein, and (d) a combination of one or more of (a)-(c). For example, the classifier model may be trained to make pan-HLA binding predictions using encoded variable-length peptides corresponding to a training viral protein and encoded variable-length proteins corresponding to one or more HLA alleles in the human population. Notably, the classifier model as disclosed herein may be trained to make pan-HLA binding predictions for HLA alleles in which little or no binding information is known using encoded variable-length proteins corresponding to one or more of a limited subset of HLA alleles in the human population.

At step 706, a classification engine is configured to use the classifier model to determine average binding predictions of overlapping peptides at each position of the viral protein independently for each of a plurality of test HLAs comprising HLA-I and HLA-II functional groupings, where the determining includes classifying a peptide as a binder when an average binding prediction corresponding to the peptide satisfies a binding prediction value threshold.

Figure 8:
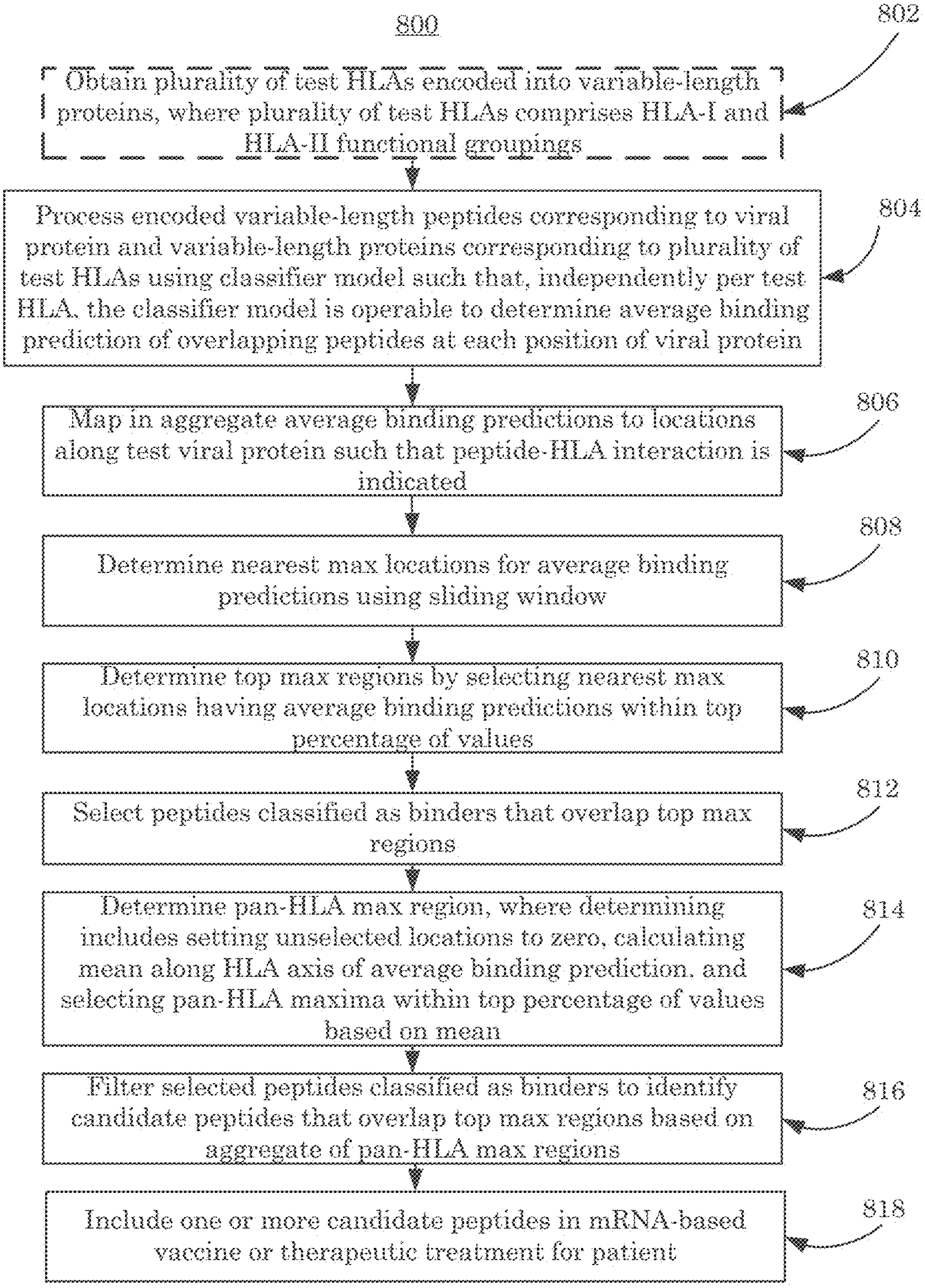
FIG. 8 illustrates a flow diagram of example operations for using a trained neural network to determine peptides for inclusion in a treatment or vaccine based on pan-HLA binding of viral proteins in accordance with an embodiment.

FIG. 8 illustrates a flow diagram of example operations for using a trained neural network to determine peptides for inclusion in a treatment or vaccine based on pan-HLA binding of viral proteins in accordance with an embodiment. In flow diagram 800, a plurality of test HLAs encoded into variable-length proteins is obtained at step 802, where the plurality of test HLAs comprises HLA-I and HLA-II functional groupings. The HLA-I functional grouping may comprise HLA-I protein sequences, and the HLA-II functional grouping may comprise HLA-II alpha chain and beta chain sequences. In an exemplary embodiment, the plurality of test HLAs may correspond to HLA allele frequencies in worldwide populations.

At step 804, the encoded variable-length peptides corresponding to the viral protein and the variable-length proteins corresponding to the plurality of test HLAs are processed using the classifier model such that, independently per test HLA, the classifier model is operable to determine an average binding prediction of overlapping peptides at each position of the viral protein.

Figure 9:
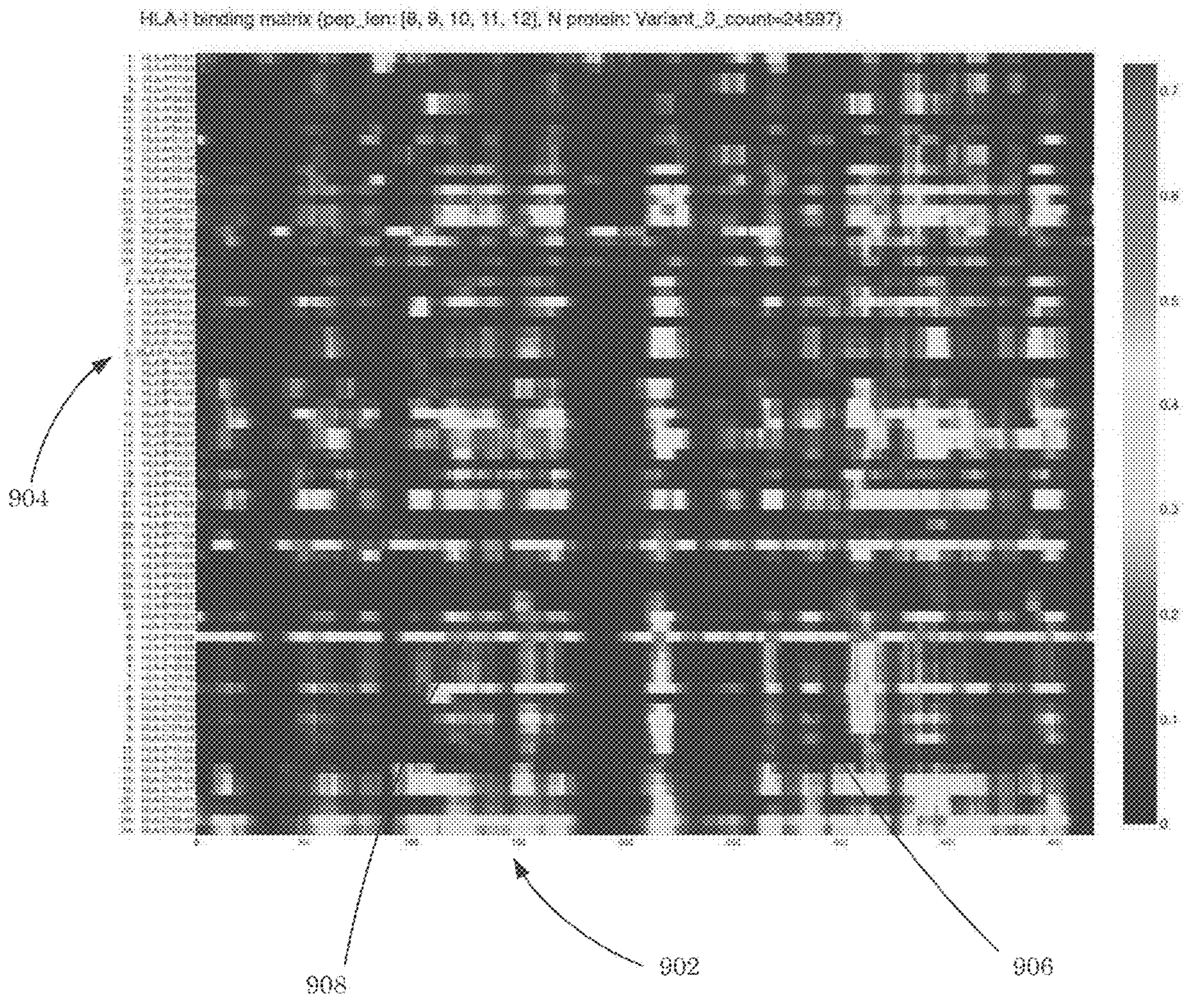
FIG. 9 illustrates a graphical representation of a binding matrix of pan-HLA I binding hotspots determined for a SARS-CoV-2 nucleocapsid (N) protein in accordance with an embodiment.
Figure 10:
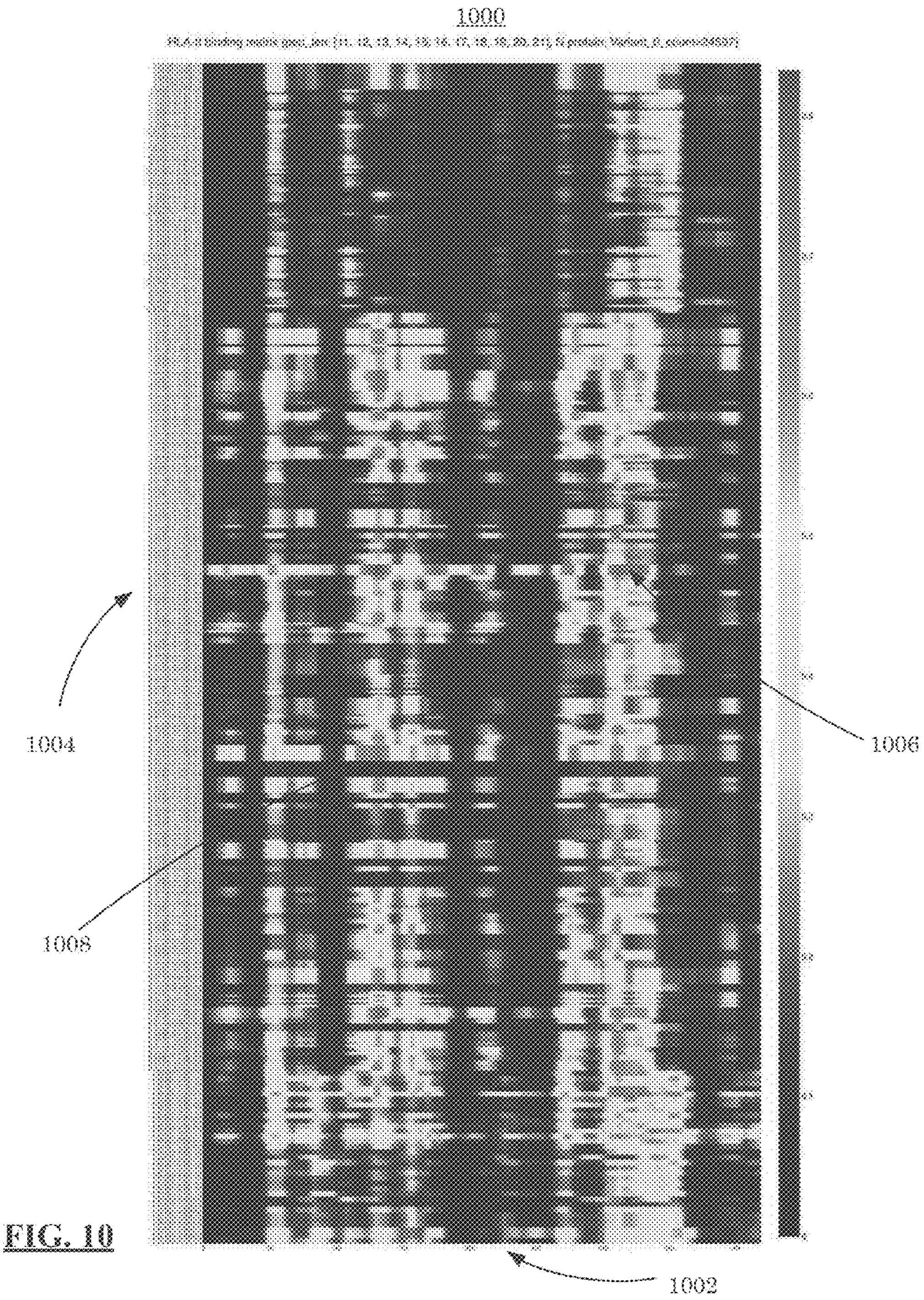
FIG. 10 illustrates a graphical representation of a binding matrix of pan-HLA II binding hotspots determined for a SARS-CoV-2 nucleocapsid (N) protein in accordance with an embodiment.

In an embodiment, the operations of steps 806-814 are performed independently per test HLA. At step 806, average binding predictions are mapped in aggregate to locations along the test viral protein such that peptide-HLA interaction is indicated. In some use cases, the mapping of peptide-HLA interaction may further include indicating locations signifying co-occurrences of peptide attention and HLA attention. FIG. 9 illustrates a graphical representation of a binding matrix of pan-HLA I binding hotspots determined for a SARS-CoV-2 nucleocapsid (N) protein in accordance with an embodiment. Graphical representation 900 is a heat map showing the binding properties of a SARS-CoV-2 nucleocapsid (N) protein variant 902 relative to a plurality of HLA-I protein sequences 904, where the peptide length of the variable-length peptides is between 8 and 12-mers. The binding hot spots, e.g., locations 906 and 908, represent the highest of average binding prediction values of overlapping peptides at each position of the viral protein. Similarly, FIG. 10 illustrates a graphical representation of a binding matrix of pan-HLA II binding hotspots determined for a SARS-CoV-2 nucleocapsid (N) protein in accordance with an embodiment. Graphical representation 1000 is a heat map showing the binding properties of a SARS-CoV-2 nucleocapsid (N) protein variant 1002 relative to a plurality of HLA-II protein sequences 1004, where the peptide length of the variable-length peptides is between 11 and 21-mers. For example, the plurality of HLA-II protein sequences 1004 may comprise HLA-II alpha chain and beta chain sequences. The binding hot spots, e.g., locations 1006 and 1008, represent the highest of average binding prediction values of overlapping peptides at each position of the viral protein.

Returning to step 808, nearest max locations are determined for the average binding predictions using a sliding window having a fixed length. For example, the fixed length of the sliding window may be based on a dominant peptide length of the variable-length peptides, e.g., 9-mers or 15-mers.

Figure 11:
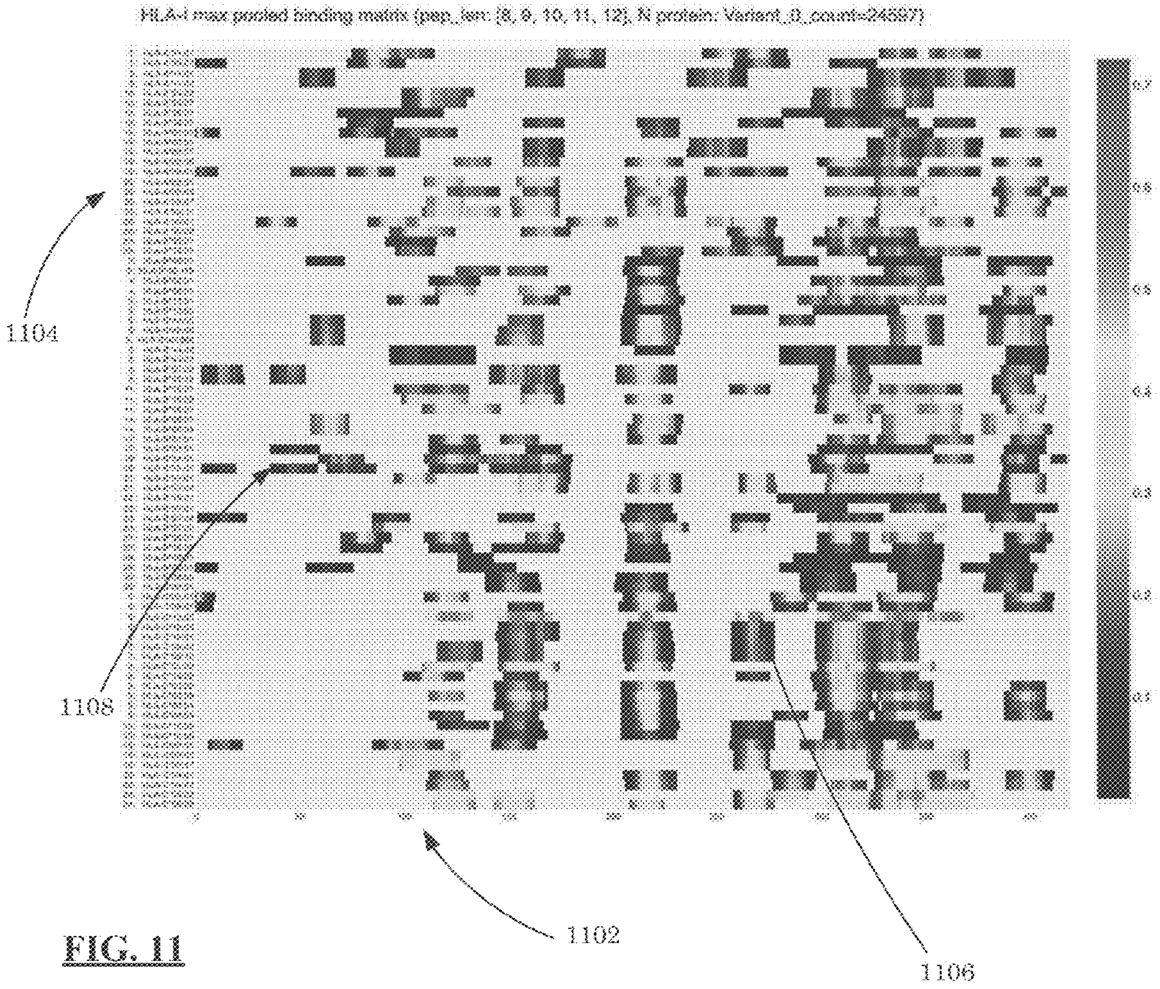
FIG. 11 illustrates a graphical representation of a max pooled binding matrix of pan-HLA I binding hotspots determined for a SARS-CoV-2 nucleocapsid (N) protein in accordance with an embodiment.
Figure 12:
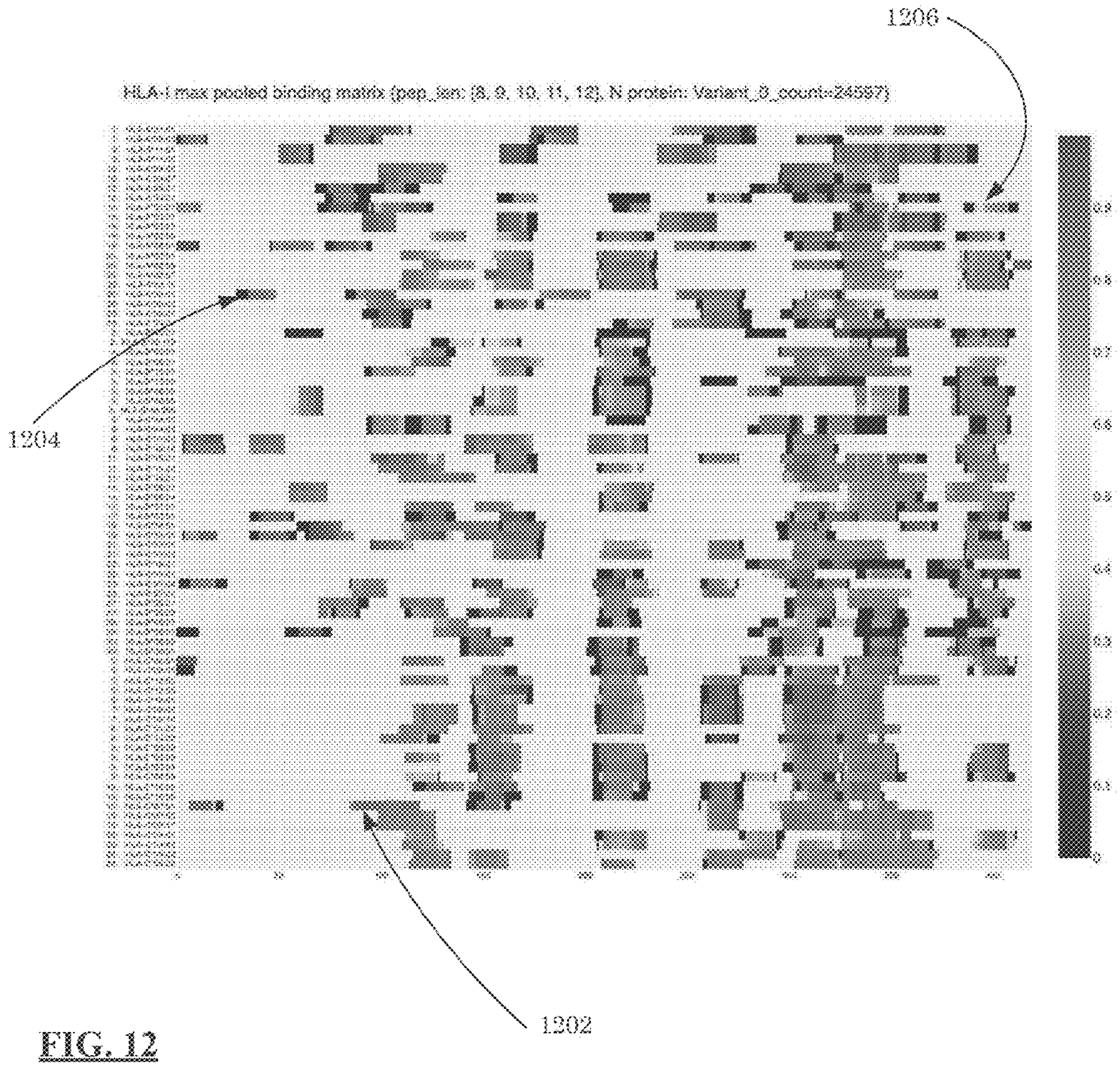
FIG. 12 illustrates a graphical representation of a max pooled binding matrix of pan-HLA I binding hotspots determined for a SARS-CoV-2 nucleocapsid (N) protein in accordance with an embodiment.
Figure 13:
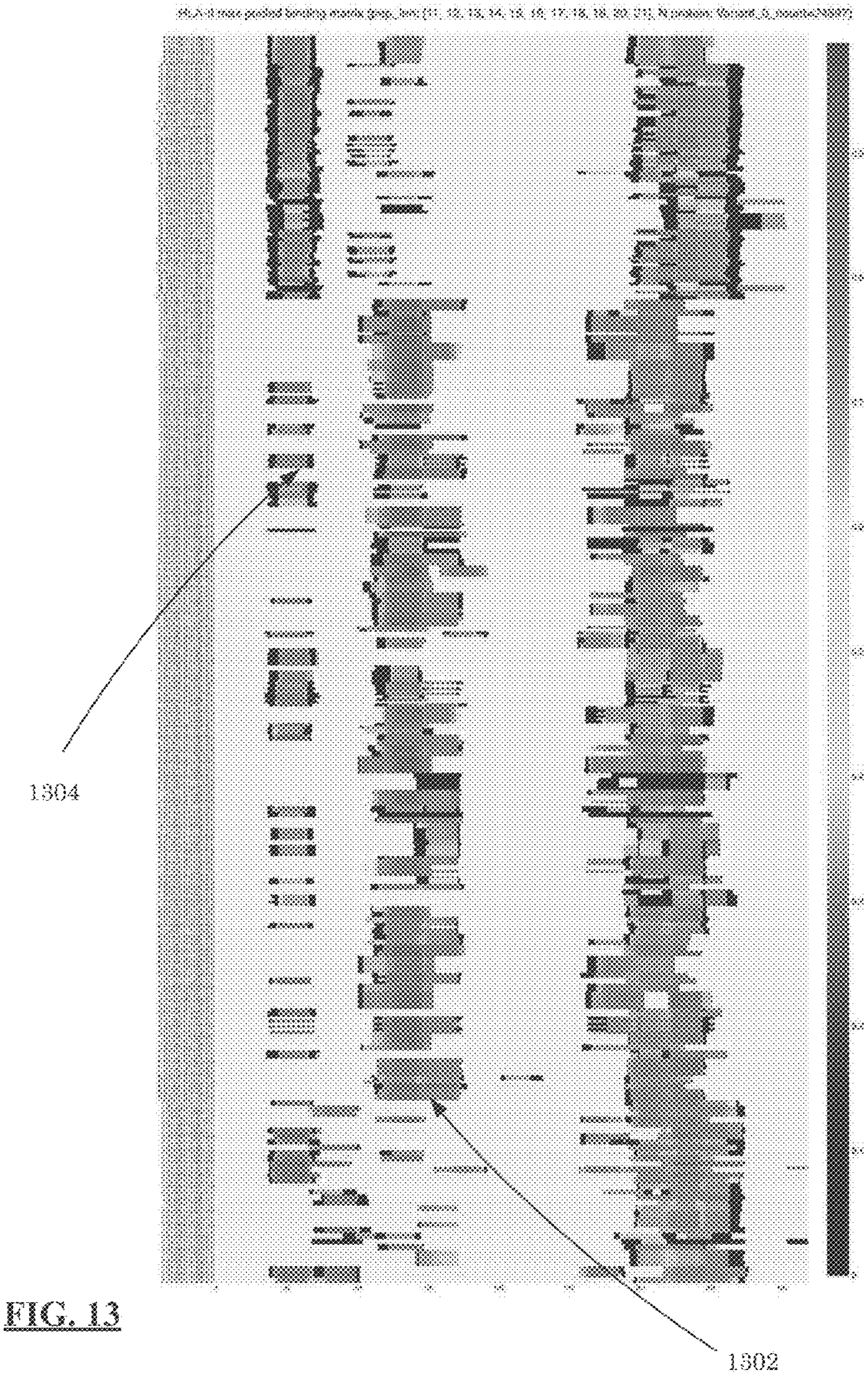
FIG. 13 illustrates a graphical representation of a max pooled binding matrix of pan-HLA II binding hotspots determined for a SARS-CoV-2 nucleocapsid (N) protein in accordance with an embodiment.

At step 810, top max regions are determined by selecting the nearest max locations having average binding predictions within a top percentage of values. For example, the top max regions may be determined by selecting the nearest max locations having average binding predictions within a top 10% of values, within a top 25% of values, or another selected top percentage of values. In FIG. 11, graphical representation 1100 is a heat map showing the max pooled binding properties of a SARS-CoV-2 nucleocapsid (N) protein variant 1102 relative to a plurality of HLA-I protein sequences 1104, where the peptide length of the variable-length peptides is between 8 and 12-mers. The max pooled binding hot spots, e.g., locations 1106 and 1108, represent the nearest max locations of the average binding predictions, e.g., determined by using a sliding window having a fixed length. For example, the fixed length of the sliding window may be based on a dominant peptide length of the variable-length peptides, e.g., 9-mers or 15-mers. Locations that belong to maxima within a top 10% of values may be selected (Independently per HLA) as nearest max locations. For example, in FIG. 12, graphical representation 1200 is a heat map showing the selection (independently per HLA) of all peptides classified as binders, e.g., peptides 1202, 1204, and 1206, that overlap top max regions. Likewise, in FIG. 13, graphical representation 1300 is a heat map showing the max pooled binding properties of a SARS-CoV-2 nucleocapsid (N) protein variant relative to a plurality of HLA-II protein sequences, where the peptide length of the variable-length peptides is between 11 and 21-mers. The max pooled binding hot spots, e.g., locations 1302 and 1304, represent the nearest max locations of the average binding predictions, e.g., determined by using a sliding window having a fixed length. For example, the fixed length of the sliding window may be based on a dominant peptide length of the variable-length peptides. Locations that belong to maxima within a top 10% of values may be selected (Independently per HLA) as nearest max locations.

Figure 14:
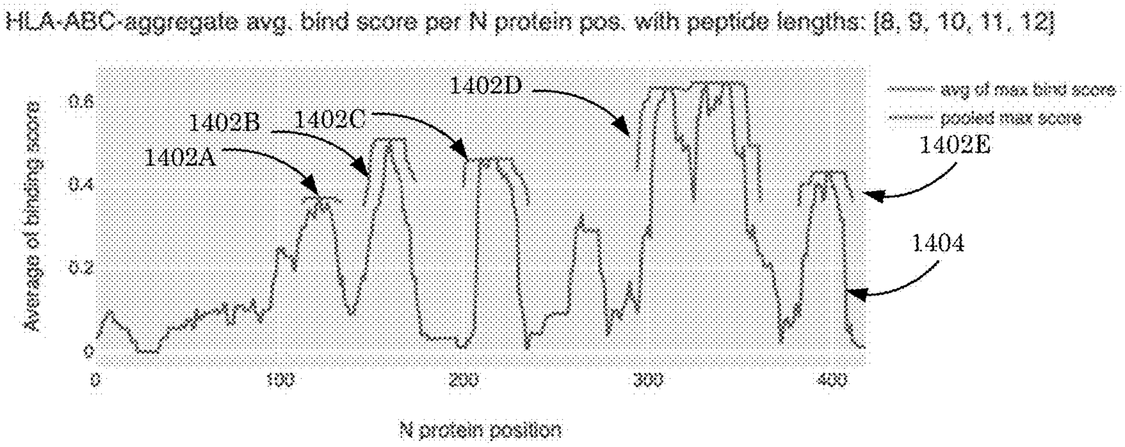
FIG. 14 illustrates a graphical representation of aggregate average binding scores and pooled max scores of pan-HLA I binding hotspots determined for a SARS-CoV-2 nucleocapsid (N) protein in accordance with an embodiment.
Figure 15:
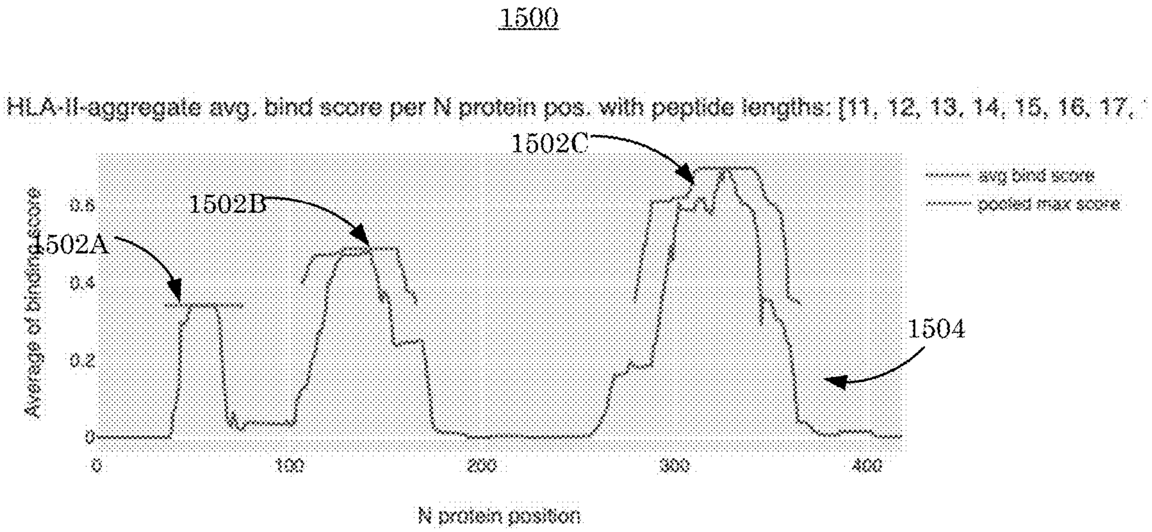
FIG. 15 illustrates a graphical representation of aggregate average binding scores and pooled max scores of pan-HLA II binding hotspots determined for a SARS-CoV-2 nucleocapsid (N) protein in accordance with an embodiment.

Returning to step 812, peptides classified as binders that overlap the top max regions are selected, and a pan-HLA max region is determined at step 814, where the determining includes setting unselected locations to zero, calculating a mean along an HLA axis of the average binding prediction, and selecting pan-HLA maxima within a top percentage of values based on the mean. For example, the pan-HLA max region may be determined by selecting pan-HLA maxima within a top 25% of values. FIG. 14 illustrates a graphical representation of aggregate average binding scores and pooled max scores of pan-HLA I binding hotspots determined for a SARS-CoV-2 nucleocapsid (N) protein in accordance with an embodiment. In graphical representation 1400, pan-HLA max regions, 1402A-E, of aggregate average binding scores 1404 are shown. For example, the pan-HLA max regions 1402A-E may be determined by setting all unselected HLA vs protein positions to zero, computing a mean along the HLA axis, and selecting maxima based on a top 25% of values. Likewise, FIG. 15 illustrates a graphical representation of aggregate average binding scores and pooled max scores of pan-HLA II binding hotspots determined for a SARS-CoV-2 nucleocapsid (N) protein in accordance with an embodiment. In graphical representation 1500, pan-HLA max regions, 1502A-C, of aggregate average binding scores 1504 are shown. For example, the pan-HLA max regions 1502A-C may be determined by setting all unselected HLA vs protein positions to zero, computing a mean along the HLA axis, and selecting maxima based on a top 25% of values.

Returning to step 816, the selected peptides classified as binders are filtered independently for each of the HLA-I and HLA-II functional groupings to identify candidate peptides that overlap the top max regions based on an aggregate of the pan-HLA max regions, and, at step 818, one or more of the candidate peptides are included in an mRNA-based vaccine or therapeutic treatment for a patient. For example, the mRNA-based vaccine or therapeutic treatment may be capable of treating a patient having SARS-CoV-2, and at least one of the candidate peptides may be selected for inclusion in the mRNA-based vaccine or therapeutic treatment for the patient based on HLA allele frequencies in worldwide populations.

Figure 16:
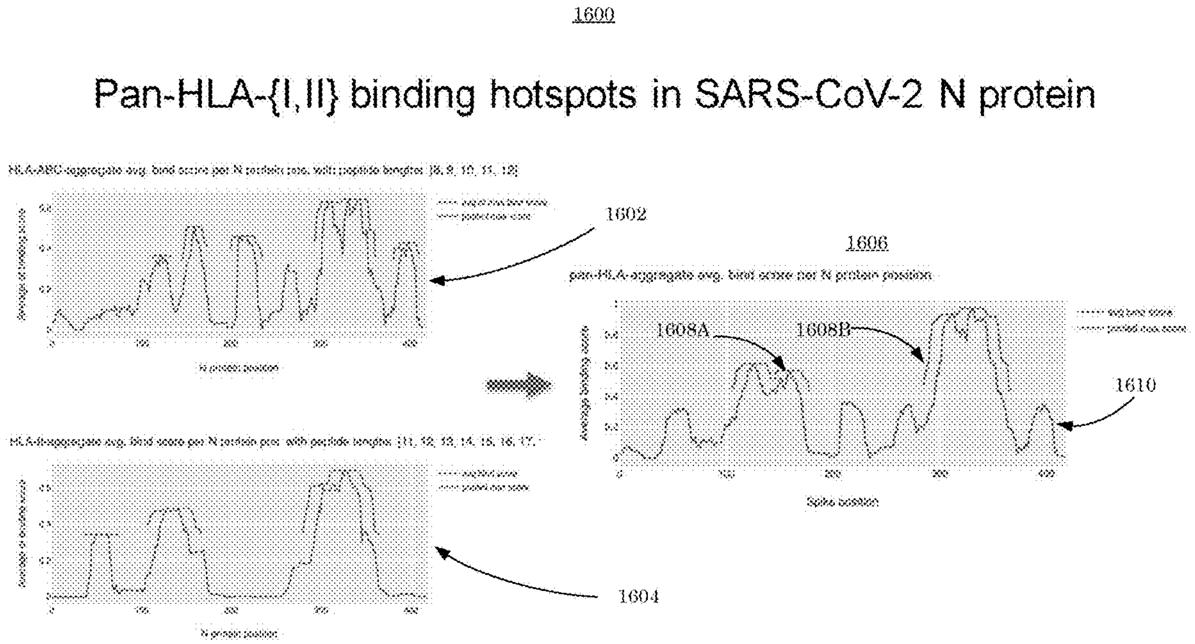
FIG. 16 illustrates a graphical representation of a filtering of selected peptides classified as binders to identify candidate peptides that overlap the top max regions based on an aggregate of pan-HLA-{I, II} max regions determined for a SARS-CoV-2 nucleocapsid (N) protein in accordance with an embodiment.

FIG. 16 illustrates a graphical representation of a filtering of selected peptides classified as binders to identify candidate peptides that overlap the top max regions based on an aggregate of pan-HLA {I, II} max regions determined for a SARS-CoV-2 nucleocapsid (N) protein in accordance with an embodiment. The selected peptides classified as binders are filtered independently for each of the HLA-I and HLA-II functional groupings as illustrated, for example, in graphs 1602 and 1604, respectively, candidate peptides are identified that overlap the top max regions based on an aggregate of the pan-HLA max regions, as shown in graph 1606. For example, top max regions 1608A-B of the aggregate pan-HLA max regions 1610 may be selected to identify candidate peptides for inclusion in a SARS-CoV-2 vaccine or therapeutic treatment. Further, reduced predicted binding in these regions could be used to determine SARS-CoV-2 lineages for which a vaccine based on the original reference genome may have lower efficacy due to the potential for lower and distinct epitope presentation from highly immunogenic regions.

Figure 17:
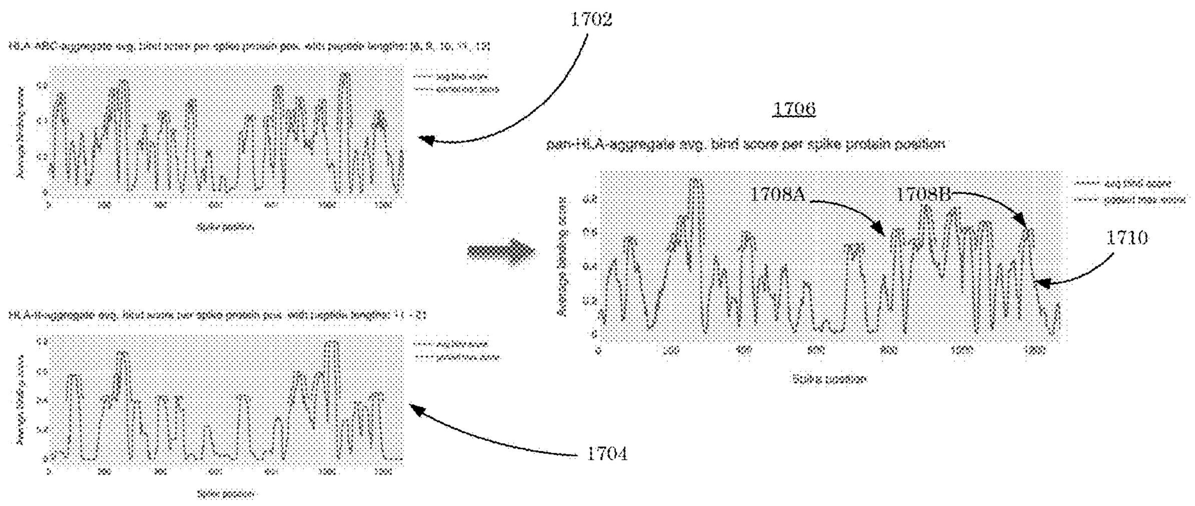
FIG. 17 illustrates a graphical representation of a filtering of selected peptides classified as binders to identify candidate peptides that overlap the top max regions based on an aggregate of pan-HLA{I, II} max regions determined for a SARS-CoV-2 spike (S) protein in accordance with an embodiment.

FIG. 17 illustrates a graphical representation of a filtering of selected peptides classified as binders to identify candidate peptides that overlap the top max regions based on an aggregate of pan-HLA {I, II} max regions determined for a SARS-CoV-2 spike (S) protein in accordance with an embodiment. Similar to above, the selected peptides classified as SARS-CoV-2 spike (S) protein binders are filtered independently for each of the HLA-I and HLA-II functional groupings as illustrated, for example, in graphs 1702 and 1704, respectively, and candidate peptides are identified that overlap the top max regions based on an aggregate of the pan-HLA max regions, as shown in graph 1706. For example, top max regions 1708A-B of the aggregate pan-HLA max regions 1710 may be selected to identify candidate peptides for inclusion in a SARS-CoV-2 vaccine or therapeutic treatment. Further, reduced predicted binding in these regions could be used to determine SARS-CoV-2 lineages for which a vaccine based on the original reference genome may have lower efficacy due to the potential for lower and distinct epitope presentation from highly immunogenic regions.

Figure 18:
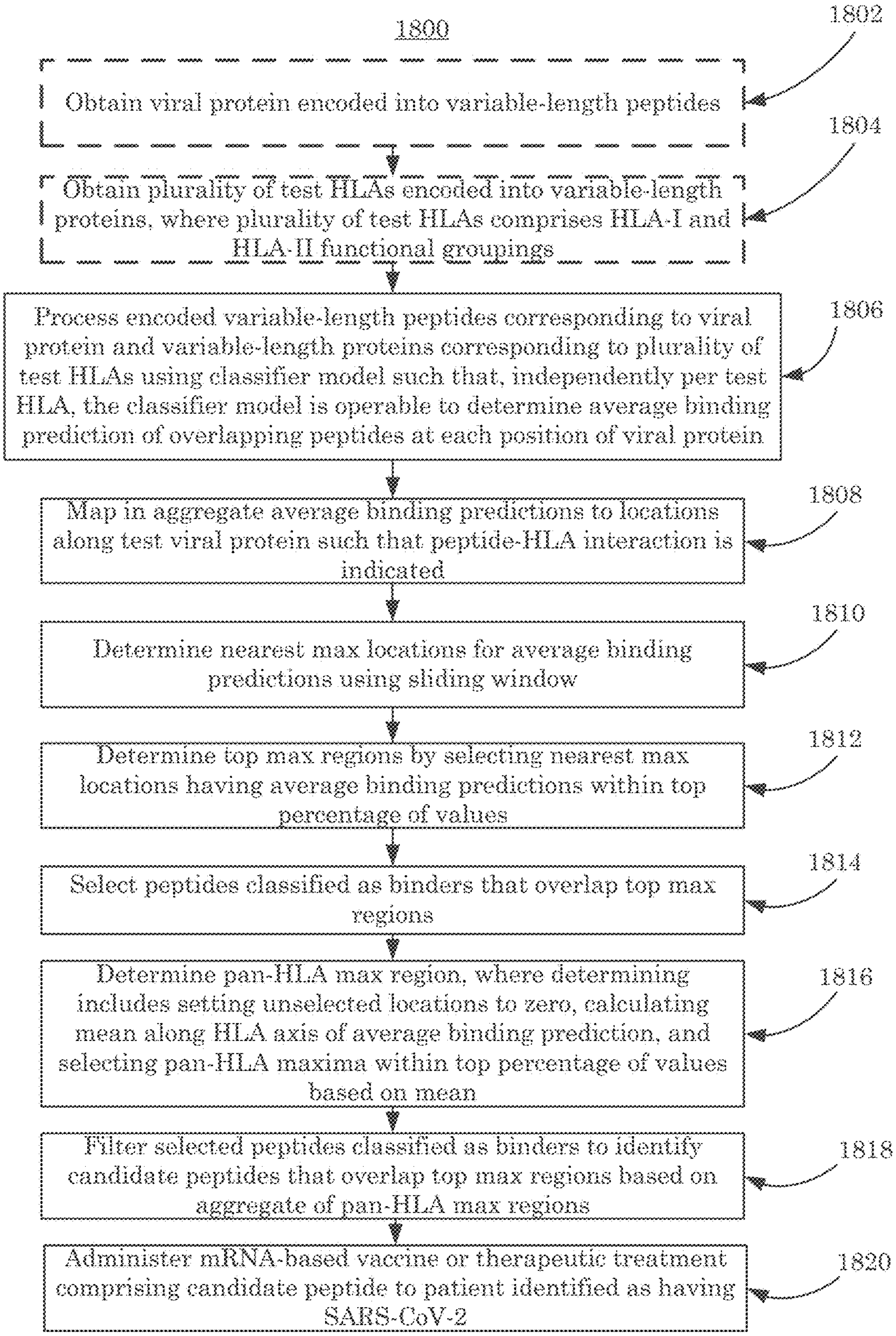
FIG. 18 illustrates a flow diagram of example operations for using a trained neural network to determine a method of treatment based on pan-HLA binding of viral proteins in accordance with an embodiment.

FIG. 18 illustrates a flow diagram of example operations for using a trained neural network to determine a method of treatment based on pan-HLA binding of viral proteins in accordance with an embodiment. In flow diagram 1800, a viral protein encoded into variable-length peptides and a plurality of test HLAs encoded into variable-length proteins are obtained at steps 1802 and 1804, respectively. In an embodiment, the plurality of test HLAs comprises HLA-I and HLA-II functional groupings. At step 1806, the encoded variable-length peptides corresponding to the viral protein and the variable-length proteins corresponding to the plurality of test HLAs are processed using the classifier model such that, independently per test HLA, the classifier model is operable to determine an average binding prediction of overlapping peptides at each position of the viral protein.

In an embodiment, the operations of steps 1808-1816 are performed independently per test HLA. At step 1808, average binding predictions are mapped in aggregate to locations along the test viral protein such that peptide-HLA interaction is indicated. At step 1810, nearest max locations are determined for the average binding predictions using a sliding window having a fixed length. At step 1812, top max regions are determined by selecting the nearest max locations having average binding predictions within a top percentage of values, and peptides classified as binders that overlap the top max regions are selected at step 1814. At step 1816, a pan-HLA max region is determined, where the determining includes setting unselected locations to zero, calculating a mean along an HLA axis of the average binding prediction, and selecting pan-HLA maxima within a top percentage of values based on the mean.

The selected peptides classified as binders are filtered independently for each of the HLA-I and HLA-II functional groupings to identify candidate peptides that overlap the top max regions based on an aggregate of the pan-HLA max regions at step 1818. At step 1820, an mRNA-based vaccine or therapeutic treatment comprising one or more of the candidate peptides is administered to a patient identified as having SARS-CoV-2. For example, at least one of the candidate peptides may be selected for inclusion in the mRNA-based vaccine or therapeutic treatment for the patient based on HLA allele frequencies in worldwide populations, and the plurality of test HLAs may correspond to HLA allele frequencies in worldwide populations. In some embodiments, the test viral protein may comprise a SARS-CoV-2 protein variant such as a SARS-CoV-2 nucleocapsid (N) protein variant or spike (S) protein variant, and the mRNA-based vaccine or therapeutic treatment may be capable of treating a patient having SARS-CoV-2.

A high-level block diagram of an exemplary client-server relationship that may be used to implement systems, apparatus and methods described herein is illustrated in FIG. 19. Client-server relationship 1900 comprises client 1910 in communication with server 1920 via network 1930 and illustrates one possible division of determining pan-HLA binding of viral proteins between client 1910 and server 1920.

For example, client 1910, in accordance with the various embodiments described above, may obtain a viral protein encoded into variable-length peptides, and a plurality of HLAs encoded into variable-length proteins, where the plurality of HLAs may comprise HLA-I and HLA-II functional groupings.

Server 1920 may configure a classifier model trained to process encoded variable-length peptides such that, independently per HLA, the classifier model is operable to determine at least one of (a) an average binding prediction of overlapping peptides at each position of the viral protein, (b) a maximum value of a binding prediction of overlapping peptides at each position of the viral protein, (c) standard deviation of a binding prediction of overlapping peptides at each position of the viral protein, and (d) a combination of one or more of (a)-(c); and configure a classification engine to use the classifier model to determine average binding predictions of overlapping peptides at each position of the viral protein independently for each of a plurality of test HLAs comprising HLA-I and HLA-II functional groupings, where the determining includes classifying a peptide as a binder when an average binding prediction corresponding to the peptide satisfies a binding value threshold.

Server 1920 may further obtain a plurality of test HLAs encoded into variable-length proteins, where the plurality of test HLAs comprises HLA-I and HLA-II functional groupings, and process the encoded variable-length peptides corresponding to the viral protein and the variable-length proteins corresponding to the plurality of test HLAs using the classifier model such that, independently per test HLA, the classifier model is operable to determine an average binding prediction of overlapping peptides at each position of the viral protein.

Independently per test HLA, Server 1920 may map in aggregate average binding predictions to locations along the test viral protein such that peptide-HLA interaction is indicated; determine nearest max locations for the average binding predictions using a sliding window having a fixed length; determine top max regions by selecting the nearest max locations having average binding predictions within a top percentage of values; select peptides classified as binders that overlap the top max regions; and determine a pan-HLA max region, where the determining includes setting unselected locations to zero, calculating a mean along an HLA axis of the average binding prediction, and selecting pan-HLA maxima within a top percentage of values based on the mean.

Independently for each of the HLA-I and HLA-II functional groupings, server 1920 may filter the selected peptides classified as binders to identify candidate peptides that overlap the top max regions based on an aggregate of the pan-HLA max regions, where one or more of the candidate peptides may be included in an mRNA-based vaccine or therapeutic treatment for a patient.

One skilled in the art will appreciate that the exemplary client-server relationship illustrated in FIG. 19 is only one of many client-server relationships that are possible for implementing the systems, apparatus, and methods described herein. As such, the client-server relationship illustrated in FIG. 19 should not, in any way, be construed as limiting. Examples of client devices 1910 can include cellular smartphones, kiosks, personal data assistants, tablets, robots, vehicles, web cameras, or other types of computing devices.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 7, 8, and 18, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 20:
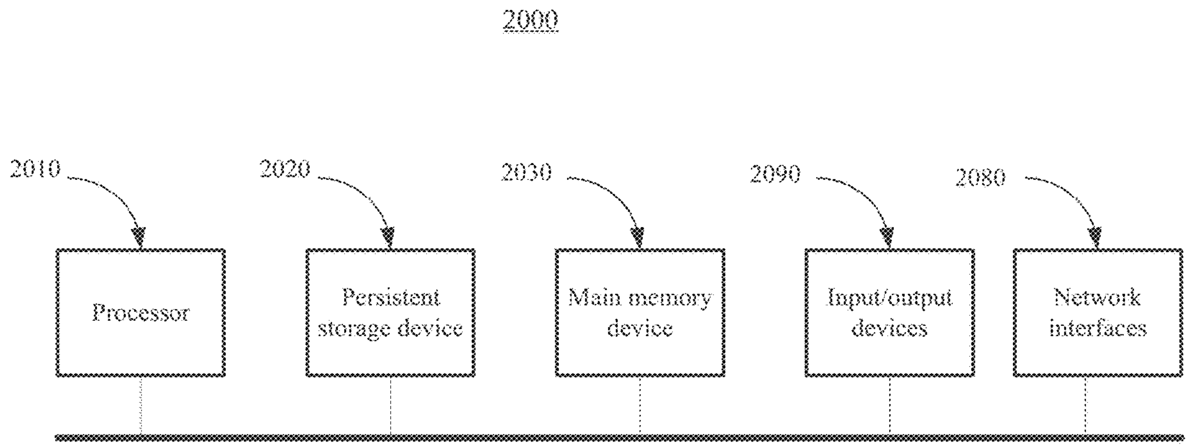
FIG. 20 illustrates a block diagram of a distributed computer system that can be used for implementing one or more aspects of the various embodiments.

A high-level block diagram of an exemplary apparatus that may be used to implement systems, apparatus and methods described herein is illustrated in FIG. 20. Apparatus 2000 comprises a processor 2010 operatively coupled to a persistent storage device 2020 and a main memory device 2030. Processor 2010 controls the overall operation of apparatus 2000 by executing computer program instructions that define such operations. The computer program instructions may be stored in persistent storage device 2020, or other computer-readable medium, and loaded into main memory device 2030 when execution of the computer program instructions is desired. For example, training engine 610 and prediction engine 620 may comprise one or more components of computer 2000. Thus, the method steps of FIGS. 7, 8, and 18 can be defined by the computer program instructions stored in main memory device 2030 and/or persistent storage device 2020 and controlled by processor 2010 executing the computer program instructions. For example, the computer program instructions can be implemented as computer executable code programmed by one skilled in the art to perform an algorithm defined by the method steps of FIGS. 7, 8, and 18. Accordingly, by executing the computer program instructions, the processor 2010 executes an algorithm defined by the method steps of FIGS. 7, 8, and 18. Apparatus 2000 also includes one or more network interfaces 2080 for communicating with other devices via a network. Apparatus 2000 may also include one or more input/output devices 2090 that enable user interaction with apparatus 2000 (e.g., display, keyboard, mouse, speakers, buttons, etc.).

Processor 2010 may include both general and special purpose microprocessors and may be the sole processor or one of multiple processors of apparatus 2000. Processor 2010 may comprise one or more central processing units (CPUs), and one or more graphics processing units (GPUs), which, for example, may work separately from and/or multi-task with one or more CPUs to accelerate processing, e.g., for various image processing applications described herein. Processor 2010, persistent storage device 2020, and/or main memory device 2030 may include, be supplemented by, or incorporated in, one or more application-specific integrated circuits (ASICs) and/or one or more field programmable gate arrays (FPGAs).

Persistent storage device 2020 and main memory device 2030 each comprise a tangible non-transitory computer readable storage medium. Persistent storage device 2020, and main memory device 2030, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 2090 may include peripherals, such as a printer, scanner, display screen, etc. For example, input/output devices 2090 may include a display device such as a cathode ray tube (CRT), plasma or liquid crystal display (LCD) monitor for displaying information (e.g., a DNA accessibility prediction result) to a user, a keyboard, and a pointing device such as a mouse or a trackball by which the user can provide input to apparatus 2000.

Any or all of the systems and apparatuses discussed herein, including training engine 610 and prediction engine 620 may be performed by, and/or incorporated in, an apparatus such as apparatus 2000. Further, apparatus 2000 may utilize one or more neural networks or other deep-learning techniques to perform training engine 610 and prediction engine 620 or other systems or apparatuses discussed herein.

One skilled in the art will recognize that an implementation of an actual computer or computer system may have other structures and may contain other components as well, and that FIG. 20 is a high-level representation of some of the components of such a computer for illustrative purposes.

FIGS. 21-66 illustrate performance validation data for a neural network trained to determine pan-HLA binding of viral proteins in accordance with an embodiment.

FIG. 21 illustrates performance validation data for a trained Recurrent Neural Net with Attention & MHC-SEQ in accordance with an embodiment in comparison with NetMHCpan4.1.

Figure 22:
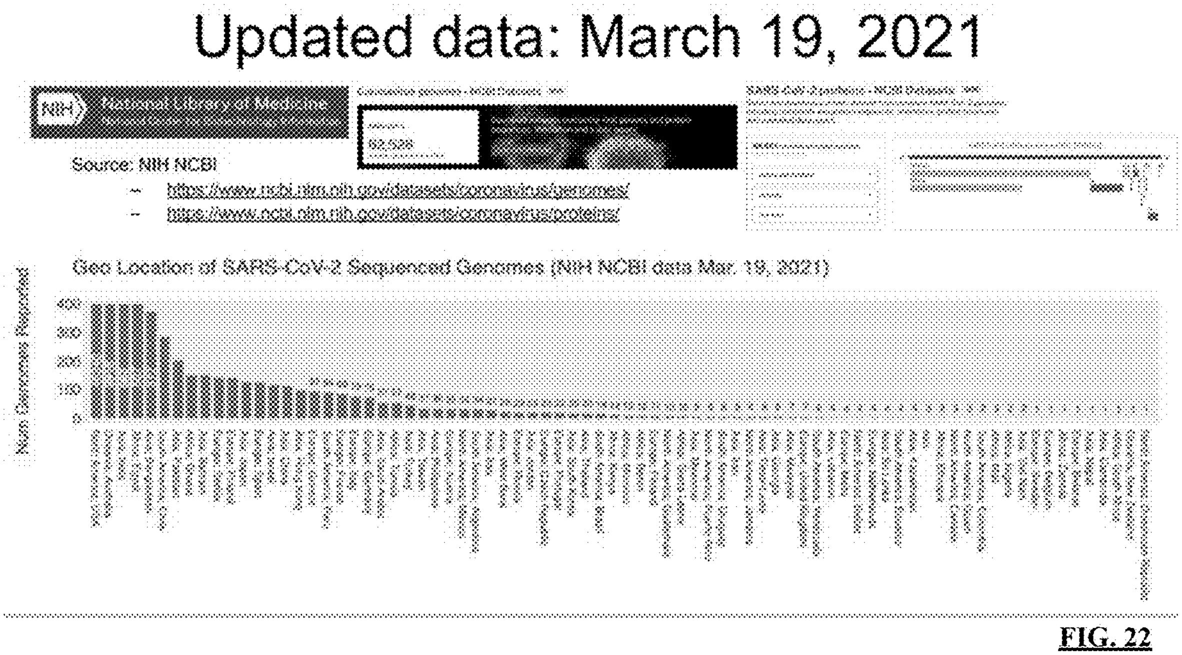
FIG. 22 illustrates a chart of SARS-CoV-2 sequenced genomes obtained from National Institutes of Health (NIH) National Center for Biotechnology Information datasets.

FIG. 22 illustrates a chart of SARS-CoV-2 sequenced genomes obtained from National Institutes of Health (NIH) National Center for Biotechnology Information datasets.

Figure 23:
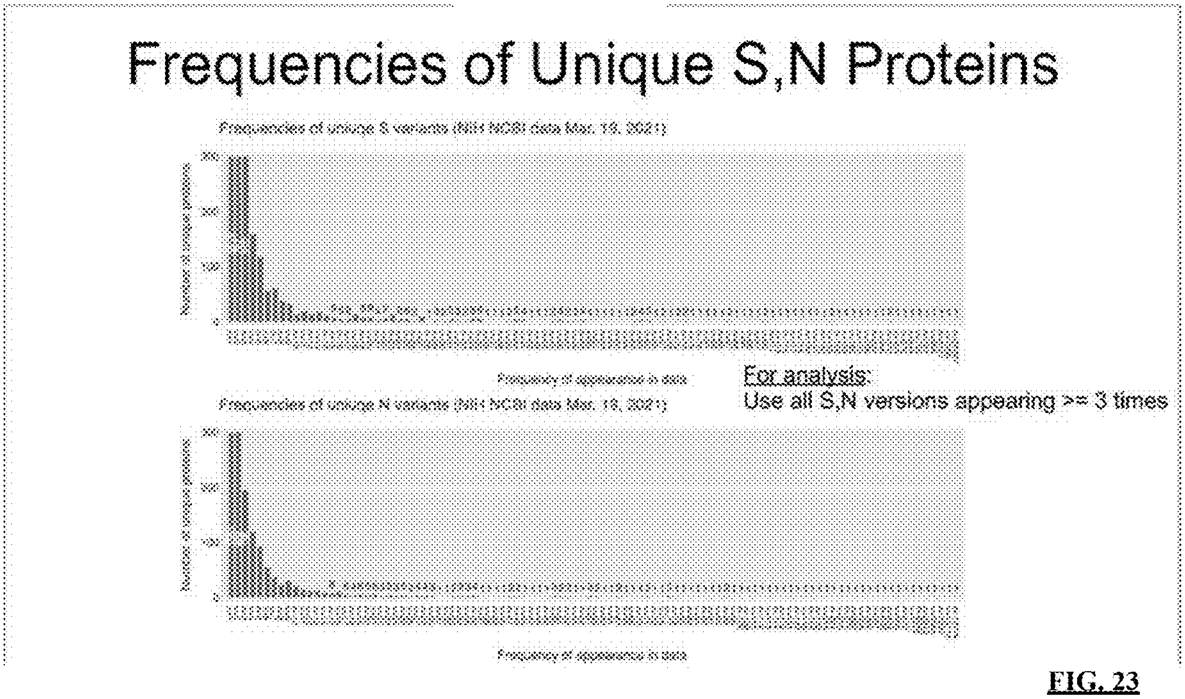
FIG. 23 illustrates charts showing frequencies of unique S and N proteins in the SARS-CoV-2 sequenced genomes reported in various geographical locations.

FIG. 23 illustrates charts showing frequencies of unique S and N proteins in the SARS-CoV-2 sequenced genomes reported in various geographical locations.

FIG. 24 illustrates graphical representations of learned HLA functional similarity groupings.

FIG. 25 illustrates a method of selection of HLA-I and HLA-II clusters in accordance with an embodiment.

Figure 26:
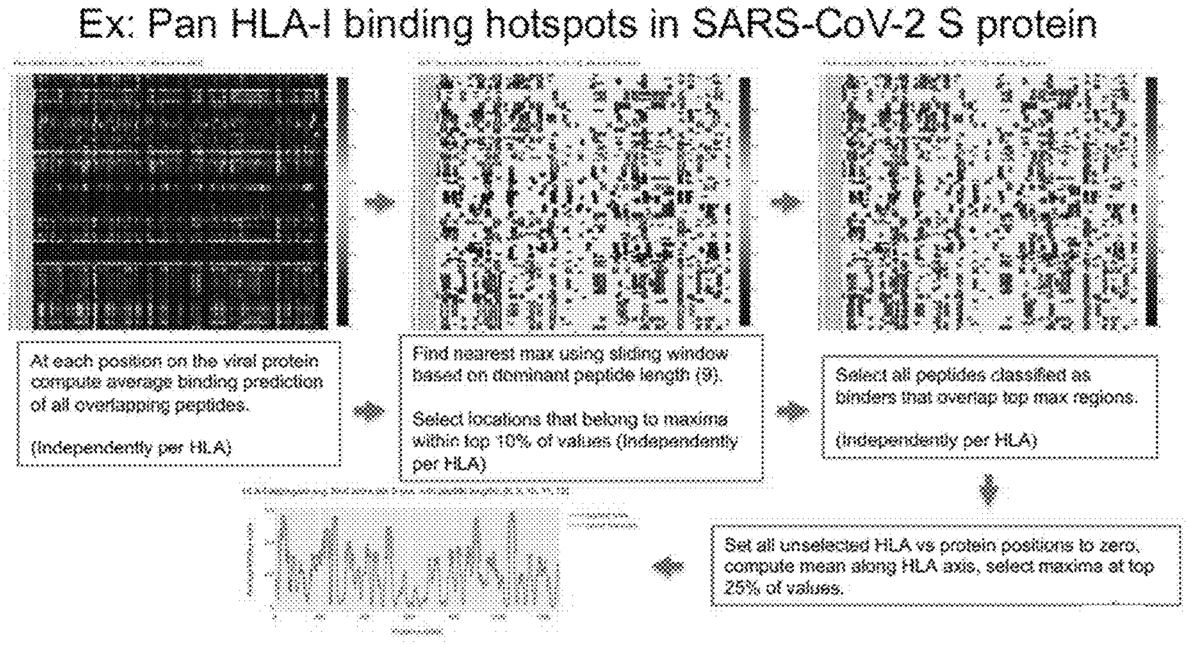
FIG. 26 illustrates a flow diagram of performance validation operations for using a trained neural network to determine pan HLA-I binding hotspots in SARS-CoV-2 S protein in accordance with an embodiment.

FIG. 26 illustrates a flow diagram of performance validation operations for using a trained neural network to determine pan HLA-I binding hotspots in SARS-CoV-2 S protein in accordance with an embodiment.

Figure 27:
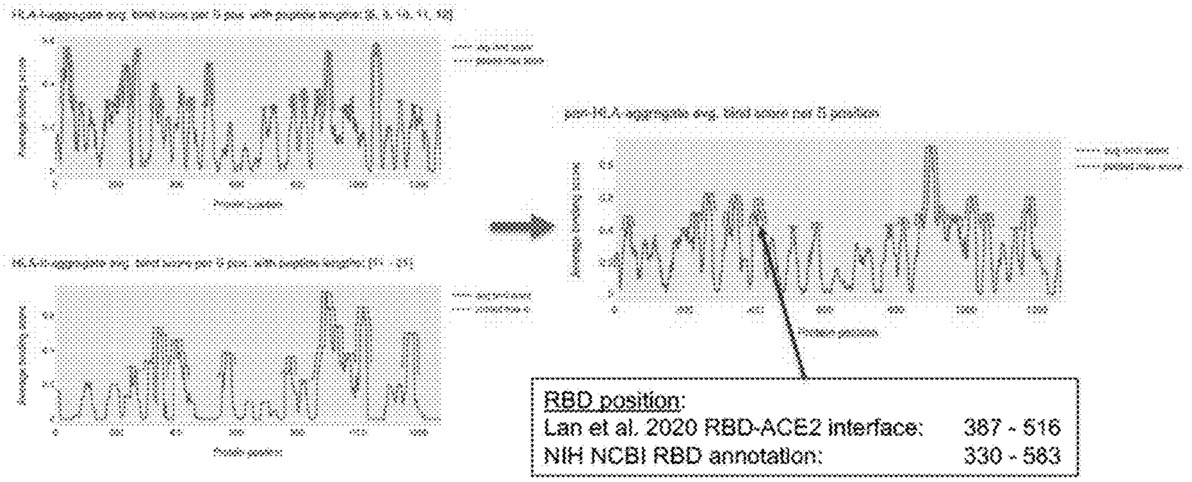
FIG. 27 illustrates a flow diagram of performance validation operations for using a trained neural network to determine pan-HLA-{I, II} binding hotspots in SARS-CoV-2 S protein in accordance with an embodiment. Hotspot locations are mapped to each protein variant in later analysis.

FIG. 27 illustrates a flow diagram of performance validation operations for using a trained neural network to determine pan-HLA-{I, II} binding hotspots in SARS-CoV-2 S protein in accordance with an embodiment. Hotspot locations are mapped to each protein variant in later analysis.

Figure 28:
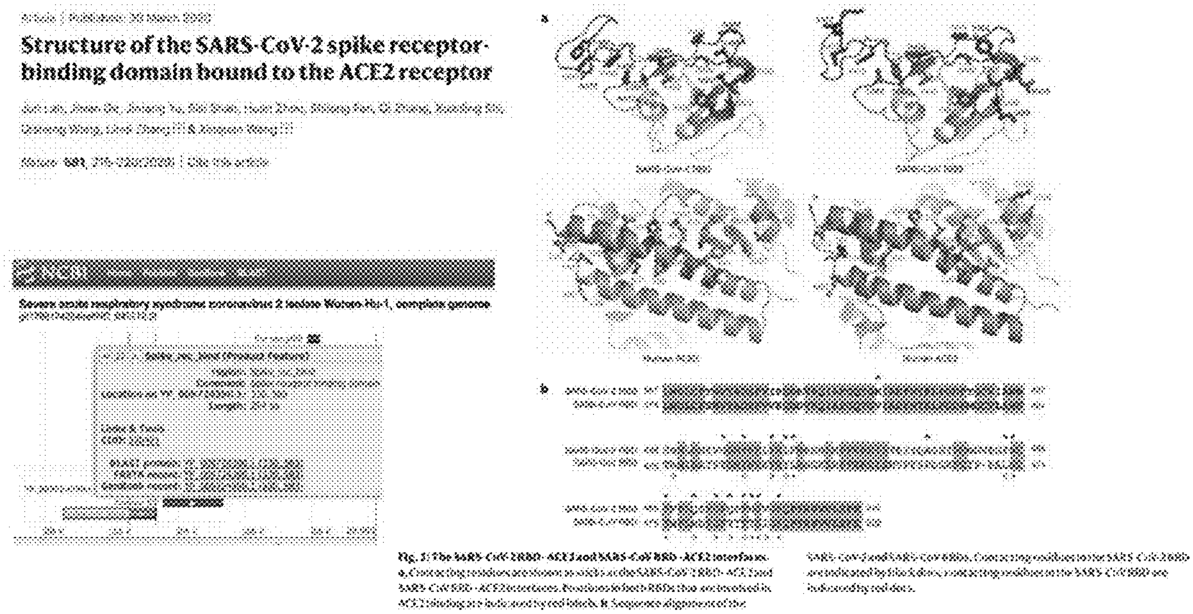
FIG. 28 illustrates the published work of Lan et al., titled "Structure of the SARS-CoV-2 Spike Receptor-Binding Domain Bound to the ACE2 Receptor."

FIG. 28 illustrates the published work of Lan et al., titled "Structure of the SARS-CoV-2 Spike Receptor-Binding Domain Bound to the ACE2 Receptor."

Figure 29:
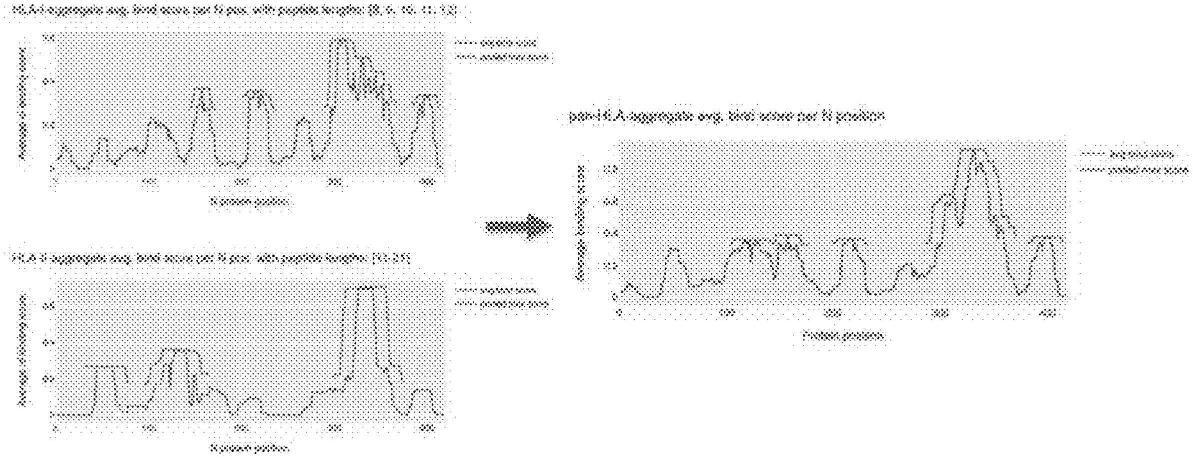
FIG. 29 illustrates a flow diagram of performance validation operations for using a trained neural network to determine Pan-HLA-{I, II} binding hotspots in SARS-CoV-2 N protein in accordance with an embodiment.

FIG. 29 illustrates a flow diagram of performance validation operations for using a trained neural network to determine Pan-HLA-{I, II} binding hotspots in SARS-CoV-2 N protein in accordance with an embodiment.

Figure 30:
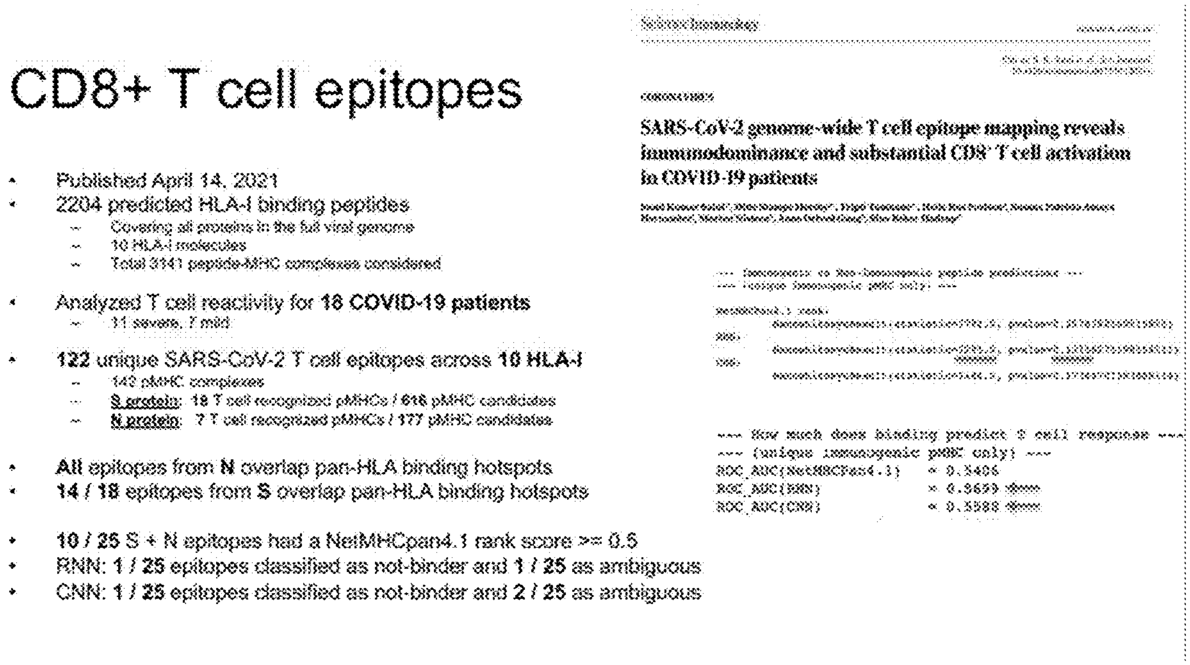
FIG. 30 illustrates a performance validation comparison of binding predictions for CD8+ T cell epitopes.

FIG. 30 illustrates a performance validation comparison of binding predictions for CD8+ T cell epitopes.

Figure 31:
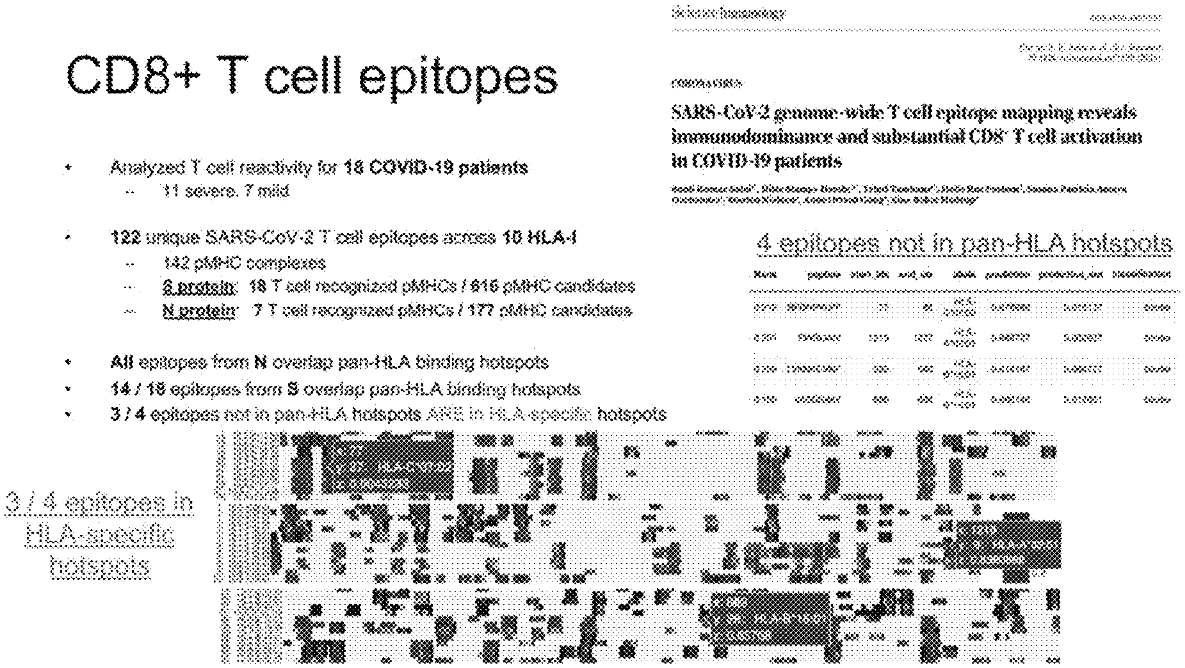
FIG. 31 illustrates a performance validation hotspot comparison of binding predictions for CD8+ T cell epitopes.
Figure 33:
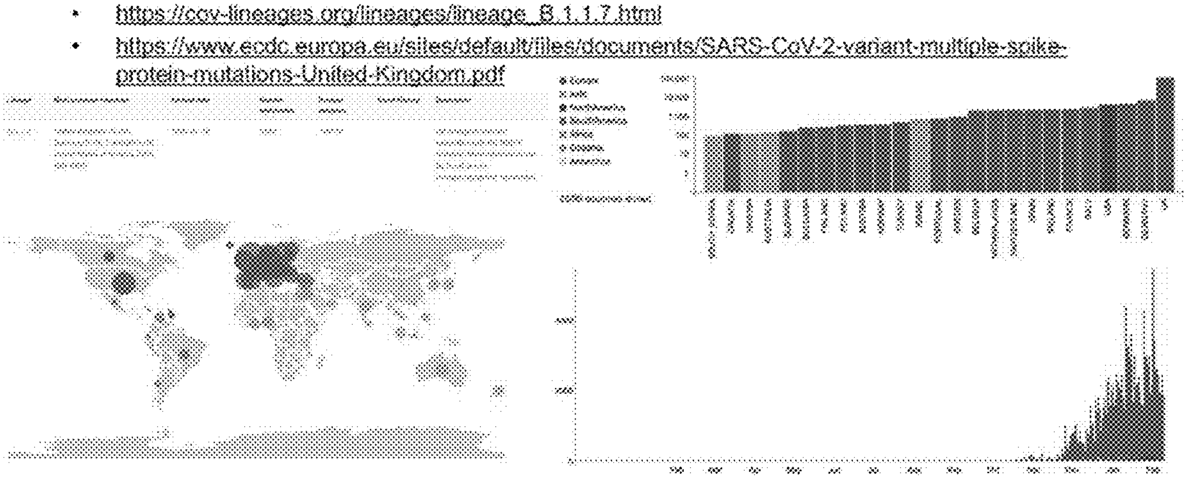
FIGS. 33-42 illustrate graphical representations of SARS-CoV-2 lineages of interest for the B.1.1.7: UK; B.1.351: South Africa; B.1.1.28, P1, P2: Brazil; B.1.177: Europe; B.1.427: Los Angeles; B.1.429: Los Angeles; B.1.526: New York; B.1.525: Denmark, UK, Nigeria; A.23.1: UK, Uganda; and B.1.243: USA, Arizona lineages.
Figure 34:
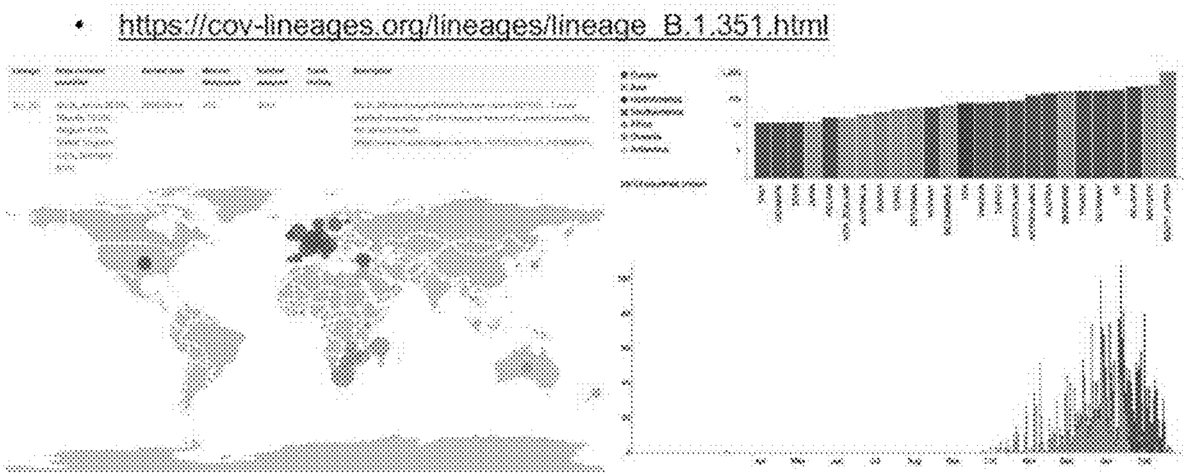
Figure 35:
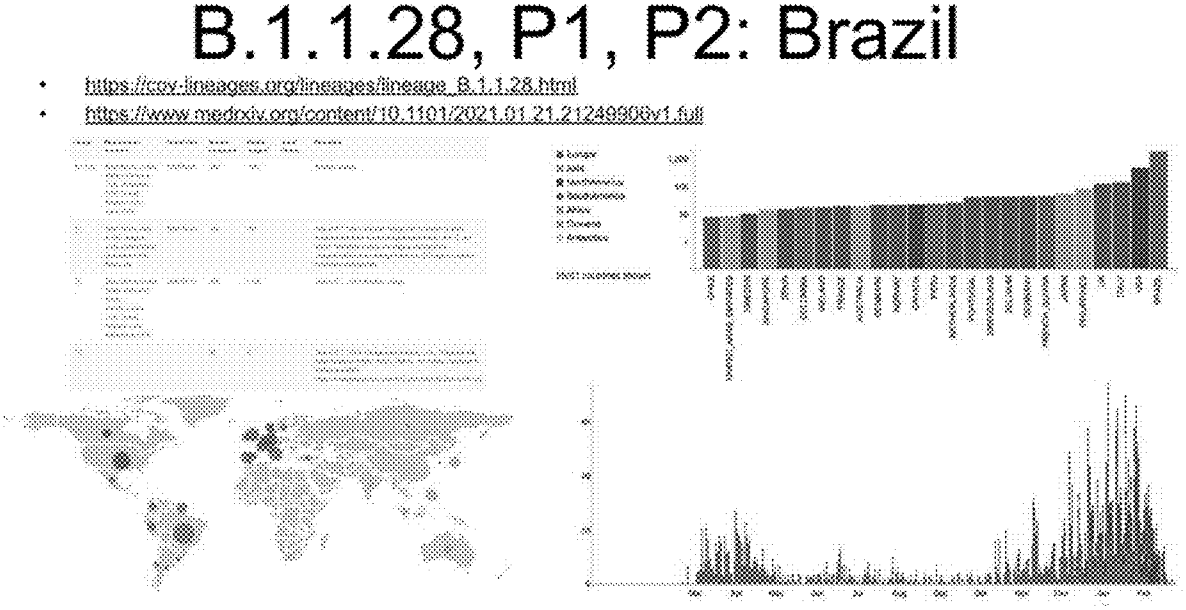
Figure 36:
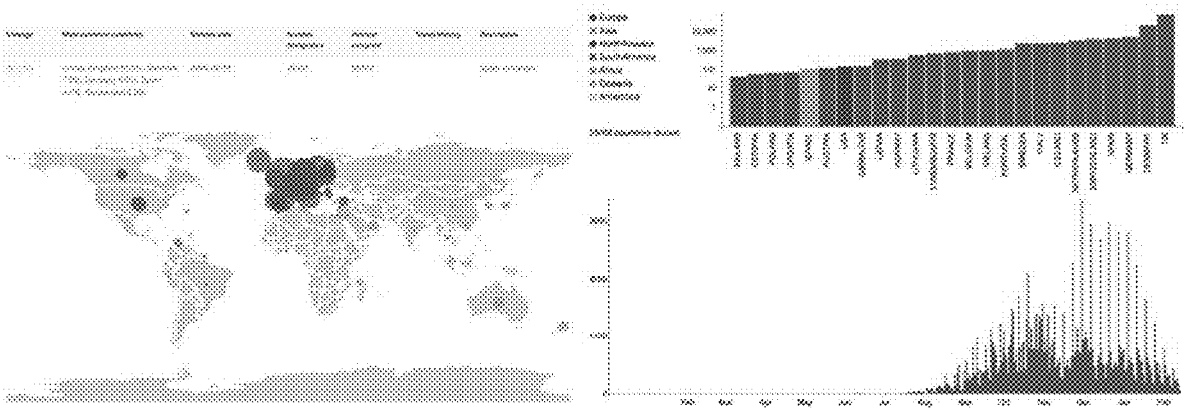
Figure 37:
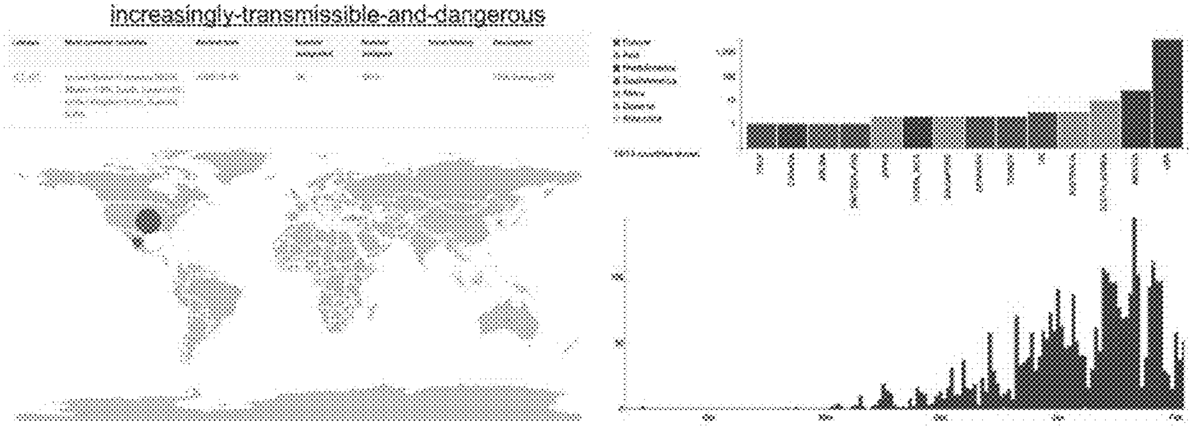
Figure 38:
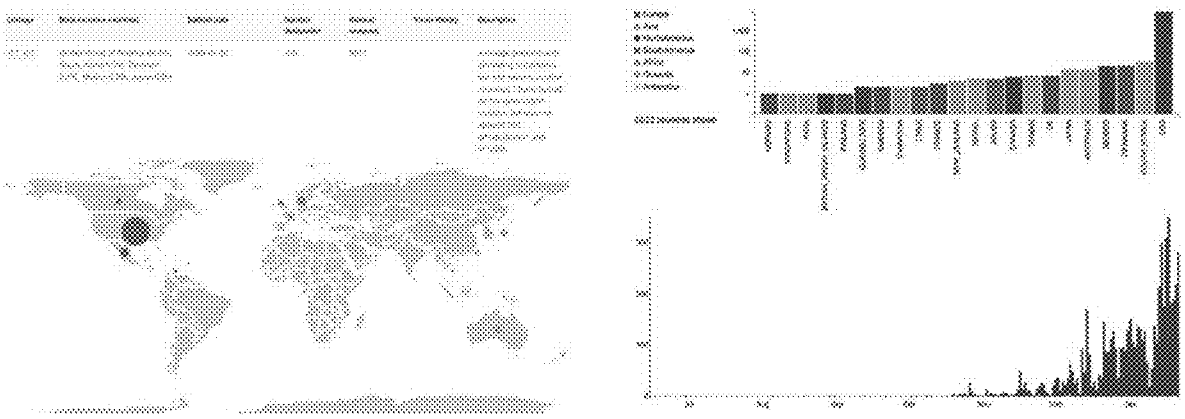
Figure 39:
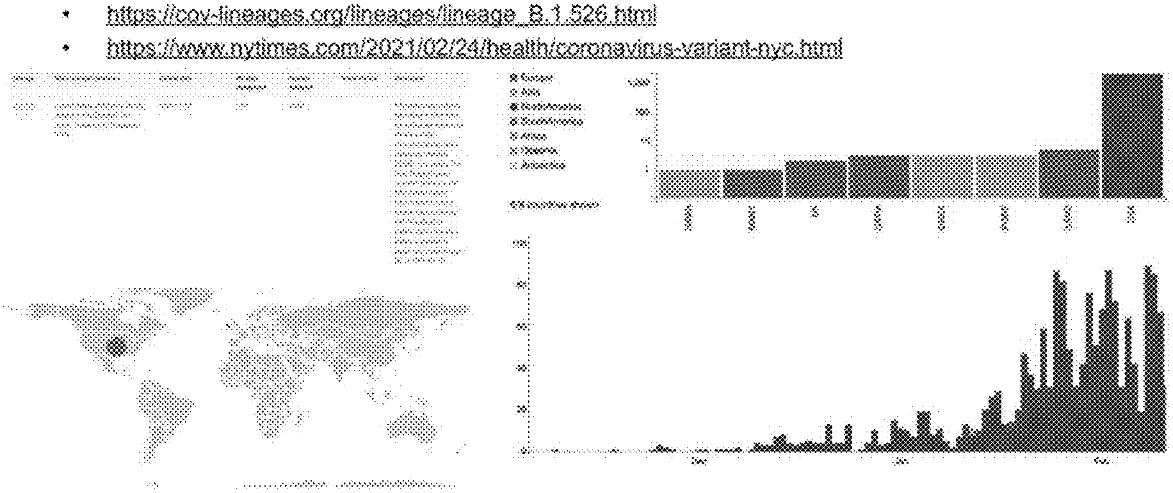
Figure 40:
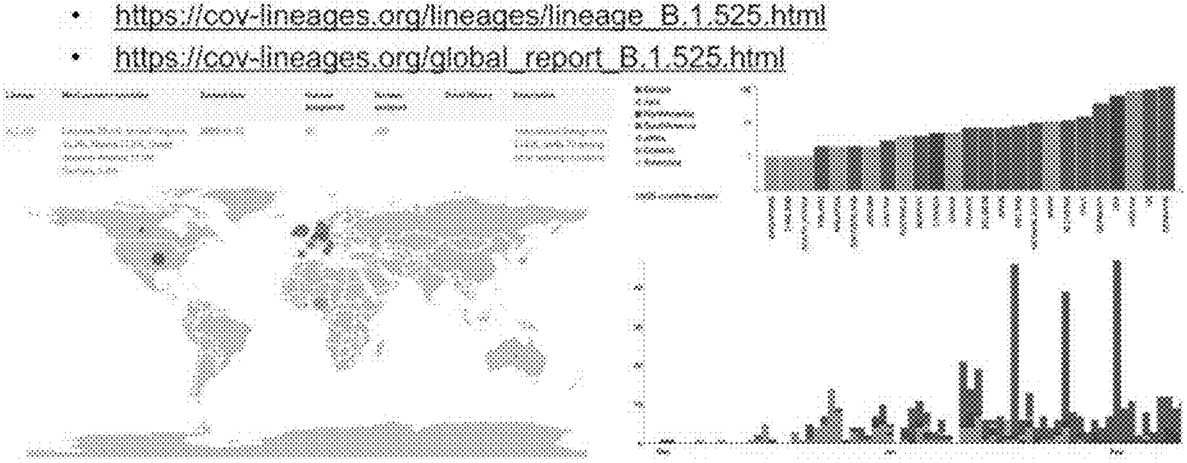
Figure 41:
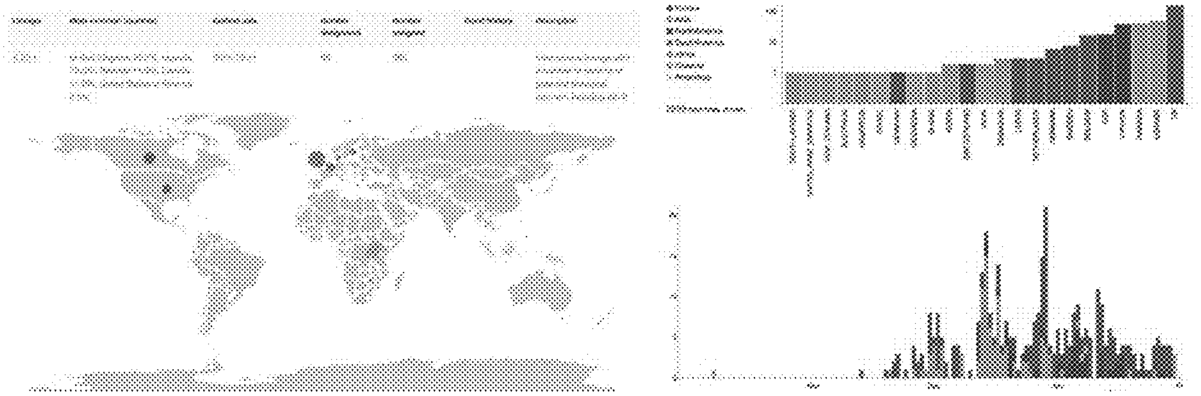
Figure 42:
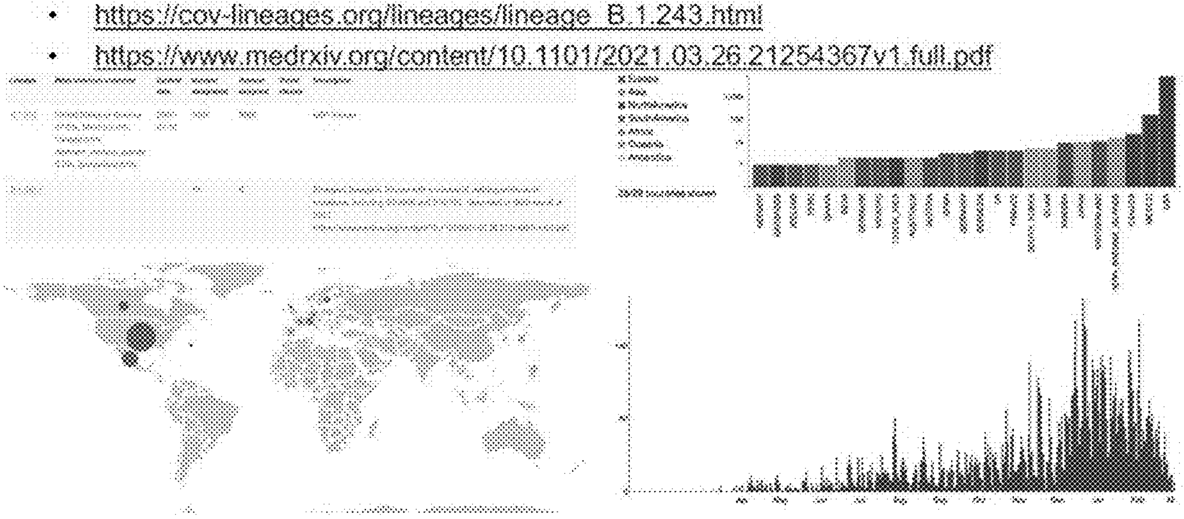

FIG. 31 illustrates a performance validation hotspot comparison of binding predictions for CD8+ T cell epitopes.

FIG. 32 illustrates a listing of SARS-CoV-2 lineages of interest.

FIGS. 33-42 illustrate graphical representations of SARS-CoV-2 lineages of interest for the B.1.1.7: UK; B.1.351: South Africa; B.1.1.28, P1, P2: Brazil; B.1.177: Europe; B.1.427: Los Angeles; B.1.429: Los Angeles; B.1.526: New York; B.1.525: Denmark, UK, Nigeria; A.23.1: UK, Uganda; and B.1.243: USA, Arizona lineages.

Figure 43:
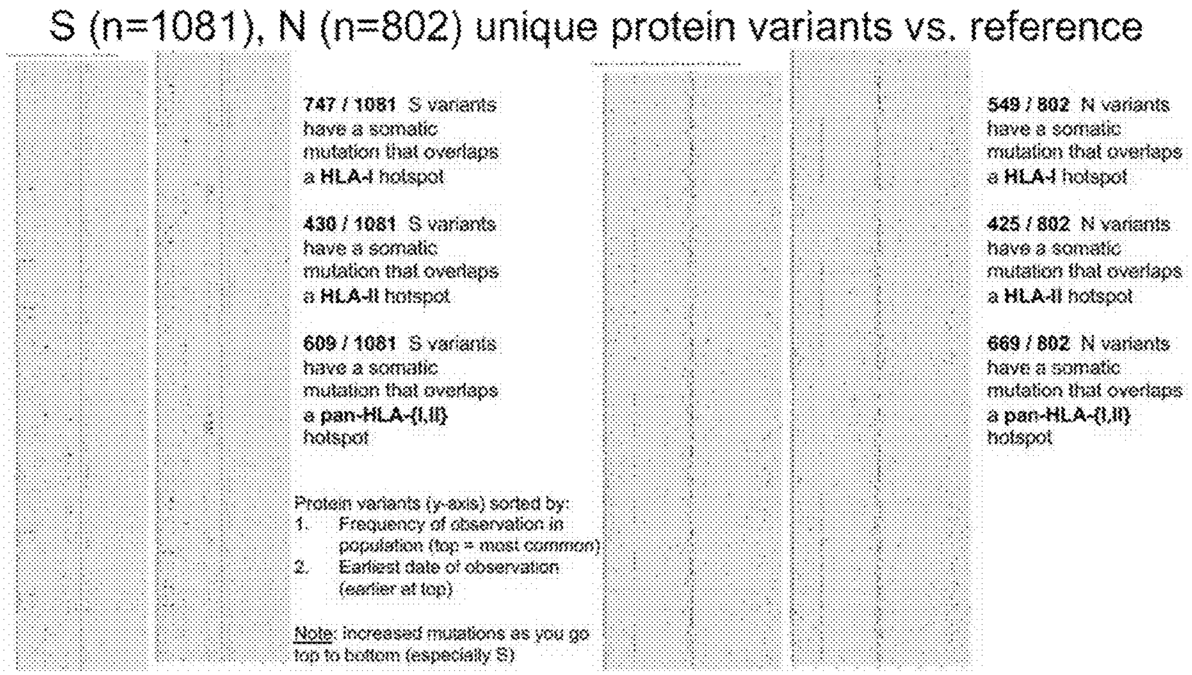
FIG. 43 illustrates SARS-CoV-2 S (n=1081), N (n=802) unique protein variants vs. a reference in accordance with an embodiment.

FIG. 43 illustrates SARS-CoV-2 S (n=1081), N (n=802) unique protein variants vs. a reference in accordance with an embodiment.

Figure 44:
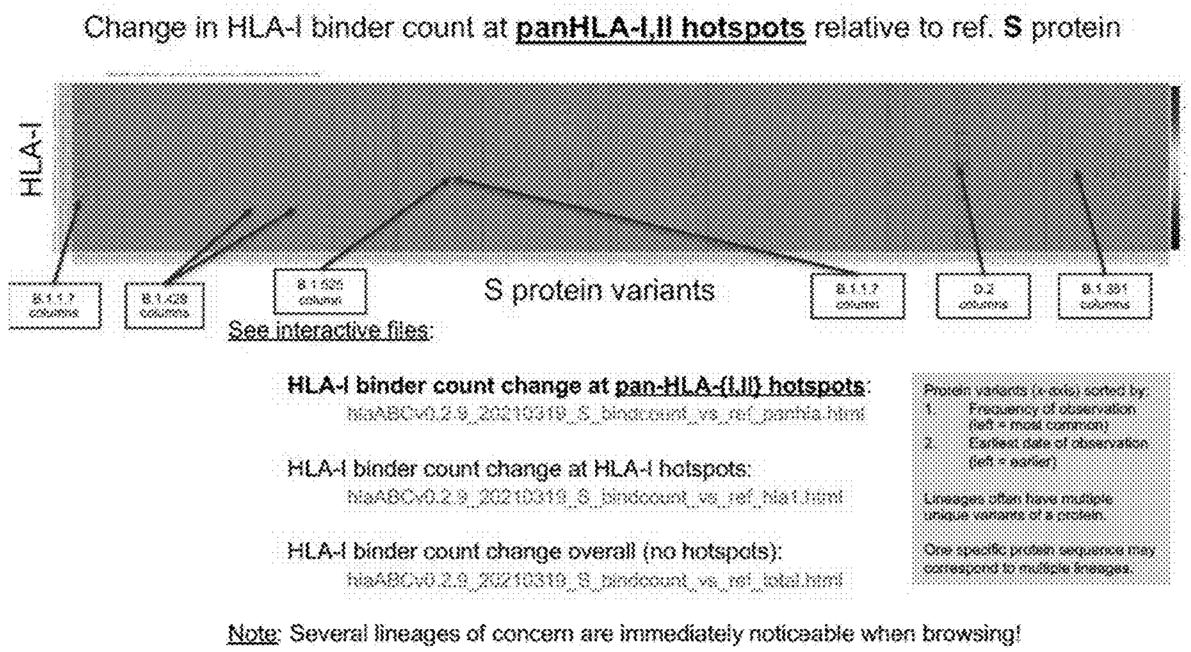
FIG. 44 illustrates change in HLA-I binder count at pan-HLA-I, II hotspots relative to a reference SARS-CoV-2 S protein in accordance with an embodiment.

FIG. 44 illustrates change in HLA-I binder count at pan-HLA-I, II hotspots relative to a reference SARS-CoV-2 S protein in accordance with an embodiment.

FIG. 45 illustrates SARS-CoV-2 S variants with the most relative binder loss (vs. a reference) across HLA-I alleles in accordance with an embodiment.

Figure 46:
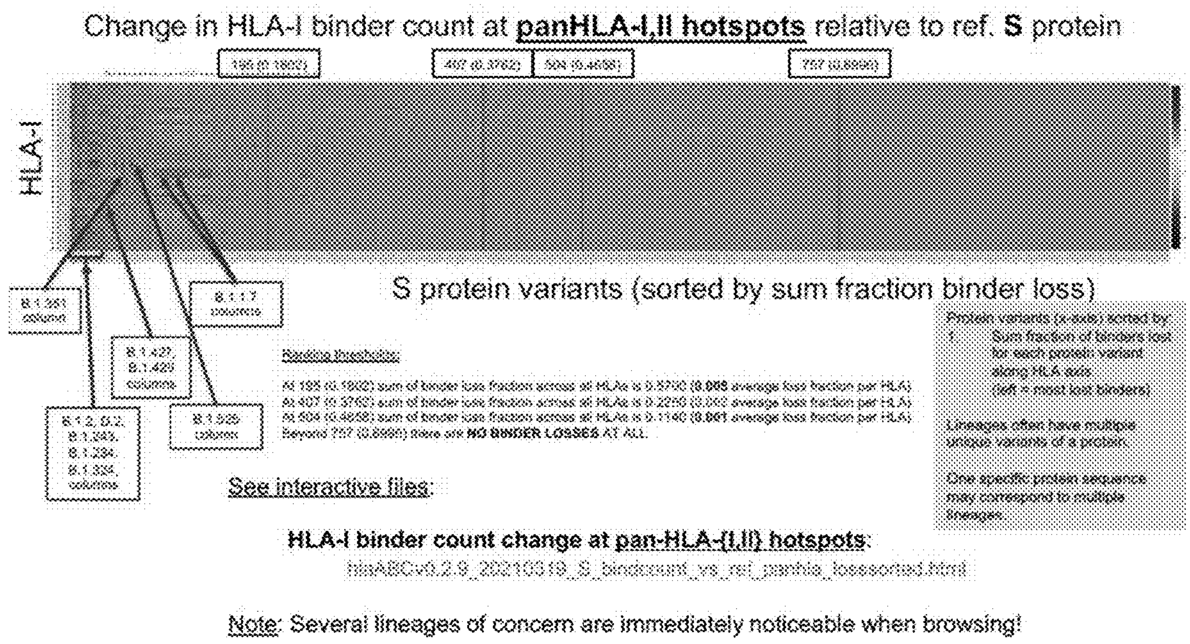
FIG. 46 illustrates change in HLA-I binder count at pan-HLA-I, II hotspots relative to a reference SARS-CoV-2 S protein in accordance with an embodiment.

FIG. 46 illustrates change in HLA-I binder count at pan-HLA-I, II hotspots relative to a reference SARS-CoV-2 S protein in accordance with an embodiment.

Figure 47:
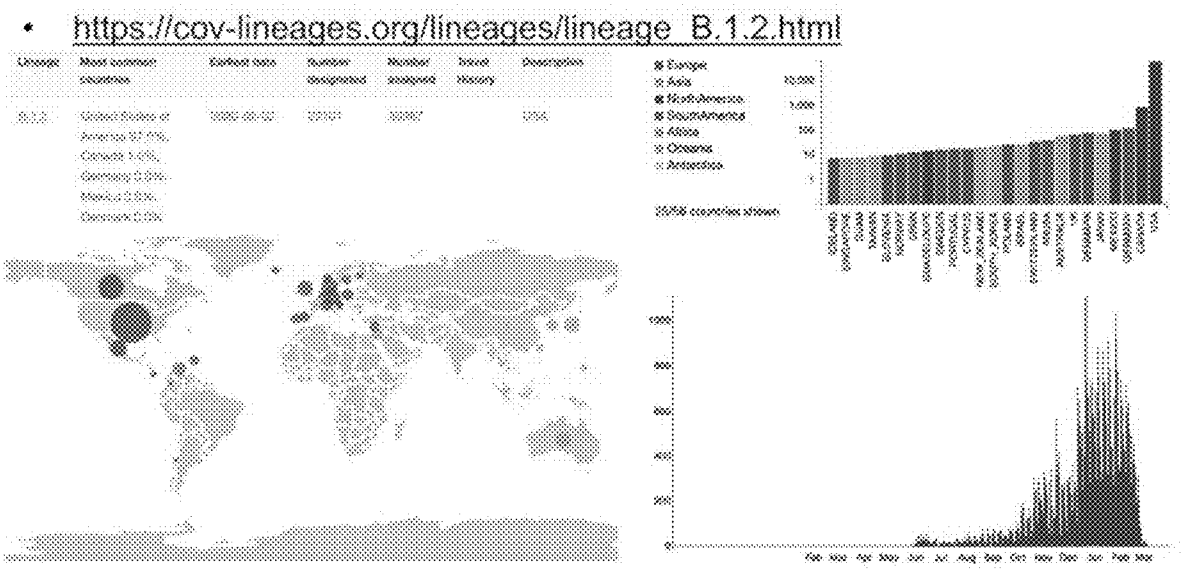
FIG. 47 illustrates a graphical representation of the SARS-CoV-2 lineage of interest for the B.1.2: USA lineage.

FIG. 47 illustrates a graphical representation of the SARS-CoV-2 lineage of interest for the B.1.2: USA lineage.

Figure 48:
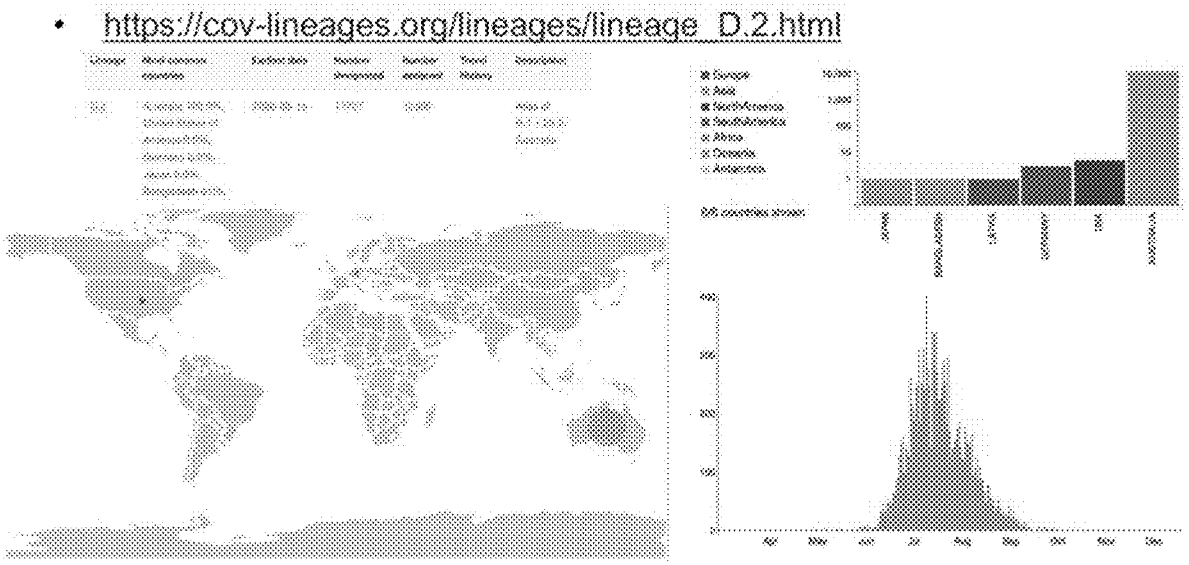
FIG. 48 illustrates a graphical representation of the SARS-CoV-2 lineage of interest for the D.2: Australia lineage.

FIG. 48 illustrates a graphical representation of the SARS-CoV-2 lineage of interest for the D.2: Australia lineage.

Figure 49:
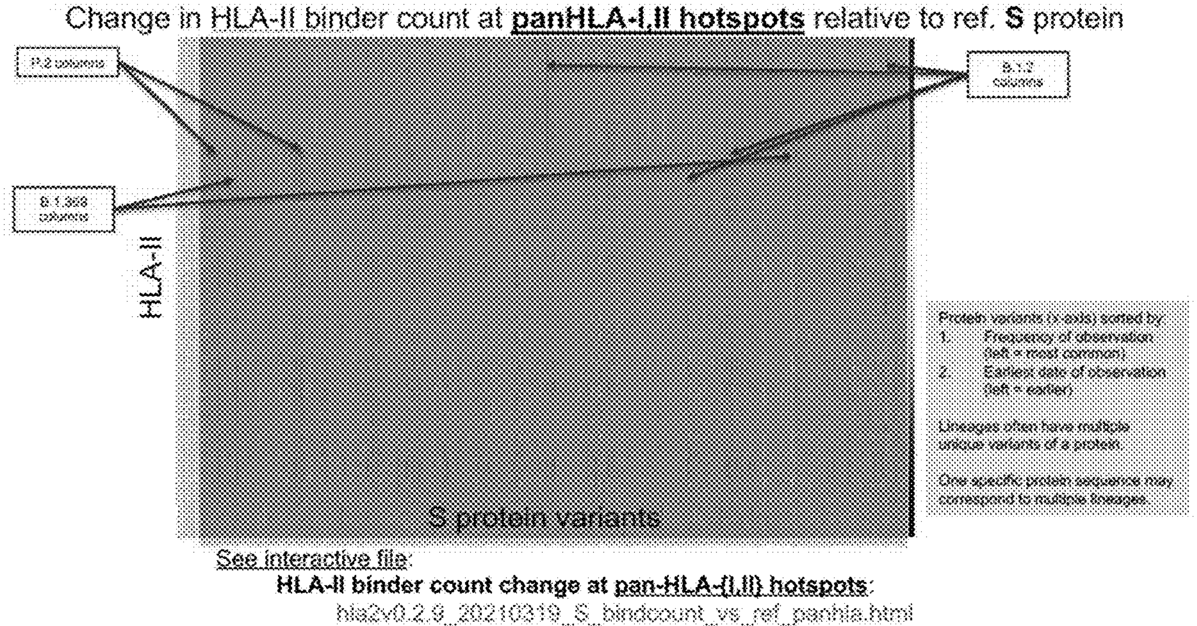
FIG. 49 illustrates change in HLA-II binder count at pan-HLA-I, II hotspots relative to a reference SARS-CoV-2 S protein.

FIG. 49 illustrates change in HLA-II binder count at pan-HLA-I, II hotspots relative to a reference SARS-CoV-2 S protein.

FIG. 50 illustrates SARS-CoV-2 S variants with the most relative binder loss (vs. a reference) across HLA-II alleles in accordance with an embodiment.

Figure 51:
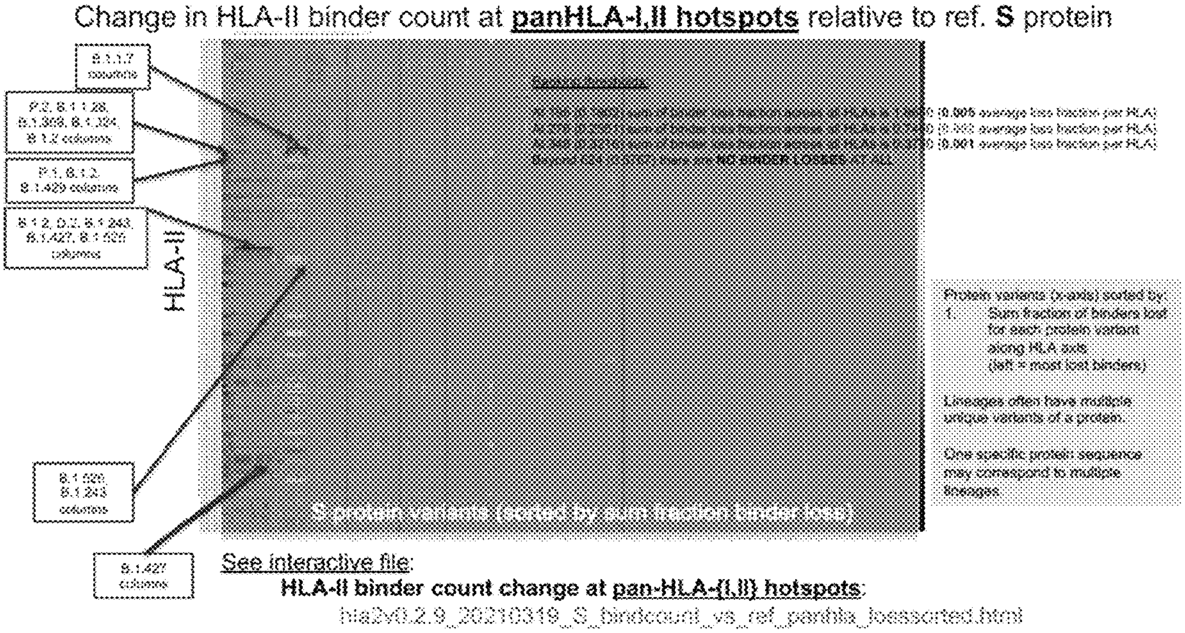
FIG. 51 illustrates change in HLA-II binder count at pan-HLA-I, II hotspots relative to a reference SARS-CoV-2 S protein.

FIG. 51 illustrates change in HLA-II binder count at pan-HLA-I, II hotspots relative to a reference SARS-CoV-2 S protein.

Figure 52:
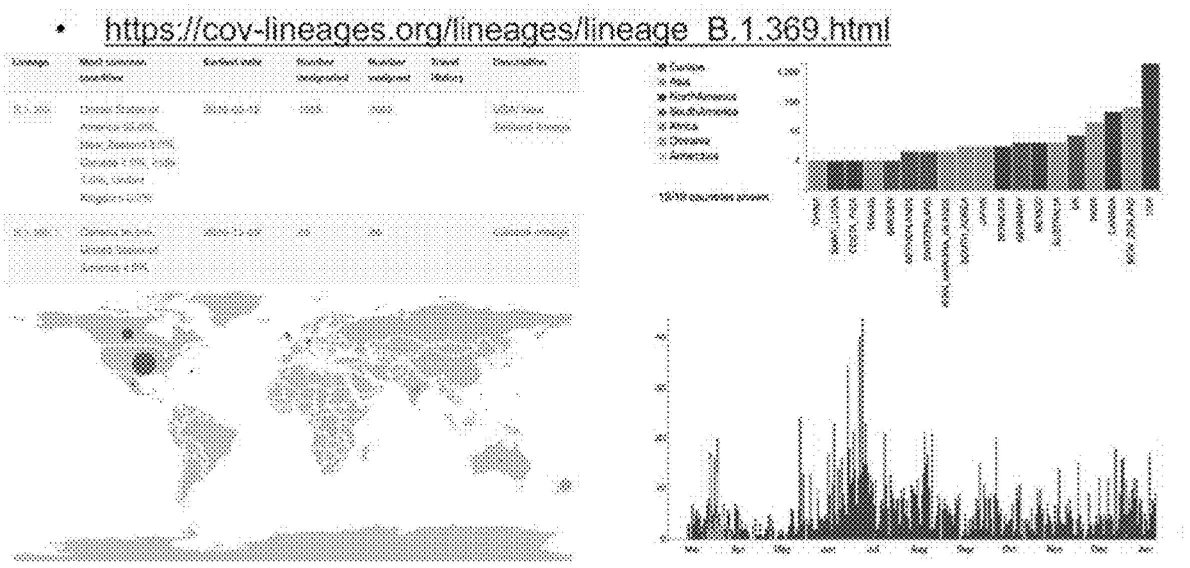
FIG. 52 illustrates a graphical representation of the SARS-CoV-2 lineage of interest for the B.1.369: USA/New Zealand/Canada lineage.

FIG. 52 illustrates a graphical representation of the SARS-CoV-2 lineage of interest for the B.1.369: USA/New Zealand/Canada lineage.

FIG. 53 illustrates change in HLA-I binder count at pan-HLA-I, II hotspots relative to a reference SARS-CoV-2 N protein.

FIG. 54 illustrates SARS-CoV-2 N variants with the most relative binder loss (vs. a reference) across HLA-I alleles.

Figure 55:
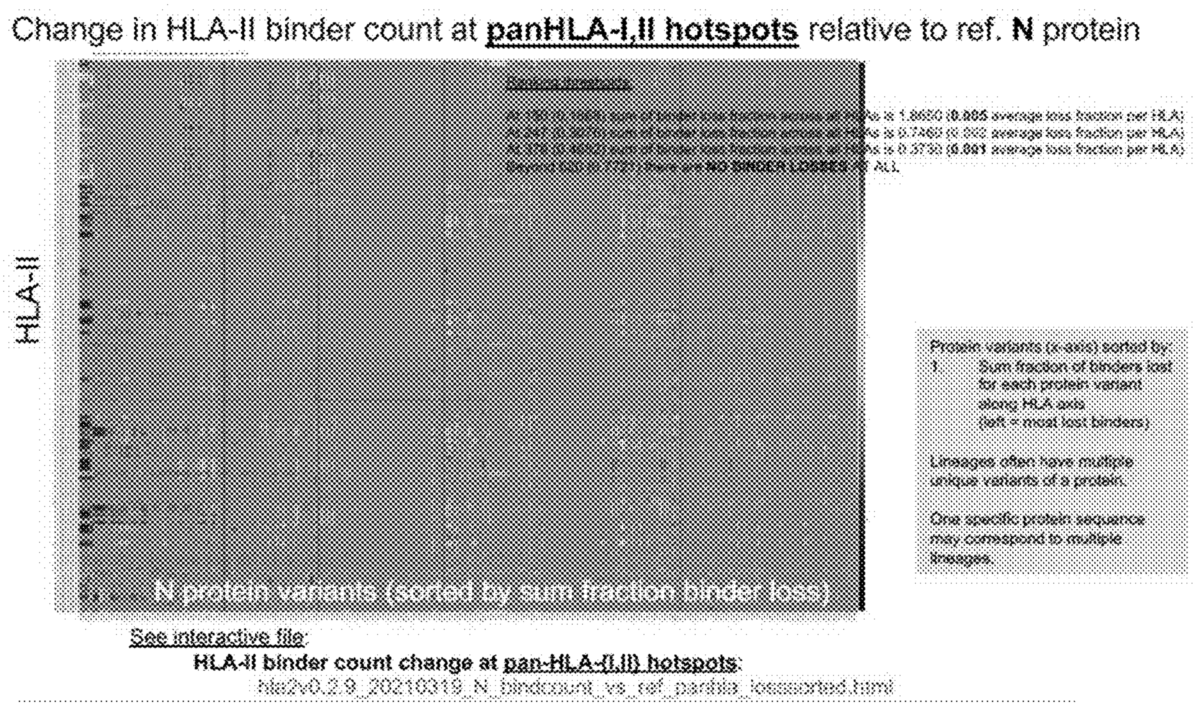
FIG. 55 illustrates change in HLA-II binder count at pan-HLA-I, II hotspots relative to a reference SARS-CoV-2 N protein.

FIG. 55 illustrates change in HLA-II binder count at pan-HLA-I, II hotspots relative to a reference SARS-CoV-2 N protein.

FIG. 56 illustrates SARS-CoV-2 N variants with most relative binder loss (vs. a reference) across HLA-II alleles.

FIG. 57 illustrates a lineage of interest ranking of worst-case binder loss relative to all observed SARS-CoV-2 S, N protein variants.

FIG. 58 illustrates binder loss rankings for all lineages with S HLA-I or HLA-II binder loss fraction (vs. a reference SARS-CoV-2 S protein) in the top 2%.

FIG. 59 illustrates performance validation data conclusions regarding the SARS-CoV-2 B.1.351: South Africa lineage.

FIG. 60 illustrates performance validation data conclusions regarding SARS-CoV-2 lineages of interest.

FIG. 61 illustrates performance validation data conclusions regarding SARS-CoV-2 lineages with S in the top 2% sum fraction of binders lost for HLA-I or HLA-II.

FIG. 62 illustrates performance validation data conclusions regarding SARS-CoV-2 lineages with S in the top 5% sum fraction of binders lost for HLA-I or HLA-II.

FIG. 63 illustrates performance validation data conclusions regarding SARS-CoV-2 lineages with S in the top 10% sum fraction of binders lost for HLA-I or HLA-II.

FIG. 64 illustrates performance validation data conclusions regarding SARS-CoV-2 lineages with S in the top 20% sum fraction of binders lost for HLA-I or HLA-II.

Figure 65:
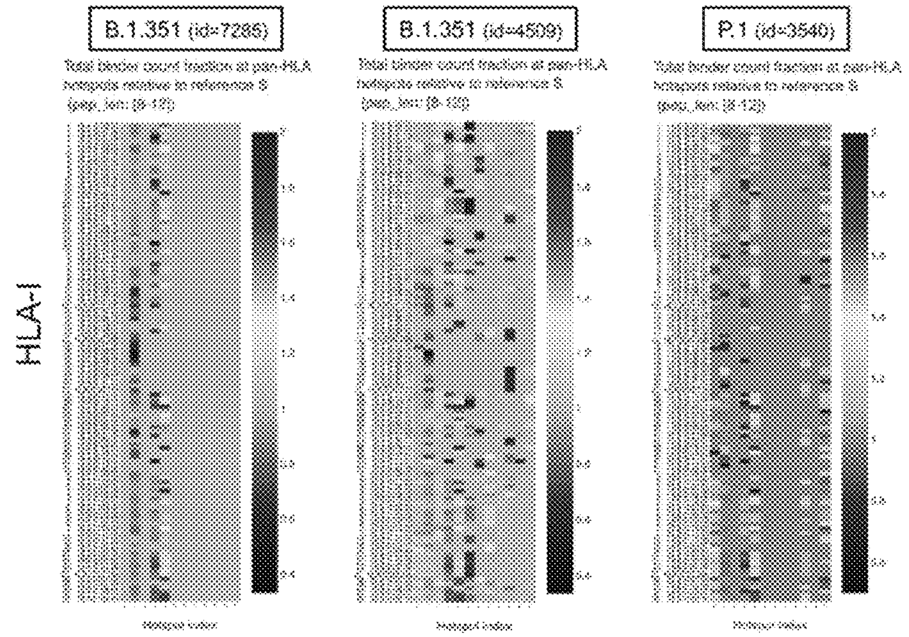
FIG. 65 illustrates change in HLA-I binder count at pan-HLA-I, II hotspots relative to a reference SARS-CoV-2 S protein.

FIG. 65 illustrates change in HLA-I binder count at pan-HLA-I, II hotspots relative to a reference SARS-CoV-2 S protein.

Figure 66:
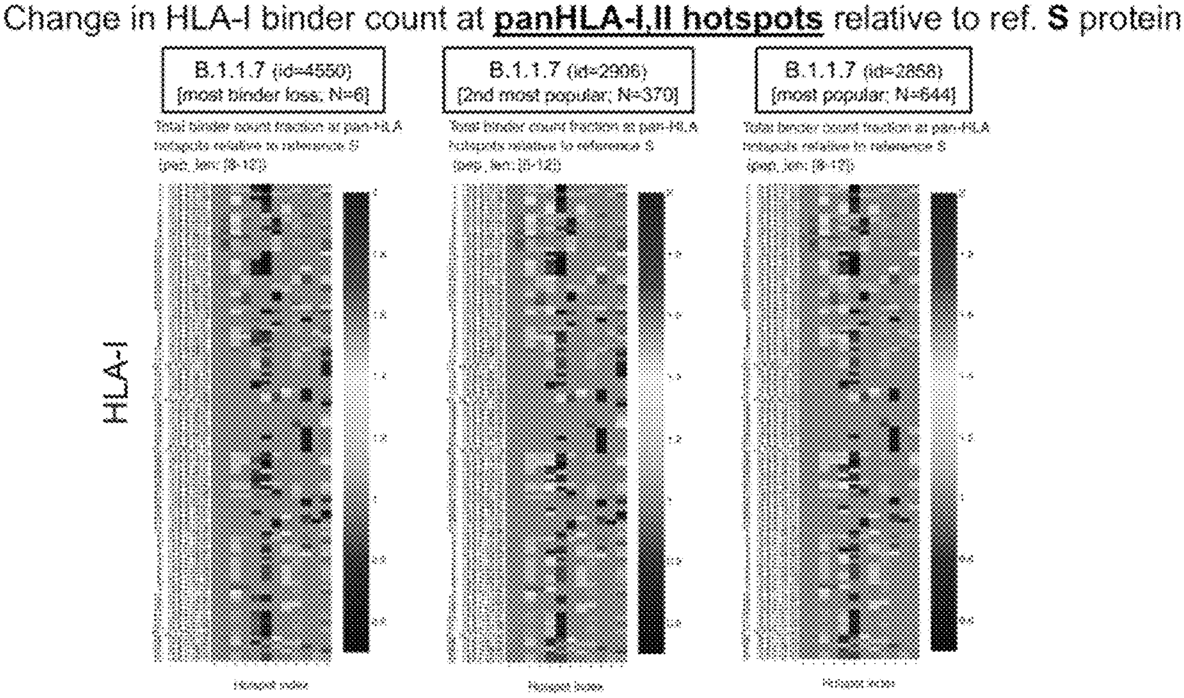
FIG. 66 further illustrates change in HLA-I binder count at pan-HLA-I, II hotspots relative to a reference SARS-CoV-2 S protein.

FIG. 66 further illustrates change in HLA-I binder count at pan-HLA-I, II hotspots relative to a reference SARS-CoV-2 S protein.

The foregoing specification is to be understood as being in every respect illustrative and exemplary, but not restrictive, and the scope of the invention disclosed herein is not to be determined from the specification, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

I claim:

1. A computerized method of vaccinating a patient against a viral infection, the method comprising:
- configuring a classifier model trained to process encoded variable-length peptides of a viral protein such that, independently per pan-human leukocyte antigen (HLA), the classifier model is operable to determine (a) an average binding prediction of overlapping peptides at each position of the viral protein, (b) a maximum value of a binding prediction of overlapping peptides at each position of the viral protein, (c) standard deviation of a binding prediction of overlapping peptides at each position of the viral protein, and (d) a combination of one or more of (a)-(c);
- configuring a classification engine to use the classifier model to determine average binding predictions of overlapping peptides at each position of the viral protein independently for each of a plurality of test HLAs comprising HLA-I and HLA-II functional groupings, wherein the determining includes classifying a peptide as a binder when an average binding prediction corresponding to the peptide satisfies a binding value threshold, and
- administering an mRNA-based vaccine encoding the peptide to the patient.

2. The method of claim 1, further comprising:
- obtaining a plurality of test HLAs encoded into variable-length proteins, wherein the plurality of test HLAs comprises HLA-I and HLA-II functional groupings;
- processing the encoded variable-length peptides corresponding to the viral protein and the variable-length proteins corresponding to the plurality of test HLAs using the classifier model such that, independently per test HLA, the classifier model is operable to determine an average binding prediction of overlapping peptides at each position of the viral protein;
- independently per test HLA:
- mapping in aggregate average binding predictions to locations along the test viral protein such that peptide-HLA interaction is indicated;
- determining nearest max locations for the average binding predictions using a sliding window having a fixed length;
- determining top max regions by selecting the nearest max locations having average binding predictions within a top percentage of values;
- selecting peptides classified as binders that overlap the top max regions; and
- determining a pan-HLA max region, wherein the determining includes setting unselected locations to zero, calculating a mean along an HLA axis of the average binding prediction, and selecting pan-HLA maxima within a top percentage of values based on the mean;
- independently for each of the HLA-I and HLA-II functional groupings:
- filtering the selected peptides classified as binders to identify candidate peptides that overlap the top max regions based on an aggregate of the pan-HLA max regions; and
- including mRNA encoding one or more of the candidate peptides in an mRNA-based vaccine or therapeutic treatment.

3. The method of claim 2, wherein the viral protein comprises a SARS-CoV-2 protein variant.

4. The method of claim 3, wherein the SARS-COV-2 protein variant comprises a SARS-COV-2 nucleocapsid (N) protein variant.

5. The method of claim 3, wherein the SARS-COV-2 protein variant comprises a SARS-COV-2 spike(S) protein variant.

6. The method of claim 2, wherein each of the encoded variable-length peptides is 8 to 15 amino acids in length.

7. The method of claim 2, wherein the fixed length of the sliding window is based on a dominant peptide length of the variable-length peptides.

8. The method of claim 2, wherein the encoded variable-length peptides have a dominant peptide length equal to 9-mers.

9. The method of claim 2, wherein the encoded variable-length peptides have a dominant peptide length equal to 15-mers.

10. The method of claim 2, wherein the plurality of test HLAs corresponds to HLA allele frequencies in worldwide populations.

11. The method of claim 2, wherein the HLA-I functional grouping comprises HLA-I protein sequences.

12. The method of claim 2, wherein the HLA-II functional grouping comprises HLA-II alpha chain and beta chain sequences.

13. The method of claim 2, wherein the top max regions are determined by selecting the nearest max locations having average binding predictions within a top 10% of values.

14. The method of claim 2, wherein the top max regions are determined by selecting the nearest max locations having average binding predictions within a top 25% of values.

15. The method of claim 2, wherein the pan-HLA max region is determined by selecting pan-HLA maxima within a top 25% of values.

16. The method of claim 2, wherein the mRNA-based vaccine or therapeutic treatment is administered to a patient having a SARS-COV-2 infection.

17. The method of claim 2, further comprising selecting at least one of the candidate peptides for inclusion in an mRNA-based vaccine for the patient based on HLA allele frequencies in worldwide populations.

18. The method of claim 2, wherein the mapping of peptide-HLA interaction includes indicating locations signifying co-occurrences of peptide attention and HLA attention.

19. The method of claim 1, further comprising training the classifier model using encoded variable-length peptides corresponding to a training viral protein and encoded variable-length proteins corresponding to one or more HLA alleles in the human population.

20. The method of claim 1, wherein the binding value threshold is one of 0.4, 0.6, and 0.8.

21. A non-transitory computer-readable medium having computer instructions stored thereon for determining pan-HLA binding of viral proteins, which, when executed by a processor, cause the processor to perform the method of claim 1.

22. A treatment method comprising:

obtaining a viral protein encoded into variable-length peptides;

obtaining a plurality of HLAs encoded into variable-length proteins, wherein the plurality of HLAs comprises HLA-I and HLA-II functional groupings;

determining, by a classification engine configured to use a classifier model trained to process encoded variable-length peptides, average binding predictions of overlapping peptides at each position of the viral protein independently for each of the plurality of HLAs comprising HLA-I and HLA-II functional groupings, wherein the determining includes classifying a peptide as a binder when an average binding prediction corresponding to the peptide satisfies a binding threshold value;

independently per HLA:

mapping in aggregate average binding predictions to locations along the test viral protein such that peptide-HLA interaction is indicated;

determining nearest max locations for the average binding predictions using a sliding window having a fixed length;

determining top max regions by selecting the nearest max locations having average binding predictions within a top percentage of values;

selecting peptides classified as binders that overlap the top max regions; and determining a pan-HLA max region, wherein the determining includes setting unselected locations to zero, calculating a mean along an HLA axis of the average binding prediction, and selecting pan-HLA maxima within a top percentage of values based on the mean;

independently for each of the HLA-I and HLA-II functional groupings:

filtering the selected peptides classified as binders to identify candidate peptides that overlap the top max regions based on an aggregate of the pan-HLA max regions; and administering an mRNA-based vaccine comprising an mRNA encoding at least one of the candidate peptides to a patient identified as having SARS-COV-2.

23. A computerized method of treating a tumor in a patient, the method comprising:

configuring a classifier model trained to process encoded variable-length peptides of a patient-specific neoantigen from the tumor such that, independently per HLA, the classifier model is operable to determine (a) an average binding prediction of overlapping peptides at each position of the neoantigen, (b) a maximum value of a binding prediction of overlapping peptides at each position of the neoantigen, (c) standard deviation of a binding prediction of overlapping peptides at each position of the neoantigen, and (d) a combination of one or more of (a)-(c);

configuring a classification engine to use the classifier model to determine average binding predictions of overlapping peptides at each position of the neoantigen independently for each of a plurality of test HLAs comprising HLA-I and HLA-II functional groupings, wherein the determining includes classifying a peptide as a binder when an average binding prediction corresponding to the peptide satisfies a binding value threshold, and administering an mRNA-based vaccine encoding the peptide to the patient.

24. The method of claim 23, further comprising:

obtaining a plurality of test HLAs encoded into variable-length proteins, wherein the plurality of test HLAs comprises HLA-I and HLA-II functional groupings;

processing the encoded variable-length peptides corresponding to the neoantigen and the variable-length proteins corresponding to the plurality of test HLAs using the classifier model such that, independently per test HLA, the classifier model is operable to determine an average binding prediction of overlapping peptides at each position of the neoantigen;

independently per test HLA:

mapping in aggregate average binding predictions to locations along the test neoantigen such that peptide-HLA interaction is indicated;

determining nearest max locations for the average binding predictions using a sliding window having a fixed length;

determining top max regions by selecting the nearest max locations having average binding predictions within a top percentage of values;

selecting peptides classified as binders that overlap the top max regions; and determining a pan-HLA max region, wherein the determining includes setting unselected locations to zero, calculating a mean along an HLA axis of the average binding prediction, and selecting pan-HLA maxima within a top percentage of values based on the mean;

independently for each of the HLA-I and HLA-II functional groupings:

filtering the selected peptides classified as binders to identify candidate peptides that overlap the top max regions based on an aggregate of the pan-HLA max regions; and including mRNA encoding one or more of the candidate peptides in an mRNA-based vaccine.

25. The method of claim 24, wherein each of the encoded variable-length peptides is 8 to 15 amino acids in length.

26. The method of claim 24, wherein the fixed length of the sliding window is based on a dominant peptide length of the variable-length peptides.

27. The method of claim 24, wherein the encoded variable-length peptides have a dominant peptide length equal to 9-mers.

28. The method of claim 24, wherein the encoded variable-length peptides have a dominant peptide length equal to 15-mers.

29. The method of claim 24, wherein the plurality of test HLAs corresponds to HLA allele frequencies in worldwide populations.

30. The method of claim 24, wherein the HLA-I functional grouping comprises HLA-I protein sequences.

* * * * *